United States Patent
Zale et al.

(10) Patent No.: US 10,137,088 B2
(45) Date of Patent: Nov. 27, 2018

(54) THERAPEUTIC NANOPARTICLES HAVING EGFR LIGANDS AND METHODS OF MAKING AND USING SAME

(71) Applicant: Pfizer Inc., New York, NY (US)

(72) Inventors: Stephen E. Zale, Hopkinton, MA (US); Kevin Andrew McDonnell, Lexington, MA (US); Allen Thomas Horhota, Westford, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/241,977

(22) Filed: Aug. 19, 2016

(65) Prior Publication Data

US 2017/0224620 A1 Aug. 10, 2017

Related U.S. Application Data

(60) Provisional application No. 62/369,590, filed on Aug. 1, 2016, provisional application No. 62/293,609, filed on Feb. 10, 2016.

(51) Int. Cl.

| | |
|---|---|
| *A61K 9/14* | (2006.01) |
| *A61K 38/17* | (2006.01) |
| *A61K 9/00* | (2006.01) |
| *A61K 47/34* | (2017.01) |
| *A61K 9/51* | (2006.01) |
| *A61K 47/60* | (2017.01) |
| *A61K 47/59* | (2017.01) |
| *A61K 47/62* | (2017.01) |
| *A61K 47/69* | (2017.01) |

(52) U.S. Cl.
CPC ............ *A61K 9/146* (2013.01); *A61K 9/0019* (2013.01); *A61K 9/5153* (2013.01); *A61K 38/1709* (2013.01); *A61K 47/34* (2013.01); *A61K 47/593* (2017.08); *A61K 47/60* (2017.08); *A61K 47/62* (2017.08); *A61K 47/6937* (2017.08); *A61K 2121/00* (2013.01)

(58) Field of Classification Search
CPC .... A61K 47/34; A61K 47/60; A61K 47/6911; A61K 9/5153
See application file for complete search history.

(56) References Cited

U.S. PATENT DOCUMENTS

| | | | |
|---|---|---|---|
| 8,318,211 B2* | 11/2012 | Zale | ........................ A61K 9/19 424/501 |
| 2010/0098681 A1 | 4/2010 | Wang et al. | |
| 2011/0053842 A1 | 3/2011 | Camphausen et al. | |

(Continued)

FOREIGN PATENT DOCUMENTS

WO       2014022535       2/2014

OTHER PUBLICATIONS

International Patent Application No. PCT/US2016/047807, filed Aug. 19, 2016, International Search Report and Written Opinion, dated Nov. 18, 2016, 16 pages.

(Continued)

*Primary Examiner* — Carlos A Azpuru
(74) *Attorney, Agent, or Firm* — Richard V. Zanzalari

(57) ABSTRACT

Provided herein in part is a therapeutic nanoparticle that includes a biocompatible polymer; a polymer—EGFR ligand conjugate, wherein the EGFR ligand is covalently bound directly or through a chemical linker to the polymer, and a therapeutic agent.

9 Claims, 27 Drawing Sheets
Specification includes a Sequence Listing.

(56) References Cited

U.S. PATENT DOCUMENTS

2014/0356444 A1* 12/2014 Troiano .................. A61K 9/10
                                                                424/501
2015/0203538 A1    7/2015 Liu et al.

OTHER PUBLICATIONS

Gong, H., et al., "Simple Method to Prepare Oligonucleotide-Conjugated Antibodies and Its Application in Multiplex Protein Detection in Single Cells." Bioconjugate Chemistry, Dec. 21, 2015, pp. 217-225, 27(1).

* cited by examiner

Pen=Penicillamine

Homo cys=Homocysteine

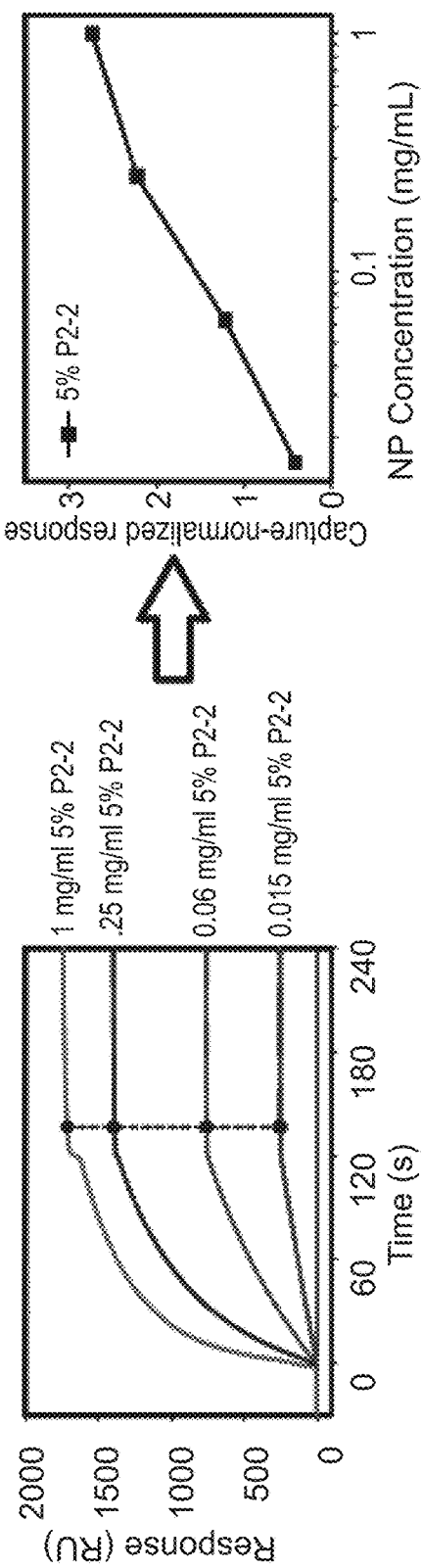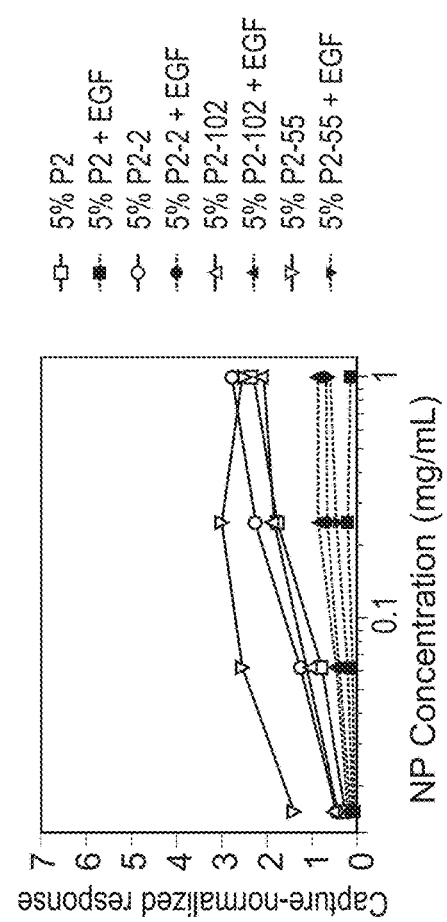
FIG. 21A
FIG. 21B

US 10,137,088 B2

```
                        SEQUENCE LISTING

<160> NUMBER OF SEQ ID NOS: 201

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Tyr His Trp Tyr Gly Tyr Thr Pro Gln Asn Val Ile
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Ala Arg Leu Leu Thr
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Glu His Gly Ala Met Glu Ile Cys
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Lys Phe Asn Asp Tyr Trp Arg Trp
1               5

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5
```

Thr Asp Cys Val Ile Phe Gly Leu Glu Thr Tyr Cys Leu Arg
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Gly Cys Leu Asp Ala Leu Trp Gln Cys Val Tyr
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Pro Asp Asp Ser Leu Pro Glu Leu Ile Cys Lys Val Arg
1               5                   10

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Pro Cys Val Leu Ile Arg Asp Tyr Tyr Leu Leu Cys Leu Glu
1               5                   10                  15

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Leu Cys His Arg Tyr Tyr His Pro Ile Cys Tyr Thr
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Met Phe Cys Phe Arg Trp Tyr Ala Gly Trp Ser Cys Val Ser
1               5                   10

<210> SEQ ID NO 11
<211> LENGTH: 10
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 11

His Phe Tyr Pro Thr Lys Thr Pro Gly Tyr
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Ala Ser Arg Ala Leu Trp Ala Phe Asn Ser Asp
1               5                   10

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Tyr Tyr Trp Gly Tyr Thr Val Asp Ile Arg Arg Gly Gly Lys
1               5                   10                  15

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Pro Cys Thr Trp Glu Val Trp Gly Arg Glu Cys Leu Gln
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Glu Cys Phe Pro Leu Ala Pro Asp Trp Leu Ser Cys Ile Leu
1               5                   10                  15

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (17)..(17)
<223> OTHER INFORMATION: Lys-PEG4-DBCO
<220> FEATURE:
```

```
<223> OTHER INFORMATION: C-term CONH2

<400> SEQUENCE: 16

Asp Pro Cys Thr Trp Glu Val Trp Gly Arg Glu Cys Leu Gln Gly Gly
1               5                   10                  15

Lys

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (17)..(17)
<223> OTHER INFORMATION: Lys-PEG4-DBCO
<220> FEATURE:
<223> OTHER INFORMATION: C-term CONH2

<400> SEQUENCE: 17

Asp Ala Cys Thr Trp Glu Val Trp Gly Arg Glu Cys Leu Gln Gly Gly
1               5                   10                  15

Lys

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (5)..(5)
<223> OTHER INFORMATION: 2-indanoyl-glycine
<220> FEATURE:
<221> NAME/KEY: MOD_RES
<222> LOCATION: (8)..(8)
<223> OTHER INFORMATION: 5'methoxy Trp
<220> FEATURE:
<221> NAME/KEY: MOD_RES
<222> LOCATION: (17)..(17)
<223> OTHER INFORMATION: Lys-PEG4-DBCO
<220> FEATURE:
<223> OTHER INFORMATION: C-term CONH2

<400> SEQUENCE: 18

Asp Pro Cys Thr Gly Glu Val Trp Gly Arg Glu Cys Leu Gln Gly Gly
1               5                   10                  15

Lys

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
```

-continued

```
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Lys-PEG4-DBCO
<220> FEATURE:
<223> OTHER INFORMATION: C-term CONH2

<400> SEQUENCE: 19

Asp Pro Xaa Thr Trp Glu Val Trp Gly Arg Glu Xaa Leu Gln Gly Gly
1               5                   10                  15
Lys

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 20

Asp Ala Xaa Thr Trp Glu Val Trp Gly Arg Glu Xaa Leu Gln Gly Gly
1               5                   10                  15
Lys

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (5)..(5)
<223> OTHER INFORMATION: 2-indanoyl-glycine
<220> FEATURE:
<221> NAME/KEY: MOD_RES
<222> LOCATION: (8)..(8)
<223> OTHER INFORMATION: 5'methoxy Trp
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 21

Asp Ala Cys Thr Gly Glu Val Trp Gly Arg Glu Cys Leu Gln Gly Gly
1               5                   10                  15
```

Lys

```
<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (5)..(5)
<223> OTHER INFORMATION: 2-indanoyl-glycine
<220> FEATURE:
<221> NAME/KEY: MOD_RES
<222> LOCATION: (8)..(8)
<223> OTHER INFORMATION: 5'methoxy Trp
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 22

Asp Pro Xaa Thr Gly Glu Val Trp Gly Arg Glu Xaa Leu Gln Gly Gly
1               5                   10                  15
Lys

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (5)..(5)
<223> OTHER INFORMATION: 2-indanoyl-glycine
<220> FEATURE:
<221> NAME/KEY: MOD_RES
<222> LOCATION: (8)..(8)
<223> OTHER INFORMATION: 5'methoxy Trp
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 23

Asp Ala Xaa Thr Gly Glu Val Trp Gly Arg Glu Xaa Leu Gln Gly Gly
```

Lys

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 24

Asp Ala Xaa Thr Trp Glu Val Trp Gly Arg Glu Xaa Leu Gln Gly Gly
1               5                   10                  15

Lys

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (17)..(17)
<223> OTHER INFORMATION: Lys-PEG5-DBCO
<220> FEATURE:
<223> OTHER INFORMATION: C-term CONH2

<400> SEQUENCE: 25

Asp Pro Cys Thr Trp Glu Val Trp Gly Arg Glu Cys Leu Gln Gly Gly
1               5                   10                  15

Lys

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (5)..(5)
<223> OTHER INFORMATION: 2-indanoyl-glycine
<220> FEATURE:
<221> NAME/KEY: MOD_RES
<222> LOCATION: (8)..(8)
<223> OTHER INFORMATION: 5'methoxy Trp
<220> FEATURE:

<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 26

Asp Ala Cys Thr Gly Glu Val Trp Gly Arg Glu Cys Leu Gln Gly Gly
1               5                   10                  15

Lys

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (5)..(5)
<223> OTHER INFORMATION: 2-indanoyl-glycine
<220> FEATURE:
<221> NAME/KEY: MOD_RES
<222> LOCATION: (8)..(8)
<223> OTHER INFORMATION: 5'methoxy Trp
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 27

Asp Pro Xaa Thr Gly Glu Val Trp Gly Arg Glu Xaa Leu Gln Gly Gly
1               5                   10                  15

Lys

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (5)..(5)
<223> OTHER INFORMATION: 2-indanoyl-glycine
<220> FEATURE:
<221> NAME/KEY: MOD_RES
<222> LOCATION: (8)..(8)
<223> OTHER INFORMATION: 5'methoxy Trp
<220> FEATURE:
<221> NAME/KEY: MOD_RES
<222> LOCATION: (12)..(12)
<223> OTHER INFORMATION: Penicillamine

```
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 28

Asp Ala Xaa Thr Gly Glu Val Trp Gly Arg Glu Xaa Leu Gln Gly Gly
1               5                   10                  15

Lys

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<223> OTHER INFORMATION: C-term CONH2

<400> SEQUENCE: 29

Asn Ser Asp Ser Glu Cys Pro Leu Ser His
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (1)..(9)
<223> OTHER INFORMATION: Disulfide bond
<220> FEATURE:
<223> OTHER INFORMATION: C-term CONH2

<400> SEQUENCE: 30

Cys Pro Leu Ser His Asp Gly Tyr Cys Leu
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (4)..(10)
<223> OTHER INFORMATION: Disulfide bond
<220> FEATURE:
<223> OTHER INFORMATION: C-term CONH2

<400> SEQUENCE: 31

Asp Gly Tyr Cys Leu His Asp Gly Val Cys
1               5                   10

<210> SEQ ID NO 32
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<223> OTHER INFORMATION: C-term CONH2

<400> SEQUENCE: 32

His Asp Gly Val Cys Met Tyr Ile Glu Ala
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<223> OTHER INFORMATION: C-term CONH2

<400> SEQUENCE: 33

Met Tyr Ile Glu Ala Leu Asp Lys Tyr Ala
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (8)..(8)
<223> OTHER INFORMATION: Cys(Acm)
<220> FEATURE:
<223> OTHER INFORMATION: C-term CONH2

<400> SEQUENCE: 34

Leu Asp Lys Tyr Ala Cys Asn Cys Val Val
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (1)..(1)
<223> OTHER INFORMATION: Cys(Acm)
<220> FEATURE:
<223> OTHER INFORMATION: C-term CONH2

<400> SEQUENCE: 35

Cys Asn Cys Val Val Gly Tyr Ile Gly Glu
1               5                   10

<210> SEQ ID NO 36
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<223> OTHER INFORMATION: C-term CONH2

<400> SEQUENCE: 36

Gly Tyr Ile Gly Glu Arg Cys Gln Tyr Arg
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<223> OTHER INFORMATION: C-term CONH2

<400> SEQUENCE: 37

Arg Cys Gln Tyr Arg Asp Leu Lys Trp Trp
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<223> OTHER INFORMATION: C-term CONH2

<400> SEQUENCE: 38

Tyr Arg Asp Leu Lys Trp Trp Glu Leu Arg
1               5                   10

<210> SEQ ID NO 39
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (1)..(18)
<223> OTHER INFORMATION: Disulfide bond
<220> FEATURE:
<221> NAME/KEY: MOD_RES
<222> LOCATION: (7)..(7)
<223> OTHER INFORMATION: Cys(Acm)
<220> FEATURE:
<223> OTHER INFORMATION: C-term CONH2

<400> SEQUENCE: 39

Cys Leu His Asp Gly Val Cys Met Tyr Ile Glu Ala Leu Asp Lys Tyr
1               5                   10                  15

Ala Cys Asn
```

```
<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (1)..(12)
<223> OTHER INFORMATION: Disulfide bond
<220> FEATURE:
<223> OTHER INFORMATION: C-term CONH2

<400> SEQUENCE: 40

Cys Met Tyr Ile Glu Ala Leu Asp Lys Tyr Ala Cys Asn
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (1)..(10)
<223> OTHER INFORMATION: Disulfide bond
<220> FEATURE:
<223> OTHER INFORMATION: C-term CONH2

<400> SEQUENCE: 41

Cys Val Val Gly Tyr Ile Gly Glu Arg Cys
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (2)..(2)
<223> OTHER INFORMATION: Propargylglycine
<220> FEATURE:
<221> NAME/KEY: MISC_FEATURE
<222> LOCATION: (5)..(14)
<223> OTHER INFORMATION: Disulfide bond
<220> FEATURE:
<223> OTHER INFORMATION: C-term CONH2

<400> SEQUENCE: 42

Gly Gly Gly Gly Cys His Ser Gly Tyr Val Gly Ala Arg Cys
1               5                   10

<210> SEQ ID NO 43
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term NH2
<220> FEATURE:
<221> NAME/KEY: MOD_RES
<222> LOCATION: (2)..(2)
<223> OTHER INFORMATION: Propargylglycine
<220> FEATURE:
<221> NAME/KEY: MISC_FEATURE
<222> LOCATION: (5)..(21)
<223> OTHER INFORMATION: Disulfide bond
<220> FEATURE:
<221> NAME/KEY: MOD_RES
<222> LOCATION: (10)..(10)
<223> OTHER INFORMATION: Cys(Acm)
<220> FEATURE:
<223> OTHER INFORMATION: C-term CONH2

<400> SEQUENCE: 43

Gly Gly Gly Gly Cys Phe His Gly Thr Cys Arg Phe Leu Val Gln Glu
1               5                   10                  15

Asp Lys Pro Ala Cys
                20

<210> SEQ ID NO 44
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (2)..(2)
<223> OTHER INFORMATION: Propargylglycine
<220> FEATURE:
<221> NAME/KEY: MISC_FEATURE
<222> LOCATION: (5)..(18)
<223> OTHER INFORMATION: Disulfide bond
<220> FEATURE:
<221> NAME/KEY: MOD_RES
<222> LOCATION: (13)..(13)
<223> OTHER INFORMATION: Cys(Acm)
<220> FEATURE:
<223> OTHER INFORMATION: C-term CONH2

<400> SEQUENCE: 44

Gly Gly Gly Gly Cys Pro Asp Ser His Thr Gln Phe Cys Phe His Gly
1               5                   10                  15

Thr Cys

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (2)..(2)
<223> OTHER INFORMATION: Propargylglycine
<220> FEATURE:
<223> OTHER INFORMATION: C-term CONH2

<400> SEQUENCE: 45

Gly Gly Gly Gly Ala Asp Leu Leu Ala Val Val Ala Ala
1               5                   10
```

```
<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (2)..(2)
<223> OTHER INFORMATION: Propargylglycine
<220> FEATURE:
<223> OTHER INFORMATION: C-term CONH2

<400> SEQUENCE: 46

Gly Gly Gly Gly Ala Arg Cys Glu His Ala Asp Ala Asp Leu
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (2)..(2)
<223> OTHER INFORMATION: Propargylglycine
<220> FEATURE:
<223> OTHER INFORMATION: C-term CONH2

<400> SEQUENCE: 47

Gly Gly Gly Gly Ser Gly Tyr Val Gly Ala Arg Cys Glu His
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (2)..(2)
<223> OTHER INFORMATION: Propargylglycine
<220> FEATURE:
<221> NAME/KEY: MOD_RES
<222> LOCATION: (6)..(6)
<223> OTHER INFORMATION: Cys(Acm)
<220> FEATURE:
<223> OTHER INFORMATION: C-term CONH2

<400> SEQUENCE: 48

Gly Gly Gly Gly Ala Cys Val Cys His Ser Gly Tyr Val Gly
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: N-term NH2
<220> FEATURE:
<221> NAME/KEY: MOD_RES
<222> LOCATION: (2)..(2)
<223> OTHER INFORMATION: Propargylglycine
<220> FEATURE:
<221> NAME/KEY: MOD_RES
<222> LOCATION: (11)..(11)
<223> OTHER INFORMATION: Cys(Acm)
<220> FEATURE:
<223> OTHER INFORMATION: C-term CONH2

<400> SEQUENCE: 49

Gly Gly Gly Gly Gln Glu Asp Lys Pro Ala Cys Val Cys His
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (2)..(2)
<223> OTHER INFORMATION: Propargylglycine
<220> FEATURE:
<223> OTHER INFORMATION: C-term CONH2

<400> SEQUENCE: 50

Gly Gly Gly Gly Cys Arg Phe Leu Val Gln Glu Asp Lys Pro
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (2)..(2)
<223> OTHER INFORMATION: Propargylglycine
<220> FEATURE:
<221> NAME/KEY: MOD_RES
<222> LOCATION: (5)..(5)
<223> OTHER INFORMATION: Cys(Acm)
<220> FEATURE:
<223> OTHER INFORMATION: C-term CONH2

<400> SEQUENCE: 51

Gly Gly Gly Gly Cys Phe His Gly Thr Cys Arg Phe Val
1               5                   10

<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (2)..(2)
<223> OTHER INFORMATION: Propargylglycine

```
<220> FEATURE:
<223> OTHER INFORMATION: C-term CONH2

<400> SEQUENCE: 52

Gly Gly Gly Gly Ser His Thr Gln Phe Cys Phe His Gly Thr
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (2)..(2)
<223> OTHER INFORMATION: Propargylglycine
<220> FEATURE:
<223> OTHER INFORMATION: C-term CONH2

<400> SEQUENCE: 53

Gly Gly Gly Gly Asn Asp Cys Pro Asp Ser His Thr Gln Phe
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (2)..(2)
<223> OTHER INFORMATION: Propargylglycine
<220> FEATURE:
<223> OTHER INFORMATION: C-term CONH2

<400> SEQUENCE: 54

Gly Gly Gly Gly Trp Ser His Phe Asn Asp Cys Pro Asp
1               5                   10

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (2)..(2)
<223> OTHER INFORMATION: Propargylglycine
<220> FEATURE:
<223> OTHER INFORMATION: C-term CONH2

<400> SEQUENCE: 55

Gly Gly Gly Gly Ala Arg Cys His Glu His Ala Asp Leu Leu Ala
1               5                   10                  15

<210> SEQ ID NO 56
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 56

Ser Glu Cys Phe Pro Leu Ala Pro Asp Trp Leu Ser Cys Ile Leu
1               5                   10                  15

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asp Pro Cys Thr Trp Glu Val Trp Gly Arg Glu Cys Leu Gln
1               5                   10

<210> SEQ ID NO 58
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Thr Asp Cys Val Ile Phe Gly Leu Glu Thr Tyr Cys Leu Arg
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Gly Cys Leu Asp Ala Leu Trp Gln Cys Val Tyr
1               5                   10

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Leu Pro Asp Asp Ser Leu Pro Glu Leu Ile Cys Lys Val Arg
1               5                   10

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Pro Cys Val Leu Ile Arg Asp Tyr Tyr Leu Leu Cys Leu Glu
1               5                   10                  15
```

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Val Leu Cys His Arg Tyr Tyr His Pro Ile Cys Tyr Thr
1               5                   10

<210> SEQ ID NO 63
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Met Phe Cys Phe Arg Trp Tyr Ala Gly Trp Ser Cys Val Ser
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

His Phe Tyr Pro Thr Lys Thr Pro Gly Tyr
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Ala Ser Arg Ala Leu Trp Ala Phe Asn Ser Asp
1               5                   10

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ser Tyr Tyr Trp Gly Tyr Thr Val Asp Ile Arg Arg Gly Gly Lys
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 67

Lys Thr Cys Val Ser Thr Thr Phe Asp Leu Trp Phe Val Cys Phe Ala
1               5                   10                  15

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Tyr His Trp Tyr Gly Tyr Thr Pro Gln Asn Val Ile
1               5                   10

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Leu Ala Arg Leu Leu Thr
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Cys Glu His Gly Ala Met Glu Ile Cys
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ala Lys Phe Asn Asp Tyr Trp Arg Trp
1               5

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Cys Pro Ala Lys Phe Ser Pro Ser Val Cys
1               5                   10

<210> SEQ ID NO 73
<211> LENGTH: 13
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 73

Tyr Cys Pro Ile Trp Lys Phe Pro Asp Glu Glu Cys Tyr
1               5                   10

<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (18)..(18)
<223> OTHER INFORMATION: Lys-DBCO
<220> FEATURE:
<223> OTHER INFORMATION: C-term CONH2

<400> SEQUENCE: 74

Ser Glu Cys Phe Pro Leu Ala Pro Asp Trp Leu Ser Cys Ile Leu Gly
1               5                   10                  15

Gly Lys

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MISC_FEATURE
<222> LOCATION: (3)..(13)
<223> OTHER INFORMATION: Disulfide bond
<220> FEATURE:
<221> NAME/KEY: MOD_RES
<222> LOCATION: (16)..(16)
<223> OTHER INFORMATION: Lys-DBCO
<220> FEATURE:
<223> OTHER INFORMATION: C-term CONH2

<400> SEQUENCE: 75

Ser Glu Cys Phe Pro Ala Ala Pro Asp Trp Leu Ser Cys Gly Gly Lys
1               5                   10                  15

<210> SEQ ID NO 76
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MISC_FEATURE
<222> LOCATION: (1)..(11)
<223> OTHER INFORMATION: Disulfide bond
<220> FEATURE:
<221> NAME/KEY: MOD_RES
<222> LOCATION: (14)..(14)
<223> OTHER INFORMATION: Lys-DBCO
<220> FEATURE:

```
<223> OTHER INFORMATION: C-term CONH2

<400> SEQUENCE: 76

Cys Phe Pro Ala Ala Pro Asp Trp Leu Ser Cys Gly Gly Lys
1               5                   10

<210> SEQ ID NO 77
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MISC_FEATURE
<222> LOCATION: (1)..(11)
<223> OTHER INFORMATION: Disulfide bond
<220> FEATURE:
<221> NAME/KEY: MOD_RES
<222> LOCATION: (14)..(14)
<223> OTHER INFORMATION: Lys-DBCO
<220> FEATURE:
<223> OTHER INFORMATION: C-term CONH2

<400> SEQUENCE: 77

Cys Phe Pro Ala Ala Pro Asp Trp Leu Ser Cys Gly Gly Lys
1               5                   10

<210> SEQ ID NO 78
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MISC_FEATURE
<222> LOCATION: (3)..(13)
<223> OTHER INFORMATION: Disulfide bond
<220> FEATURE:
<221> NAME/KEY: MOD_RES
<222> LOCATION: (7)..(7)
<223> OTHER INFORMATION: Methyl group
<220> FEATURE:
<221> NAME/KEY: MOD_RES
<222> LOCATION: (18)..(18)
<223> OTHER INFORMATION: Lys-DBCO
<220> FEATURE:
<223> OTHER INFORMATION: C-term CONH2

<400> SEQUENCE: 78

Ser Glu Cys Phe Pro Ala Ala Pro Asp Trp Leu Ser Cys Ile Leu Gly
1               5                   10                  15

Gly Lys

<210> SEQ ID NO 79
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MISC_FEATURE
<222> LOCATION: (3)..(13)
<223> OTHER INFORMATION: Disulfide bond
```

```
<220> FEATURE:
<221> NAME/KEY: MOD_RES
<222> LOCATION: (12)..(12)
<223> OTHER INFORMATION: Methyl group
<220> FEATURE:
<223> OTHER INFORMATION: C-term CONH2

<400> SEQUENCE: 79

Ser Glu Cys Phe Pro Ala Ala Pro Asp Trp Leu Ser Cys Ile Leu Gly
1               5                   10                  15

Gly Lys

<210> SEQ ID NO 80
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MISC_FEATURE
<222> LOCATION: (3)..(13)
<223> OTHER INFORMATION: Disulfide bond
<220> FEATURE:
<221> NAME/KEY: MOD_RES
<222> LOCATION: (15)..(15)
<223> OTHER INFORMATION: Methyl group
<220> FEATURE:
<223> OTHER INFORMATION: C-term CONH2

<400> SEQUENCE: 80

Ser Glu Cys Phe Pro Ala Ala Pro Asp Trp Leu Ser Cys Ile Leu Gly
1               5                   10                  15

Gly Lys

<210> SEQ ID NO 81
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MISC_FEATURE
<222> LOCATION: (3)..(13)
<223> OTHER INFORMATION: Disulfide bond
<220> FEATURE:
<221> NAME/KEY: MOD_RES
<222> LOCATION: (12)..(12)
<223> OTHER INFORMATION: Methyl group
<220> FEATURE:
<223> OTHER INFORMATION: C-term CONH2

<400> SEQUENCE: 81

Ser Glu Cys Phe Pro Ala Ala Pro Asp Trp Leu Ser Cys Ile Leu Gly
1               5                   10                  15

Gly Lys

<210> SEQ ID NO 82
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: N-term acetyl group
<220> FEATURE:
<221> NAME/KEY: MOD_RES
<222> LOCATION: (3)..(3)
<223> OTHER INFORMATION: Methyl group
<220> FEATURE:
<221> NAME/KEY: MISC_FEATURE
<222> LOCATION: (3)..(13)
<223> OTHER INFORMATION: Disulfide bond
<220> FEATURE:
<221> NAME/KEY: MOD_RES
<222> LOCATION: (18)..(18)
<223> OTHER INFORMATION: Lys-DBCO
<220> FEATURE:
<223> OTHER INFORMATION: C-term CONH2

<400> SEQUENCE: 82

Ser Glu Cys Phe Pro Ala Ala Pro Asp Trp Leu Ser Cys Ile Leu Gly
 1               5                  10                  15

Gly Lys

<210> SEQ ID NO 83
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MISC_FEATURE
<222> LOCATION: (3)..(13)
<223> OTHER INFORMATION: Disulfide bond
<220> FEATURE:
<221> NAME/KEY: MOD_RES
<222> LOCATION: (5)..(5)
<223> OTHER INFORMATION: Methyl group
<220> FEATURE:
<221> NAME/KEY: MOD_RES
<222> LOCATION: (18)..(18)
<223> OTHER INFORMATION: Lys-DBCO
<220> FEATURE:
<223> OTHER INFORMATION: C-term CONH2

<400> SEQUENCE: 83

Ser Glu Cys Phe Pro Ala Ala Pro Asp Trp Leu Ser Cys Ile Leu Gly
 1               5                  10                  15

Gly Lys

<210> SEQ ID NO 84
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MISC_FEATURE
<222> LOCATION: (3)..(13)
<223> OTHER INFORMATION: Disulfide bond
<220> FEATURE:
<221> NAME/KEY: MOD_RES
<222> LOCATION: (7)..(7)
<223> OTHER INFORMATION: Methyl group
<220> FEATURE:
<221> NAME/KEY: MOD_RES
<222> LOCATION: (18)..(18)
<223> OTHER INFORMATION: Lys-DBCO
<220> FEATURE:
<223> OTHER INFORMATION: C-term CONH2

<400> SEQUENCE: 84

Ser Glu Cys Phe Pro Ala Ala Pro Asp Trp Leu Ser Cys Ile Leu Gly
1               5                   10                  15

Gly Lys

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser-DBCO
<220> FEATURE:
<221> NAME/KEY: MISC_FEATURE
<222> LOCATION: (3)..(13)
<223> OTHER INFORMATION: Disulfide bond
<220> FEATURE:
<223> OTHER INFORMATION: C-term CONH2

<400> SEQUENCE: 85

Ser Glu Cys Phe Pro Ala Ala Pro Asp Trp Leu Ser Cys Ile Leu
1               5                   10                  15

<210> SEQ ID NO 86
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (15)..(15)
<223> OTHER INFORMATION: Propargylglycine
<220> FEATURE:
<223> OTHER INFORMATION: C-term CONH2

<400> SEQUENCE: 86

Asp Pro Cys Thr Trp Glu Val Trp Gly Arg Glu Cys Gly Gly Gly Gly
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (1)..(10)
<223> OTHER INFORMATION: Disulfide bond
<220> FEATURE:
<221> NAME/KEY: MOD_RES
<222> LOCATION: (15)..(15)
<223> OTHER INFORMATION: Propargylglycine
<220> FEATURE:
<223> OTHER INFORMATION: C-term CONH2

<400> SEQUENCE: 87

Cys Thr Trp Glu Val Trp Gly Arg Glu Cys Leu Gln Gly Gly Gly Gly
1               5                   10                  15

<210> SEQ ID NO 88
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (1)..(10)
<223> OTHER INFORMATION: Disulfide bond
<220> FEATURE:
<221> NAME/KEY: MOD_RES
<222> LOCATION: (13)..(13)
<223> OTHER INFORMATION: Propargylglycine
<220> FEATURE:
<223> OTHER INFORMATION: C-term CONH2

<400> SEQUENCE: 88

Cys Thr Trp Glu Val Trp Gly Arg Glu Cys Gly Gly Gly Gly
1               5                   10

<210> SEQ ID NO 89
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (15)..(15)
<223> OTHER INFORMATION: Propargylglycine
<220> FEATURE:
<223> OTHER INFORMATION: C-term CONH2

<400> SEQUENCE: 89

Asp Ala Cys Thr Trp Glu Val Trp Gly Arg Glu Cys Gly Gly Gly Gly
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (2)..(11)
<223> OTHER INFORMATION: Disulfide bond
<220> FEATURE:
<221> NAME/KEY: MOD_RES
<222> LOCATION: (14)..(14)
<223> OTHER INFORMATION: Propargylglycine
<220> FEATURE:
<223> OTHER INFORMATION: C-term CONH2

<400> SEQUENCE: 90

```
Ala Cys Thr Trp Glu Val Trp Gly Arg Glu Cys Gly Gly Gly Gly
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MISC_FEATURE
<222> LOCATION: (2)..(11)
<223> OTHER INFORMATION: Disulfide bond
<220> FEATURE:
<221> NAME/KEY: MOD_RES
<222> LOCATION: (14)..(14)
<223> OTHER INFORMATION: Propargylglycine
<220> FEATURE:
<223> OTHER INFORMATION: C-term CONH2

<400> SEQUENCE: 91

Ala Cys Thr Trp Glu Val Trp Gly Arg Glu Cys Gly Gly Gly Gly
1               5                   10                  15

<210> SEQ ID NO 92
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (1)..(1)
<223> OTHER INFORMATION: Propargylglycine
<220> FEATURE:
<221> NAME/KEY: MISC_FEATURE
<222> LOCATION: (3)..(12)
<223> OTHER INFORMATION: Disulfide bond
<220> FEATURE:
<223> OTHER INFORMATION: C-term CONH2

<400> SEQUENCE: 92

Gly Ala Cys Thr Trp Glu Val Trp Gly Arg Glu Cys
1               5                   10

<210> SEQ ID NO 93
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (13)..(13)
<223> OTHER INFORMATION: Propargylglycine
<220> FEATURE:
<223> OTHER INFORMATION: C-term CONH2

<400> SEQUENCE: 93
```

```
Asp Pro Cys Thr Trp Glu Val Trp Gly Arg Glu Cys Gly
1               5                   10
```

<210> SEQ ID NO 94
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (1)..(1)
<223> OTHER INFORMATION: Propargylglycine
<220> FEATURE:
<221> NAME/KEY: MISC_FEATURE
<222> LOCATION: (2)..(11)
<223> OTHER INFORMATION: Disulfide bond
<220> FEATURE:
<223> OTHER INFORMATION: C-term CONH2

<400> SEQUENCE: 94

```
Gly Cys Thr Trp Glu Val Trp Gly Arg Glu Cys
1               5                   10
```

<210> SEQ ID NO 95
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 95

```
Asp Pro Cys Ala Trp Glu Val Trp Gly Arg Glu Cys Leu Gln Gly Gly
1               5                   10                  15

Gly Gly
```

<210> SEQ ID NO 96
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 96

Asp Pro Cys Val Trp Glu Val Trp Gly Arg Glu Cys Leu Gln Gly Gly
1               5                   10                  15

Gly Gly

<210> SEQ ID NO 97
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 97

Asp Pro Cys Ser Trp Glu Val Trp Gly Arg Glu Cys Leu Gln Gly Gly
1               5                   10                  15

Gly Gly

<210> SEQ ID NO 98
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (4)..(4)
<223> OTHER INFORMATION: Propargylglycine
<220> FEATURE:
<223> OTHER INFORMATION: C-term CONH2

<400> SEQUENCE: 98

Asp Pro Cys Gly Trp Glu Val Trp Gly Arg Glu Cys Leu Gln
1               5                   10

<210> SEQ ID NO 99
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (17)..(17)
<223> OTHER INFORMATION: Propargylglycine
<220> FEATURE:

```
<223> OTHER INFORMATION: C-term CONH2

<400> SEQUENCE: 99

Asp Pro Cys Thr Ala Glu Val Trp Gly Arg Glu Cys Leu Gln Gly Gly
1               5                   10                  15

Gly Gly

<210> SEQ ID NO 100
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 100

Asp Pro Cys Thr Phe Glu Val Trp Gly Arg Glu Cys Leu Gln Gly Gly
1               5                   10                  15

Gly Gly

<210> SEQ ID NO 101
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 101

Asp Pro Cys Thr Trp Ala Val Trp Gly Arg Glu Cys Leu Gln Gly Gly
1               5                   10                  15

Gly Gly

<210> SEQ ID NO 102
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
```

```
<220> FEATURE:
<221> NAME/KEY: MOD_RES
<222> LOCATION: (6)..(6)
<223> OTHER INFORMATION: Propargylglycine
<220> FEATURE:
<223> OTHER INFORMATION: C-term CONH2

<400> SEQUENCE: 102

Asp Pro Cys Thr Trp Gly Val Trp Gly Arg Glu Cys Leu Gln
1               5                   10

<210> SEQ ID NO 103
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 103

Asp Pro Cys Thr Trp Arg Val Trp Gly Arg Glu Cys Leu Gln Gly Gly
1               5                   10                  15

Gly Gly

<210> SEQ ID NO 104
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 104

Asp Pro Cys Thr Trp Gly Val Trp Gly Arg Glu Cys Leu Gln Gly Gly
1               5                   10                  15

Gly Gly

<210> SEQ ID NO 105
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
```

```
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 105

Asp Pro Cys Thr Trp Glu Ala Trp Gly Arg Glu Cys Leu Gln Gly Gly
1               5                   10                  15

Gly Gly

<210> SEQ ID NO 106
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (7)..(7)
<223> OTHER INFORMATION: Propargylglycine
<220> FEATURE:
<223> OTHER INFORMATION: C-term CONH2

<400> SEQUENCE: 106

Asp Pro Cys Thr Trp Glu Gly Trp Gly Arg Glu Cys Leu Gln
1               5                   10

<210> SEQ ID NO 107
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 107

Asp Pro Cys Thr Trp Glu Ile Trp Gly Arg Glu Cys Leu Gln Gly Gly
1               5                   10                  15

Gly Gly

<210> SEQ ID NO 108
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 108

Asp Pro Cys Thr Trp Glu Leu Trp Gly Arg Glu Cys Leu Gln Gly Gly
1               5                   10                  15

Gly Gly

<210> SEQ ID NO 109
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 109

Asp Pro Cys Thr Trp Glu Thr Trp Gly Arg Glu Cys Leu Gln Gly Gly
1               5                   10                  15

Gly Gly

<210> SEQ ID NO 110
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 110

Asp Pro Cys Thr Trp Glu Val Ala Gly Arg Glu Cys Leu Gln Gly Gly
1               5                   10                  15

Gly Gly

<210> SEQ ID NO 111
<211> LENGTH: 18
```

<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 111

Asp Pro Cys Thr Trp Glu Val Phe Gly Arg Glu Cys Leu Gln Gly Gly
1               5                   10                  15

Gly Gly

<210> SEQ ID NO 112
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 112

Asp Pro Cys Thr Trp Glu Val Trp Ala Arg Glu Cys Leu Gln Gly Gly
1               5                   10                  15

Gly Gly

<210> SEQ ID NO 113
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (9)..(9)
<223> OTHER INFORMATION: D-alanine
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 113

Asp Pro Cys Thr Trp Glu Val Trp Ala Arg Glu Cys Leu Gln Gly Gly
1               5                   10                  15

Gly Gly

<210> SEQ ID NO 114
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (9)..(9)
<223> OTHER INFORMATION: Sarcosine
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 114

Asp Pro Cys Thr Trp Glu Val Trp Xaa Arg Glu Cys Leu Gln Gly Gly
1               5                   10                  15

Gly Gly

<210> SEQ ID NO 115
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 115

Asp Pro Cys Thr Trp Glu Val Trp Ala Arg Glu Cys Leu Gln Gly Gly
1               5                   10                  15

Gly Gly

<210> SEQ ID NO 116
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:

<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 116

Asp Pro Cys Thr Trp Glu Val Trp Gly Ala Glu Cys Leu Gln Gly Gly
1               5                   10                  15

Gly Gly

<210> SEQ ID NO 117
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 117

Asp Pro Cys Thr Trp Glu Val Trp Gly Lys Glu Cys Leu Gln Gly Gly
1               5                   10                  15

Gly Gly

<210> SEQ ID NO 118
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (10)..(10)
<223> OTHER INFORMATION: Para-guanidino-phenylalanine
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 118

Asp Pro Cys Thr Trp Glu Val Trp Gly Phe Glu Cys Leu Gln Gly Gly
1               5                   10                  15

Gly Gly

<210> SEQ ID NO 119
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 119

Asp Pro Cys Thr Trp Glu Val Trp Gly Ala Glu Cys Leu Gln Gly Gly
1               5                   10                  15

Gly Gly

<210> SEQ ID NO 120
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 120

Asp Pro Cys Thr Trp Glu Val Trp Gly Arg Asp Cys Leu Gln Gly Gly
1               5                   10                  15

Gly Gly

<210> SEQ ID NO 121
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (12)..(12)
<223> OTHER INFORMATION: Homo-Cys
<220> FEATURE:
<221> NAME/KEY: MOD_RES
<222> LOCATION: (17)..(17)
<223> OTHER INFORMATION: Propargylglycine
<220> FEATURE:

```
<223> OTHER INFORMATION: C-term CONH2

<400> SEQUENCE: 121

Asp Pro Cys Thr Trp Glu Val Trp Gly Arg Glu Cys Leu Gln Gly Gly
1               5                   10                  15

Gly Gly

<210> SEQ ID NO 122
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (3)..(3)
<223> OTHER INFORMATION: Homo-Cys
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 122

Asp Pro Cys Thr Trp Glu Val Trp Gly Arg Glu Cys Leu Gln Gly Gly
1               5                   10                  15

Gly Gly

<210> SEQ ID NO 123
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (3)..(3)
<223> OTHER INFORMATION: Homo-Cys
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (12)..(12)
<223> OTHER INFORMATION: Homo-Cys
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 123

Asp Pro Cys Thr Trp Glu Val Trp Gly Arg Glu Cys Leu Gln Gly Gly
1               5                   10                  15

Gly Gly

<210> SEQ ID NO 124
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 124

Asp Pro Cys Thr Trp Glu Val Trp Gly Arg Glu Xaa Leu Gln Gly Gly
1               5                   10                  15

Gly Gly

<210> SEQ ID NO 125
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (3)..(3)
<223> OTHER INFORMATION: Penicillamine
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 125

Asp Pro Xaa Thr Trp Glu Val Trp Gly Arg Glu Cys Leu Gln Gly Gly
1               5                   10                  15

Gly Gly

<210> SEQ ID NO 126
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (3)..(3)
<223> OTHER INFORMATION: Penicillamine
<220> FEATURE:
<221> NAME/KEY: MISC_FEATURE
<222> LOCATION: (3)..(12)
```

<223> OTHER INFORMATION: Disulfide bond
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 126

Asp Pro Xaa Thr Trp Glu Val Trp Gly Arg Glu Xaa Leu Gln Gly Gly
1               5                   10                  15

Gly Gly

<210> SEQ ID NO 127
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (3)..(3)
<223> OTHER INFORMATION: Homo-Cys
<220> FEATURE:
<221> NAME/KEY: MISC_FEATURE
<222> LOCATION: (3)..(12)
<223> OTHER INFORMATION: Disulfide bond
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Propargylglycine
<220> FEATURE:
<223> OTHER INFORMATION: C-term CONH2

<400> SEQUENCE: 127

Asp Pro Cys Thr Trp Glu Val Trp Gly Arg Glu Xaa Leu Gln Gly Gly
1               5                   10                  15

Gly Gly

<210> SEQ ID NO 128
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (4)..(4)
<223> OTHER INFORMATION: Ornithine
<220> FEATURE:
<221> NAME/KEY: MISC_FEATURE
<222> LOCATION: (4)..(13)
<223> OTHER INFORMATION: Lactam bond
<220> FEATURE:
<221> NAME/KEY: MOD_RES
<222> LOCATION: (18)..(18)
<223> OTHER INFORMATION: Propargylglycine
<220> FEATURE:
<223> OTHER INFORMATION: C-term CONH2

<400> SEQUENCE: 128

Gly Asp Pro Xaa Thr Trp Glu Val Trp Gly Arg Glu Asp Leu Gln Gly
1               5                   10                  15

Gly Gly Gly

<210> SEQ ID NO 129
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (4)..(4)
<223> OTHER INFORMATION: Diaminopimelic acid
<220> FEATURE:
<221> NAME/KEY: MISC_FEATURE
<222> LOCATION: (4)..(13)
<223> OTHER INFORMATION: Lactam bond
<220> FEATURE:
<221> NAME/KEY: MOD_RES
<222> LOCATION: (18)..(18)
<223> OTHER INFORMATION: Propargylglycine
<220> FEATURE:
<223> OTHER INFORMATION: C-term CONH2

<400> SEQUENCE: 129

Gly Asp Pro Xaa Thr Trp Glu Val Trp Gly Arg Glu Asp Leu Gln Gly
1               5                   10                  15

Gly Gly Gly

<210> SEQ ID NO 130
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (4)..(13)
<223> OTHER INFORMATION: Lactam bond
<220> FEATURE:
<221> NAME/KEY: MOD_RES
<222> LOCATION: (18)..(18)
<223> OTHER INFORMATION: Propargylglycine
<220> FEATURE:
<223> OTHER INFORMATION: C-term CONH2

<400> SEQUENCE: 130

Gly Asp Pro Lys Thr Trp Glu Val Trp Gly Arg Glu Glu Leu Gln Gly
1               5                   10                  15

Gly Gly Gly

<210> SEQ ID NO 131
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:

```
<221> NAME/KEY: MOD_RES
<222> LOCATION: (4)..(4)
<223> OTHER INFORMATION: Ornithine
<220> FEATURE:
<221> NAME/KEY: MISC_FEATURE
<222> LOCATION: (4)..(13)
<223> OTHER INFORMATION: Lactam bond
<220> FEATURE:
<221> NAME/KEY: MOD_RES
<222> LOCATION: (18)..(18)
<223> OTHER INFORMATION: Propargylglycine
<220> FEATURE:
<223> OTHER INFORMATION: C-term CONH2

<400> SEQUENCE: 131

Gly Asp Pro Xaa Thr Trp Glu Val Trp Gly Arg Glu Glu Leu Gln Gly
1               5                   10                  15

Gly Gly Gly

<210> SEQ ID NO 132
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (4)..(4)
<223> OTHER INFORMATION: Diaminobutyric acid
<220> FEATURE:
<221> NAME/KEY: MISC_FEATURE
<222> LOCATION: (4)..(13)
<223> OTHER INFORMATION: Lactam bond
<220> FEATURE:
<221> NAME/KEY: MOD_RES
<222> LOCATION: (18)..(18)
<223> OTHER INFORMATION: Propargylglycine
<220> FEATURE:
<223> OTHER INFORMATION: C-term CONH2

<400> SEQUENCE: 132

Gly Asp Pro Xaa Thr Trp Glu Val Trp Gly Arg Glu Glu Leu Gln Gly
1               5                   10                  15

Gly Gly Gly

<210> SEQ ID NO 133
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (4)..(4)
<223> OTHER INFORMATION: Diaminopimelic acid
<220> FEATURE:
<221> NAME/KEY: MISC_FEATURE
<222> LOCATION: (4)..(13)
<223> OTHER INFORMATION: Lactam bond
<220> FEATURE:
<221> NAME/KEY: MOD_RES
<222> LOCATION: (18)..(18)
<223> OTHER INFORMATION: Propargylglycine
<220> FEATURE:
<223> OTHER INFORMATION: C-term CONH2

<400> SEQUENCE: 133
```

```
Gly Asp Pro Xaa Thr Trp Glu Val Trp Gly Arg Glu Leu Gln Gly
1               5                   10                  15

Gly Gly Gly

<210> SEQ ID NO 134
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (4)..(13)
<223> OTHER INFORMATION: Lactam bond
<220> FEATURE:
<221> NAME/KEY: MOD_RES
<222> LOCATION: (18)..(18)
<223> OTHER INFORMATION: Propargylglycine
<220> FEATURE:
<223> OTHER INFORMATION: C-term CONH2

<400> SEQUENCE: 134

Gly Asp Pro Asp Thr Trp Glu Val Trp Gly Arg Glu Lys Leu Gln Gly
1               5                   10                  15

Gly Gly Gly

<210> SEQ ID NO 135
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (4)..(13)
<223> OTHER INFORMATION: Lactam bond
<220> FEATURE:
<221> NAME/KEY: MOD_RES
<222> LOCATION: (13)..(13)
<223> OTHER INFORMATION: Ornithine
<220> FEATURE:
<221> NAME/KEY: MOD_RES
<222> LOCATION: (18)..(18)
<223> OTHER INFORMATION: Propargylglycine
<220> FEATURE:
<223> OTHER INFORMATION: C-term CONH2

<400> SEQUENCE: 135

Gly Asp Pro Asp Thr Trp Glu Val Trp Gly Arg Glu Xaa Leu Gln Gly
1               5                   10                  15

Gly Gly Gly

<210> SEQ ID NO 136
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (4)..(13)
```

```
<223> OTHER INFORMATION: Lactam bond
<220> FEATURE:
<221> NAME/KEY: MOD_RES
<222> LOCATION: (13)..(13)
<223> OTHER INFORMATION: Diaminopimelic acid
<220> FEATURE:
<221> NAME/KEY: MOD_RES
<222> LOCATION: (18)..(18)
<223> OTHER INFORMATION: Propargylglycine
<220> FEATURE:
<223> OTHER INFORMATION: C-term CONH2

<400> SEQUENCE: 136

Gly Asp Pro Asp Thr Trp Glu Val Trp Gly Arg Glu Xaa Leu Gln Gly
1               5                   10                  15

Gly Gly Gly

<210> SEQ ID NO 137
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (5)..(14)
<223> OTHER INFORMATION: Lactam bond
<220> FEATURE:
<221> NAME/KEY: MOD_RES
<222> LOCATION: (19)..(19)
<223> OTHER INFORMATION: Propargylglycine
<220> FEATURE:
<223> OTHER INFORMATION: C-term CONH2

<400> SEQUENCE: 137

Gly Gly Asp Pro Glu Thr Trp Glu Val Trp Gly Arg Glu Lys Leu Gln
1               5                   10                  15

Gly Gly Gly Gly
            20

<210> SEQ ID NO 138
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (4)..(13)
<223> OTHER INFORMATION: Lactam bond
<220> FEATURE:
<221> NAME/KEY: MOD_RES
<222> LOCATION: (13)..(13)
<223> OTHER INFORMATION: Ornithine
<220> FEATURE:
<221> NAME/KEY: MOD_RES
<222> LOCATION: (18)..(18)
<223> OTHER INFORMATION: Propargylglycine
<220> FEATURE:
<223> OTHER INFORMATION: C-term CONH2

<400> SEQUENCE: 138

Gly Asp Pro Glu Thr Trp Glu Val Trp Gly Arg Glu Xaa Leu Gln Gly
1               5                   10                  15

Gly Gly Gly
```

```
<210> SEQ ID NO 139
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MISC_FEATURE
<222> LOCATION: (4)..(13)
<223> OTHER INFORMATION: Lactam bond
<220> FEATURE:
<221> NAME/KEY: MOD_RES
<222> LOCATION: (13)..(13)
<223> OTHER INFORMATION: Diaminopimelic acid
<220> FEATURE:
<221> NAME/KEY: MOD_RES
<222> LOCATION: (18)..(18)
<223> OTHER INFORMATION: Propargylglycine
<220> FEATURE:
<223> OTHER INFORMATION: C-term CONH2

<400> SEQUENCE: 139

Gly Asp Pro Glu Thr Trp Glu Val Trp Gly Arg Glu Xaa Leu Gln Gly
1               5                   10                  15

Gly Gly Gly

<210> SEQ ID NO 140
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (17)..(17)
<223> OTHER INFORMATION: Lys-PEG4-DBCO
<220> FEATURE:
<223> OTHER INFORMATION: C-term CONH2

<400> SEQUENCE: 140

Asp Pro Cys Thr Trp Glu Val Trp Gly Arg Glu Cys Leu Gln Gly Gly
1               5                   10                  15

Lys

<210> SEQ ID NO 141
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (17)..(17)
<223> OTHER INFORMATION: Lys-PEG4-DBCO
<220> FEATURE:
<223> OTHER INFORMATION: C-term CONH2

<400> SEQUENCE: 141

Asp Ala Cys Thr Trp Glu Val Trp Gly Arg Glu Cys Leu Gln Gly Gly
1               5                   10                  15
```

Lys

<210> SEQ ID NO 142
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (5)..(5)
<223> OTHER INFORMATION: 2-indanoyl-glycine
<220> FEATURE:
<221> NAME/KEY: MOD_RES
<222> LOCATION: (8)..(8)
<223> OTHER INFORMATION: 5'methoxy Trp
<220> FEATURE:
<221> NAME/KEY: MOD_RES
<222> LOCATION: (17)..(17)
<223> OTHER INFORMATION: Lys-PEG4-DBCO
<220> FEATURE:
<223> OTHER INFORMATION: C-term CONH2

<400> SEQUENCE: 142

Asp Pro Cys Thr Gly Glu Val Trp Gly Arg Glu Cys Leu Gln Gly Gly
1               5                   10                  15

Lys

<210> SEQ ID NO 143
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Lys-PEG4-DBCO
<220> FEATURE:
<223> OTHER INFORMATION: C-term CONH2

<400> SEQUENCE: 143

Asp Pro Xaa Thr Trp Glu Val Trp Gly Arg Glu Xaa Leu Gln Gly Gly
1               5                   10                  15

Lys

<210> SEQ ID NO 144
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)

```
<223> OTHER INFORMATION: Penicillamine
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 144

Asp Ala Xaa Thr Trp Glu Val Trp Gly Arg Glu Xaa Leu Gln Gly Gly
1               5                   10                  15

Lys

<210> SEQ ID NO 145
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (5)..(5)
<223> OTHER INFORMATION: 2-indanoyl-glycine
<220> FEATURE:
<221> NAME/KEY: MOD_RES
<222> LOCATION: (8)..(8)
<223> OTHER INFORMATION: 5'methoxy Trp
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 145

Asp Ala Cys Thr Gly Glu Val Trp Gly Arg Glu Cys Leu Gln Gly Gly
1               5                   10                  15

Lys

<210> SEQ ID NO 146
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (5)..(5)
<223> OTHER INFORMATION: 2-indanoyl-glycine
<220> FEATURE:
<221> NAME/KEY: MOD_RES
<222> LOCATION: (8)..(8)
<223> OTHER INFORMATION: 5'methoxy Trp
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
```

```
<222> LOCATION: (17)..(17)
<223> OTHER INFORMATION: Lys-DBCO
<220> FEATURE:
<223> OTHER INFORMATION: C-term CONH2

<400> SEQUENCE: 146

Asp Pro Xaa Thr Gly Glu Val Trp Gly Arg Glu Xaa Leu Gln Gly Gly
1               5                   10                  15
Lys

<210> SEQ ID NO 147
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (5)..(5)
<223> OTHER INFORMATION: 2-indanoyl-glycine
<220> FEATURE:
<221> NAME/KEY: MOD_RES
<222> LOCATION: (8)..(8)
<223> OTHER INFORMATION: 5'methoxy Trp
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 147

Asp Ala Xaa Thr Gly Glu Val Trp Gly Arg Glu Xaa Leu Gln Gly Gly
1               5                   10                  15
Lys

<210> SEQ ID NO 148
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (17)..(17)
<223> OTHER INFORMATION: Lys-PEG4-DBCO
<220> FEATURE:
<223> OTHER INFORMATION: C-term CONH2

<400> SEQUENCE: 148

Asp Pro Cys Thr Trp Glu Val Trp Gly Arg Glu Cys Leu Gln Gly Gly
1               5                   10                  15
Lys

<210> SEQ ID NO 149
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (17)..(17)
<223> OTHER INFORMATION: Lys-PEG4-DBCO
<220> FEATURE:
<223> OTHER INFORMATION: C-term CONH2

<400> SEQUENCE: 149

Asp Ala Cys Thr Trp Glu Val Trp Gly Arg Glu Cys Leu Gln Gly Gly
1               5                   10                  15

Lys

<210> SEQ ID NO 150
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (5)..(5)
<223> OTHER INFORMATION: 2-indanoyl-glycine
<220> FEATURE:
<221> NAME/KEY: MOD_RES
<222> LOCATION: (8)..(8)
<223> OTHER INFORMATION: 5'methoxy Trp
<220> FEATURE:
<221> NAME/KEY: MOD_RES
<222> LOCATION: (17)..(17)
<223> OTHER INFORMATION: Lys-PEG4-DBCO
<220> FEATURE:
<223> OTHER INFORMATION: C-term CONH2

<400> SEQUENCE: 150

Asp Pro Cys Thr Gly Glu Val Trp Gly Arg Glu Cys Leu Gln Gly Gly
1               5                   10                  15

Lys

<210> SEQ ID NO 151
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Lys-PEG4-DBCO
<220> FEATURE:
<223> OTHER INFORMATION: C-term CONH2

<400> SEQUENCE: 151
```

Asp Pro Xaa Thr Trp Glu Val Trp Gly Arg Glu Xaa Leu Gln Gly Gly
1               5                   10                  15

Lys

<210> SEQ ID NO 152
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (17)..(17)
<223> OTHER INFORMATION: Lys-PEG5-DBCO
<220> FEATURE:
<223> OTHER INFORMATION: C-term CONH2

<400> SEQUENCE: 152

Asp Pro Cys Thr Trp Glu Val Trp Gly Arg Glu Cys Leu Gln Gly Gly
1               5                   10                  15

Lys

<210> SEQ ID NO 153
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 153

Asp Ala Xaa Thr Trp Glu Val Trp Gly Arg Glu Xaa Leu Gln Gly Gly
1               5                   10                  15

Lys

<210> SEQ ID NO 154
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (5)..(5)
<223> OTHER INFORMATION: 2-indanoyl-glycine
<220> FEATURE:
<221> NAME/KEY: MOD_RES
<222> LOCATION: (8)..(8)

-continued

```
<223> OTHER INFORMATION: 5'methoxy Trp
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 154

Asp Ala Cys Thr Gly Glu Val Trp Gly Arg Glu Cys Leu Gln Gly Gly
1               5                   10                  15
Lys

<210> SEQ ID NO 155
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (5)..(5)
<223> OTHER INFORMATION: 2-indanoyl-glycine
<220> FEATURE:
<221> NAME/KEY: MOD_RES
<222> LOCATION: (8)..(8)
<223> OTHER INFORMATION: 5'methoxy Trp
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 155

Asp Pro Xaa Thr Gly Glu Val Trp Gly Arg Glu Xaa Leu Gln Gly Gly
1               5                   10                  15
Lys

<210> SEQ ID NO 156
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (5)..(5)
<223> OTHER INFORMATION: 2-indanoyl-glycine
<220> FEATURE:
<221> NAME/KEY: MOD_RES
<222> LOCATION: (8)..(8)
<223> OTHER INFORMATION: 5'methoxy Trp
<220> FEATURE:
<221> NAME/KEY: MOD_RES
```

```
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 156

Asp Ala Xaa Thr Gly Glu Val Trp Gly Arg Glu Xaa Leu Gln Gly Gly
1               5                   10                  15

Lys

<210> SEQ ID NO 157
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ser Glu Cys Phe Pro Leu Ala Pro Asp Trp Leu Ser Cys Ile Leu
1               5                   10                  15

<210> SEQ ID NO 158
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Asp Pro Cys Thr Trp Glu Val Trp Gly Arg Glu Cys Leu Gln
1               5                   10

<210> SEQ ID NO 159
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Thr Asp Cys Val Ile Phe Gly Leu Glu Thr Tyr Cys Leu Arg
1               5                   10

<210> SEQ ID NO 160
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ser Gly Cys Leu Asp Ala Leu Trp Gln Cys Val Tyr
1               5                   10

<210> SEQ ID NO 161
<211> LENGTH: 14
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 161

Leu Pro Asp Asp Ser Leu Pro Glu Leu Ile Cys Lys Val Arg
1               5                   10

<210> SEQ ID NO 162
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gly Pro Cys Val Leu Ile Arg Asp Tyr Tyr Leu Leu Cys Leu Glu
1               5                   10                  15

<210> SEQ ID NO 163
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Val Leu Cys His Arg Tyr Tyr His Pro Ile Cys Tyr Thr
1               5                   10

<210> SEQ ID NO 164
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Met Phe Cys Phe Arg Trp Tyr Ala Gly Trp Ser Cys Val Ser
1               5                   10

<210> SEQ ID NO 165
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

His Phe Tyr Pro Thr Lys Thr Pro Gly Tyr
1               5                   10

<210> SEQ ID NO 166
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ala Ala Ser Arg Ala Leu Trp Ala Phe Asn Ser Asp
1               5                   10

<210> SEQ ID NO 167

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ser Tyr Tyr Trp Gly Tyr Thr Val Asp Ile Arg Arg
1               5                   10

<210> SEQ ID NO 168
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Lys Thr Cys Val Ser Thr Thr Phe Asp Leu Trp Phe Val Cys Phe Ala
1               5                   10                  15

<210> SEQ ID NO 169
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Tyr His Trp Tyr Gly Tyr Thr Pro Gln Asn Val Ile
1               5                   10

<210> SEQ ID NO 170
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Leu Ala Arg Leu Leu Thr
1               5

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Cys Glu His Gly Ala Met Glu Ile Cys
1               5

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172
```

```
Ala Lys Phe Asn Asp Tyr Trp Arg Trp
1               5
```

<210> SEQ ID NO 173
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

```
Cys Pro Ala Lys Phe Ser Pro Ser Val Cys
1               5                   10
```

<210> SEQ ID NO 174
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

```
Tyr Cys Pro Ile Trp Lys Phe Pro Asp Glu Glu Cys Tyr
1               5                   10
```

<210> SEQ ID NO 175
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (18)..(18)
<223> OTHER INFORMATION: Lys-DBCO
<220> FEATURE:
<223> OTHER INFORMATION: C-term CONH2

<400> SEQUENCE: 175

```
Ser Glu Cys Phe Pro Leu Ala Pro Asp Trp Leu Ser Cys Ile Leu Gly
1               5                   10                  15

Gly Lys
```

<210> SEQ ID NO 176
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (18)..(18)
<223> OTHER INFORMATION: Lys-DBCO
<220> FEATURE:
<223> OTHER INFORMATION: C-term CONH2

<400> SEQUENCE: 176

```
Ser Glu Cys Phe Pro Ala Ala Pro Asp Trp Leu Ser Cys Ile Leu Gly
1               5                   10                  15

Gly Lys
```

```
<210> SEQ ID NO 177
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 177

Asp Pro Cys Thr Trp Glu Val Trp Gly Arg Glu Cys Leu Gln Gly Gly
1               5                   10                  15

Lys

<210> SEQ ID NO 178
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 178

Asp Ala Cys Thr Trp Glu Val Trp Gly Arg Glu Cys Leu Gln Gly Gly
1               5                   10                  15

Lys

<210> SEQ ID NO 179
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 179

Asp Pro Xaa Thr Trp Glu Val Trp Gly Arg Glu Xaa Leu Gln Gly Gly
1               5                   10                  15

Lys
```

```
<210> SEQ ID NO 180
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (5)..(5)
<223> OTHER INFORMATION: 2-indanoyl-glycine
<220> FEATURE:
<221> NAME/KEY: MOD_RES
<222> LOCATION: (8)..(8)
<223> OTHER INFORMATION: 5'methoxy Trp
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 180

Asp Pro Cys Thr Gly Glu Val Trp Gly Arg Glu Cys Leu Gln Gly Gly
1               5                   10                  15

Lys

<210> SEQ ID NO 181
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 181

Asp Ala Xaa Thr Trp Glu Val Trp Gly Arg Glu Xaa Leu Gln Gly Gly
1               5                   10                  15

Lys

<210> SEQ ID NO 182
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (5)..(5)
<223> OTHER INFORMATION: 2-indanoyl-glycine
```

```
<220> FEATURE:
<221> NAME/KEY: MOD_RES
<222> LOCATION: (8)..(8)
<223> OTHER INFORMATION: 5'methoxy Trp
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 182

Asp Ala Cys Thr Gly Glu Val Trp Gly Arg Glu Cys Leu Gln Gly Gly
1               5                   10                  15

Lys

<210> SEQ ID NO 183
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (5)..(5)
<223> OTHER INFORMATION: 2-indanoyl-glycine
<220> FEATURE:
<221> NAME/KEY: MOD_RES
<222> LOCATION: (8)..(8)
<223> OTHER INFORMATION: 5'methoxy Trp
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 183

Asp Pro Xaa Thr Gly Glu Val Trp Gly Arg Glu Xaa Leu Gln Gly Gly
1               5                   10                  15

Lys

<210> SEQ ID NO 184
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (5)..(5)
<223> OTHER INFORMATION: 2-indanoyl-glycine
<220> FEATURE:
<221> NAME/KEY: MOD_RES
<222> LOCATION: (8)..(8)
```

```
<223> OTHER INFORMATION: 5'methoxy Trp
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 184

Asp Ala Xaa Thr Gly Glu Val Trp Gly Arg Glu Xaa Leu Gln Gly Gly
1               5                   10                  15
Lys

<210> SEQ ID NO 185
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (17)..(17)
<223> OTHER INFORMATION: Lys-PEG4-DBCO
<220> FEATURE:
<223> OTHER INFORMATION: C-term CONH2

<400> SEQUENCE: 185

Asp Pro Cys Thr Trp Glu Val Trp Gly Arg Glu Cys Leu Gln Gly Gly
1               5                   10                  15
Lys

<210> SEQ ID NO 186
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (17)..(17)
<223> OTHER INFORMATION: Lys-PEG4-DBCO
<220> FEATURE:
<223> OTHER INFORMATION: C-term CONH2

<400> SEQUENCE: 186

Asp Ala Cys Thr Trp Glu Val Trp Gly Arg Glu Cys Leu Gln Gly Gly
1               5                   10                  15
Lys

<210> SEQ ID NO 187
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
```

```
<222> LOCATION: (5)..(5)
<223> OTHER INFORMATION: 2-indanoyl-glycine
<220> FEATURE:
<221> NAME/KEY: MOD_RES
<222> LOCATION: (8)..(8)
<223> OTHER INFORMATION: 5'methoxy Trp
<220> FEATURE:
<221> NAME/KEY: MOD_RES
<222> LOCATION: (17)..(17)
<223> OTHER INFORMATION: Lys-PEG4-DBCO
<220> FEATURE:
<223> OTHER INFORMATION: C-term CONH2

<400> SEQUENCE: 187

Asp Pro Cys Thr Gly Glu Val Trp Gly Arg Glu Cys Leu Gln Gly Gly
1               5                   10                  15

Lys

<210> SEQ ID NO 188
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Lys-PEG4-DBCO
<220> FEATURE:
<223> OTHER INFORMATION: C-term CONH2

<400> SEQUENCE: 188

Asp Pro Xaa Thr Trp Glu Val Trp Gly Arg Glu Xaa Leu Gln Gly Gly
1               5                   10                  15

Lys

<210> SEQ ID NO 189
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 189
```

-continued

```
Asp Ala Xaa Thr Trp Glu Val Trp Gly Arg Glu Xaa Leu Gln Gly Gly
1               5                   10                  15

Lys

<210> SEQ ID NO 190
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (5)..(5)
<223> OTHER INFORMATION: 2-indanoyl-glycine
<220> FEATURE:
<221> NAME/KEY: MOD_RES
<222> LOCATION: (8)..(8)
<223> OTHER INFORMATION: 5'methoxy Trp
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 190

Asp Ala Cys Thr Gly Glu Val Trp Gly Arg Glu Cys Leu Gln Gly Gly
1               5                   10                  15

Lys

<210> SEQ ID NO 191
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (5)..(5)
<223> OTHER INFORMATION: 2-indanoyl-glycine
<220> FEATURE:
<221> NAME/KEY: MOD_RES
<222> LOCATION: (8)..(8)
<223> OTHER INFORMATION: 5'methoxy Trp
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 191

Asp Pro Xaa Thr Gly Glu Val Trp Gly Arg Glu Xaa Leu Gln Gly Gly
1               5                   10                  15

Lys

<210> SEQ ID NO 192
```

```
-continued

<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (5)..(5)
<223> OTHER INFORMATION: 2-indanoyl-glycine
<220> FEATURE:
<221> NAME/KEY: MOD_RES
<222> LOCATION: (8)..(8)
<223> OTHER INFORMATION: 5'methoxy Trp
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 192

Asp Ala Xaa Thr Gly Glu Val Trp Gly Arg Glu Xaa Leu Gln Gly Gly
1               5                   10                  15

Lys

<210> SEQ ID NO 193
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 193

Asp Ala Xaa Thr Trp Glu Val Trp Gly Arg Glu Xaa Leu Gln Gly Gly
1               5                   10                  15

Lys

<210> SEQ ID NO 194
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: N-term acetyl group
<220> FEATURE:
<221> NAME/KEY: MOD_RES
<222> LOCATION: (17)..(17)
<223> OTHER INFORMATION: Lys-PEG5-DBCO
<220> FEATURE:
<223> OTHER INFORMATION: C-term CONH2

<400> SEQUENCE: 194

Asp Pro Cys Thr Trp Glu Val Trp Gly Arg Glu Cys Leu Gln Gly Gly
1               5                   10                  15
Lys

<210> SEQ ID NO 195
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (5)..(5)
<223> OTHER INFORMATION: 2-indanoyl-glycine
<220> FEATURE:
<221> NAME/KEY: MOD_RES
<222> LOCATION: (8)..(8)
<223> OTHER INFORMATION: 5'methoxy Trp
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 195

Asp Ala Cys Thr Gly Glu Val Trp Gly Arg Glu Cys Leu Gln Gly Gly
1               5                   10                  15
Lys

<210> SEQ ID NO 196
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (5)..(5)
<223> OTHER INFORMATION: 2-indanoyl-glycine
<220> FEATURE:
<221> NAME/KEY: MOD_RES
<222> LOCATION: (8)..(8)
<223> OTHER INFORMATION: 5'methoxy Trp
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 196

Asp Pro Xaa Thr Gly Glu Val Trp Gly Arg Glu Xaa Leu Gln Gly Gly
1               5                   10                  15

Lys

<210> SEQ ID NO 197
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (3)..(3)
<223> OTHER INFORMATION: Penicillamine
<220> FEATURE:
<221> NAME/KEY: MOD_RES
<222> LOCATION: (5)..(5)
<223> OTHER INFORMATION: 2-indanoyl-glycine
<220> FEATURE:
<221> NAME/KEY: MOD_RES
<222> LOCATION: (8)..(8)
<223> OTHER INFORMATION: 5'methoxy Trp
<220> FEATURE:
<221> NAME/KEY: MOD_RES
<222> LOCATION: (12)..(12)
<223> OTHER INFORMATION: Penicillamine
<220> FEATURE:
<221> NAME/KEY: MOD_RES
<222> LOCATION: (17)..(17)
<223> OTHER INFORMATION: Lys-DBCO
<220> FEATURE:
<223> OTHER INFORMATION: C-term CONH2

<400> SEQUENCE: 197

Asp Ala Xaa Thr Gly Glu Val Trp Gly Arg Glu Xaa Leu Gln Gly Gly
1               5                   10                  15

Lys

<210> SEQ ID NO 198
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl group
<220> FEATURE:
<221> NAME/KEY: MOD_RES
<222> LOCATION: (17)..(17)
<223> OTHER INFORMATION: Lys-PEG5-DBCO
<220> FEATURE:
<223> OTHER INFORMATION: C-term CONH2

<400> SEQUENCE: 198

Asp Pro Cys Thr Trp Glu Val Trp Gly Arg Glu Cys Leu Gln Gly Gly
1               5                   10                  15

Lys

<210> SEQ ID NO 199
<211> LENGTH: 14
<212> TYPE: PRT
<213> ORGANISM: Artificial Sequence
<220> FEATURE:
<223> OTHER INFORMATION: Description of Artificial Sequence: Synthetic

```
                                -continued
      peptide

<400> SEQUENCE: 199

Asp Pro Cys Thr Trp Glu Val Trp Gly Arg Glu Cys Leu Gln
1               5                   10

<210> SEQ ID NO 200
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Asp Pro Cys Thr Trp Glu Val Trp Gly Arg Glu Cys Leu Gln Gly Gly
1               5                   10                  15

Lys

<210> SEQ ID NO 201
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ser Glu Cys Phe Pro Leu Ala Pro Asp Trp Leu Ser Cys Ile Leu
1               5                   10                  15
```

THERAPEUTIC NANOPARTICLES HAVING EGFR LIGANDS AND METHODS OF MAKING AND USING SAME

RELATED APPLICATIONS

This application claims priority to and the benefit of U.S. provisional application No. 62/293,609 filed Feb. 10, 2016 and U.S. provisional application No. 62/369,590 filed Aug. 1, 2016, each of which is incorporated in its entirety.

SEQUENCE LISTING

The instant application contains a Sequence Listing which has been submitted electronically in ASCII format and is hereby incorporated by reference in its entirety. Said ASCII copy, created on Feb. 3, 2017, is named BBZ-091PC_SL.txt and is 88,544 bytes in size.

BACKGROUND

Systems that deliver certain drugs to a patient (e.g., targeted to a particular tissue or cell type or targeted to a specific diseased tissue but not normal tissue) or that control release of drugs have long been recognized as beneficial.

For example, therapeutics that include an active drug and that are targeted to a particular tissue or cell type, or targeted to a specific diseased tissue but not to normal tissue, may reduce the amount of the drug in tissues of the body that are not targeted. This is particularly important when treating a condition such as cancer where it is desirable that a cytotoxic dose of the drug is delivered to cancer cells without killing the surrounding non-cancerous tissue. Effective drug targeting may reduce the undesirable and sometimes life threatening side effects common in anticancer therapy. In addition, such therapeutics may allow drugs to reach certain tissues they would otherwise be unable to reach. Therapeutics that offer controlled release and/or targeted therapy also must be able to deliver an effective amount of drug, which is a known limitation in other nanoparticle delivery systems.

For example, a major limitation to traditional cancer treatments is lack of selectivity for cancer cells over healthy cells. Recently, a significant amount of research has been devoted to using nanomedicine to efficiently deliver anticancer agents to tumors. Solid tumors depend on substantial nutrients and oxygen, resulting in exaggerated angiogenesis, which in turn leads to the formation of large gaps between endothelial cells. The leaky vasculature that results leads to size-dependent, e.g. 200-800 nm accumulation of macromolecules and nanoparticles in the tumor. While this form of passive targeting offers an advantage to nanomedicine over free drug, it does not ensure delivery of cargo directly to or into the tumor cell.

Epidermal growth factor receptor (EGFR) is a well understood target that is upregulated in various cancers, has been associated with tumor proliferation, and is generally regarded as a promising receptor for nanotherapeutic targeting. Accordingly, a need exists for targeted nanoparticle therapeutics such as nanoparticles that are capable of targeting EGFR.

SUMMARY

Described herein are polymeric nanoparticles that include a therapeutic agent and an epidermal growth factor receptor targeting ligand, and methods of making and using such therapeutic nanoparticles. In some embodiments, the contemplated nanoparticles may be used to treat cancer.

For example, provided herein is a therapeutic nanoparticle comprising: a therapeutic agent; and a diblock poly(lactic) acid-poly(ethylene)glycol copolymer or a diblock poly(lactic)-co-poly(glycolic) acid-poly(ethylene)glycol copolymer; and a polymer conjugate represented by: PLA-PEG-EGFR ligand wherein the EGFR ligand is bound or associated directly, indirectly, or through a chemical linker to the PEG, and wherein PLA is poly(lactic) acid and PEG is poly(ethylene)glycol.

Further provided herein are pharmaceutically acceptable compositions comprising a plurality of contemplated therapeutic nanoparticles and methods of treating a solid tumor cancer in a patient in need thereof, comprising administering to the patient a therapeutically effective amount of a composition comprising the contemplated therapeutic nanoparticles.

In yet another aspect, a method of identifying targeting ligand-nanoparticle conjugates is provided, comprising: 1) providing azide functionalized PLA-PEG nanoparticles; 2) contacting a potential EGFR ligand with the azide PLA-PEG nanoparticles to form a targeted nanoparticle; 3) screening the targeted nanoparticle for ligand affinity and/or nanoparticle binding; 4) modulating the potential EGFR ligand; and 5) repeating steps 2-4 to obtain a targeted nanoparticle having a desired ligand affinity and/or binding.

BRIEF DESCRIPTION OF THE DRAWINGS

FIG. 9A discloses SEQ ID NO: 201.

FIGS. 21A and 21B depict SPR sensorgrams of 5% $P_{2-2}$ nanoparticle at multiple concentrations. The binding response at each dose, normalized for protein density on the sensor surface, is taken at an end-of-injection time point and plotted against dose. FIG. 21C depicts relative binding of nanoparticles bearing $P_2$ analogs with a single amino acid substitution at 5% ligand density in the presence and absence of EGF as measured by SPR.

FIG. 23C depicts a comparison of EGF, $P_{1-3}$ and $P_{2/55/102}$ nanoparticle binding

DETAILED DESCRIPTION

Figure 1:
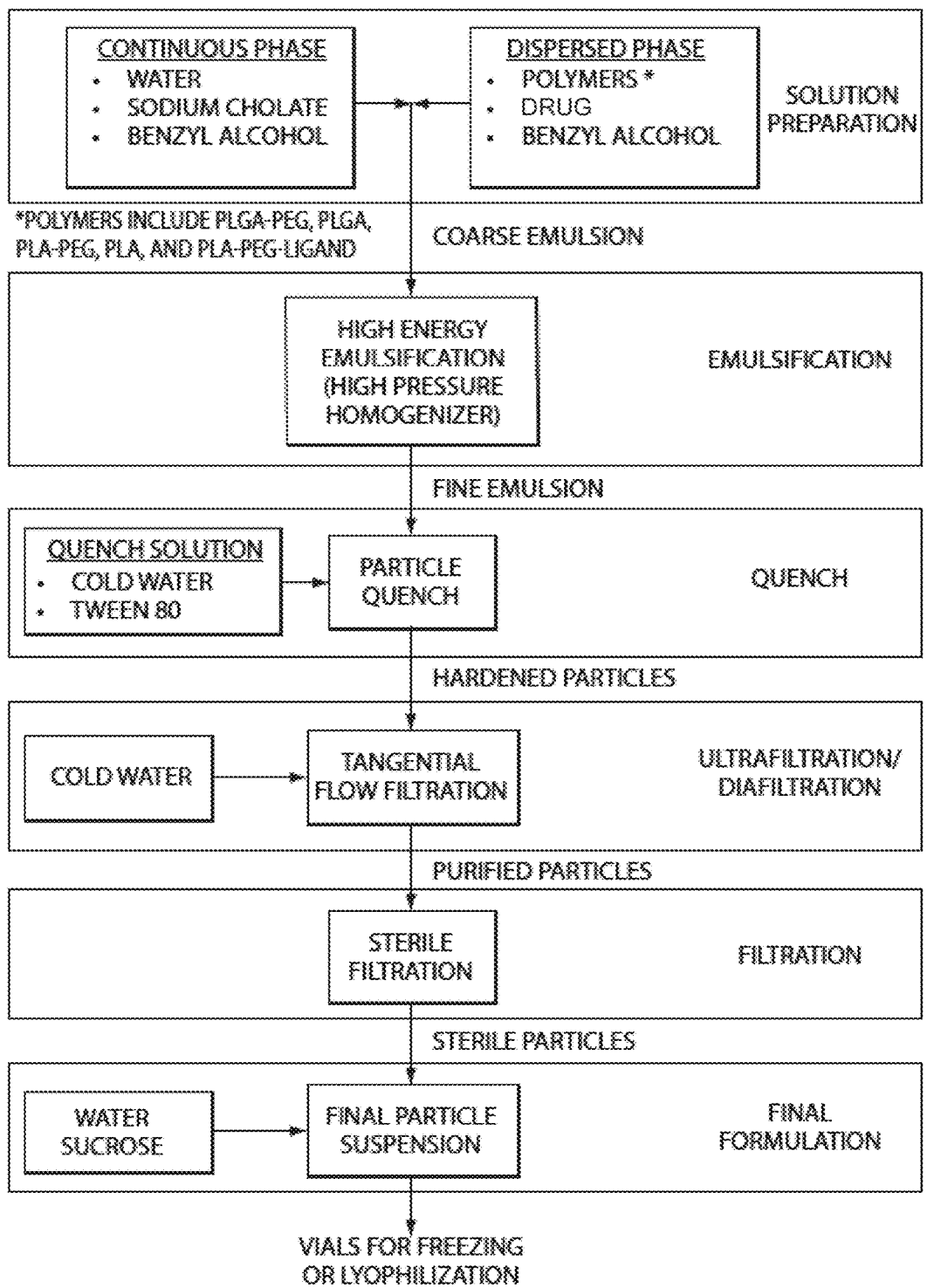
FIG. 1 is flow chart for an emulsion process for forming a disclosed nanoparticle.

Described herein are polymeric nanoparticles that include a therapeutic agent and methods of making and using such therapeutic EGFR ligand and a therapeutic agent that efficiently shuttle across the blood-brain barrier.

Provided herein is a therapeutic nanoparticle that includes a biocompatible polymer; and a polymer conjugate represented by: PLA-PEG-EGFR ligand; wherein the EGFR ligand is covalently bound directly or through a chemical linker to the PEG, and wherein PLA is poly(lactic) acid and PEG is poly(ethylene)glycol; and a therapeutic agent. For example, a disclosed nanoparticle may include about 0.2 to about 10 weight percent of a PLA-PEG-EGFR ligand.

Also provided herein is a therapeutic nanoparticle having a hydrodynamic diameter of the therapeutic nanoparticle comprising a therapeutic agent and about 50 to about 700 PLA-PEG-EGFR ligand molecules and a biocompatible polymer.

Suitable biocompatible polymers are described herein and may be, in some embodiments, selected from the group consisting of diblock poly(lactic) acid-poly(ethylene)glycol copolymer, poly(lactic) acid, diblock poly(lactic-co-glycolic) acid-poly(ethylene)glycol copolymer, poly(lactic-co-glycolic) acid, and mixtures thereof. For example, a contemplated nanoparticle may include a diblock poly(lactic) acid-poly(ethylene)glycol copolymer comprises poly(lactic acid) having a number average molecular weight of about 15 to about 20 kDa and poly(ethylene)glycol having a number average molecular weight of about 4 to about 6 kDa. Disclosed therapeutic nanoparticles may comprise about 10 to about 97 weight percent of a diblock poly(lactic) acid-poly(ethylene)glycol copolymer, or in certain embodiments, about 40 to about 90 weight percent diblock poly(lactic) acid-poly(ethylene)glycol copolymer.

In some embodiments, disclosed PLA-PEG-EGFR ligands include poly(lactic acid)(PLA) having a number average molecular weight of about 15 to about 20 kDa and poly(ethylene)glycol (PEG) having a number average molecular weight of about 4 to about 6 kDa. It is appreciated that the PLA-PEG-EGFR Ligand conjugate may include an acceptable chemical and/or polymeric linker between the PEG and the EGFR Ligand itself. For example, provided herein are nanoparticles having biotin conjugated to PEG using azide functional groups (e.g., through click chemistry), and the targeting construct (EGFR ligand includes an anti-biotin antibody coupled to an EGFR antibody.

For example, a disclosed nanoparticle includes a peptide or antibody ligand such as described herein, effective for targeting or binding to the transferrin receptor (Teri). In certain embodiments, the nanoparticle comprises a certain ratio of ligand-conjugated polymer (e.g., PLA-PEG-EGFR Ligand) to non-functionalized polymer (e.g., PLA-PEG or PLGA-PEG). The nanoparticle can have an optimized ratio of these two polymers such that an effective amount of ligand is associated with the nanoparticle for treatment of a disease or disorder, such as cancer. For example, an increased ligand density may increase target binding (cell binding/target uptake), making the nanoparticle "target specific." Alternatively, a certain concentration of non-functionalized polymer (e.g., non-functionalized PLGA-PEG copolymer) in the nanoparticle can control inflammation and/or immunogenicity (e.g., the ability to provoke an immune response), and allow the nanoparticle to have a circulation half-life that is adequate for the treatment of a disease or disorder. Furthermore, the non-functionalized polymer may, in some embodiments, lower the rate of clearance from the circulatory system via the reticuloendothelial system (RES). Thus, the non-functionalized polymer may provide the nanoparticle with characteristics that may allow the particle to travel through the body upon administration. In some embodiments, a non-functionalized polymer may balance an otherwise high concentration of ligands, which can otherwise accelerate clearance by the subject, resulting in less delivery to the target cells.

In some embodiments, nanoparticles disclosed herein may include functionalized polymers conjugated to an EGFR ligand that constitute approximately 0.1-50, e.g., 0.1-30, e.g., 0.1-20, e.g., 0.1-10, e.g., 0.1-2.5 mole percent of the entire polymer composition of the nanoparticle (e.g., functionalized+non-functionalized polymer).

For example, provided herein are nanoparticles that include approximately 50 to about 1000 ligand associated with (for example, bound directly or indirectly through a linker, or an antibody/anti-antibody association) a polymer (for example PLA-PEG) molecules, for example, about 50 to about 800, about 100 to about 1000, about 200 to about 900, about 500 to about 900, about 600 to about 900 ligand associated polymer molecules. For example, contemplated herein are about 50 to about 800 PLA-PEG-linker-EGFR ligand molecules.

In general, a "nanoparticle" refers to any particle having a diameter (e.g., hydrodynamic diameter) of less than 1000 nm, e.g., about 10 nm to about 200 nm. Disclosed therapeutic nanoparticles may include nanoparticles having a diameter of about 60 to about 120 nm, or about 70 to about 120 nm, or about 80 to about 120 nm, or about 90 to about 120 nm, or about 100 to about 120 nm, or about 60 to about 130 nm, or about 70 to about 130 nm, or about 80 to about 130 nm, or about 90 to about 130 nm, or about 100 to about 130 nm, or about 110 to about 130 nm, or about 60 to about 140 nm, or about 70 to about 140 nm, or about 80 to about 140 nm, or about 90 to about 140 nm, or about 100 to about 140 nm, or about 110 to about 140 nm, or about 60 to about 150 nm, or about 70 to about 150 nm, or about 80 to about 150 nm, or about 90 to about 150 nm, or about 100 to about 150 nm, or about 110 to about 150 nm, or about 120 to about 150 nm. For example, disclosed nanoparticles may have a hydrodynamic diameter of about 50 to about 140 nm, about 60 to 130 nm, about 70 to about 140 nm.

Polymers

In some embodiments, the nanoparticles may comprise a matrix of polymers and a therapeutic agent. In some embodiments, a therapeutic agent and/or targeting moiety (e.g., an EGFR antibody or peptide) can be associated with at least part of the polymeric matrix. For example, in some embodiments, a targeting moiety (e.g., an EGFR ligand) can be covalently associated with the surface of a polymeric matrix. In some embodiments, covalent association is mediated by a linker. The therapeutic agent can be associated with the surface of, encapsulated within, surrounded by, and/or dispersed throughout the polymeric matrix.

A wide variety of polymers and methods for forming particles therefrom are known in the art of drug delivery. In some embodiments, the disclosure is directed toward nanoparticles with at least two macromolecules, wherein the first macromolecule comprises a first polymer bound to a low-molecular weight ligand (e.g., targeting moiety); and the second macromolecule comprising a second polymer that is not bound to a targeting moiety. The nanoparticle can optionally include one or more additional, unfunctionalized, polymers.

Any suitable polymer can be used in the disclosed nanoparticles. Polymers can be natural or unnatural (synthetic) polymers. Polymers can be homopolymers or copolymers comprising two or more monomers. In terms of sequence, copolymers can be random, block, or comprise a combination of random and block sequences. Typically, polymers are organic polymers.

The term "polymer," as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer. In some cases, the polymer can be biologically derived, e.g., a biopolymer. In some cases, additional moieties may also be present in the polymer, for example biological moieties such as those described below. If more than one type of repeat unit is present within the polymer, then the polymer is said to be a "copolymer." It is to be understood that in any embodiment employing a polymer, the polymer being employed may be a copolymer in some cases. The repeat units forming the copolymer may be arranged in any fashion. For example, the repeat units may be arranged in a random order, in an alternating order, or as a block copolymer, i.e., comprising one or more regions each comprising a first repeat unit (e.g., a first block), and one or more regions each comprising a second repeat unit (e.g., a second block), etc. Block copolymers may have two (a diblock copolymer), three (a triblock copolymer), or more numbers of distinct blocks.

Disclosed particles can include copolymers, which, in some embodiments, describes two or more polymers (such as those described herein) that have been associated with each other, usually by covalent bonding of the two or more polymers together. Thus, a copolymer may comprise a first polymer and a second polymer, which have been conjugated together to form a block copolymer where the first polymer can be a first block of the block copolymer and the second polymer can be a second block of the block copolymer. Of course, those of ordinary skill in the art will understand that a block copolymer may, in some cases, contain multiple blocks of polymer, and that a "block copolymer," as used herein, is not limited to only block copolymers having only a single first block and a single second block. For instance, a block copolymer may comprise a first block comprising a first polymer, a second block comprising a second polymer, and a third block comprising a third polymer or the first polymer, etc. In some cases, block copolymers can contain any number of first blocks of a first polymer and second blocks of a second polymer (and in certain cases, third blocks, fourth blocks, etc.). In addition, it should be noted that block copolymers can also be formed, in some instances, from other block copolymers. For example, a first block copolymer may be conjugated to another polymer (which may be a homopolymer, a biopolymer, another block copolymer, etc.), to form a new block copolymer containing multiple types of blocks, and/or to other moieties (e.g., to non-polymeric moieties).

In one set of embodiments, a polymer (e.g., copolymer, e.g., block copolymer) contemplated herein includes a biocompatible polymer, i.e., the polymer that does not typically induce an adverse response when inserted or injected into a living subject, for example, without significant inflammation and/or acute rejection of the polymer by the immune system, for instance, via a T-cell response. Accordingly, the therapeutic particles contemplated herein can be non-immunogenic. The term non-immunogenic as used herein refers to endogenous growth factor in its native state which normally elicits no, or only minimal levels of, circulating antibodies, T-cells, or reactive immune cells, and which normally does not elicit in the individual an immune response against itself Biocompatibility typically refers to the acute rejection of material by at least a portion of the immune system, i.e., a nonbiocompatible material implanted into a subject provokes an immune response in the subject that can be severe enough such that the rejection of the material by the immune system cannot be adequately controlled, and often is of a degree such that the material must be removed from the subject. One simple test to determine biocompatibility can be to expose a polymer to cells in vitro; biocompatible polymers are polymers that typically will not result in significant cell death at moderate concentrations, e.g., at concentrations of 50 micrograms/$10^6$ cells. For instance, a biocompatible polymer may cause less than about 20% cell death when exposed to cells such as fibroblasts or epithelial cells, even if phagocytosed or otherwise uptaken by such cells. Non-limiting examples of biocompatible polymers that may be useful in various embodiments include polydioxanone (PDO), polyhydroxyalkanoate, polyhydroxybutyrate, poly(glycerol sebacate), polyglycolide (i.e., poly(glycolic) acid) (PGA), polylactide (i.e., poly(lactic) acid) (PLA), poly(lactic) acid-co-poly(glycolic) acid (PLGA), polycaprolactone, or copolymers or derivatives including these and/or other polymers.

In certain embodiments, contemplated biocompatible polymers may be biodegradable, i.e., the polymer is able to degrade, chemically and/or biologically, within a physiological environment, such as within the body. As used herein, "biodegradable" polymers are those that, when introduced into cells, are broken down by the cellular machinery (biologically degradable) and/or by a chemical process, such as hydrolysis, (chemically degradable) into components that the cells can either reuse or dispose of without significant toxic effect on the cells. In one embodiment, the biodegradable polymer and their degradation byproducts can be biocompatible.

Particles disclosed herein may or may not contain PEG. In addition, certain embodiments can be directed towards copolymers containing poly(ester-ether)s, e.g., polymers having repeat units joined by ester bonds (e.g., R—C(O)—O—R' bonds) and ether bonds (e.g., R—O—R' bonds). In some embodiments, a biodegradable polymer, such as a hydrolyzable polymer, containing carboxylic acid groups, may be conjugated with poly(ethylene glycol) repeat units to form a poly(ester-ether). A polymer (e.g., copolymer, e.g., block copolymer) containing poly(ethylene glycol) repeat units can also be referred to as a "PEGylated" polymer.

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEGylated polymers and copolymers of lactide and glycolide (e.g., PEGylated PLA, PEGylated PGA, PEGylated PLGA, and derivatives thereof). In some embodiments, polyesters include, for example, polyanhydrides, poly(ortho ester) PEGylated poly(ortho ester), poly(caprolactone), PEGylated poly(caprolactone), polylysine, PEGylated polylysine, poly(ethylene imine), PEGylated poly(ethylene imine), poly(L-lactide-co-L-lysine), poly(serine ester), poly(4-hydroxy-L-proline ester), poly[α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA can be characterized by the ratio of lactic acid:glycolic acid. Lactic acid can be L-lactic acid, D-lactic acid, or D,L-lactic acid. The degradation rate of PLGA can be adjusted by altering the lactic acid-glycolic acid ratio. In some embodiments, PLGA can be characterized by a lactic acid:glycolic acid ratio of approximately 85:15, approximately 75:25, approximately 60:40, approximately 50:50, approximately 40:60, approximately 25:75, or approximately 15:85. In some embodiments, the ratio of lactic acid to glycolic acid monomers in the polymer of the particle (e.g., the PLGA block copolymer or PLGA-PEG block copolymer), may be selected to optimize for various parameters such as water uptake, therapeutic agent release and/or polymer degradation kinetics can be optimized.

It is contemplated that PEG, for example, as part of a PLA-PEG copolymer, may be terminated and include an end group, for example, when PEG is not conjugated to a ligand. For example, PEG may terminate in a hydroxyl, a methoxy or other alkoxyl group, a methyl or other alkyl group, an aryl group, a carboxylic acid, an amine, an amide, an acetyl group, a guanidino group, or an imidazole. Other contemplated end groups include azide, alkyne, maleimide, aldehyde, hydrazide, hydroxylamine, alkoxyamine, or thiol moieties.

Those of ordinary skill in the art will know of methods and techniques for PEGylating a polymer, for example, by using EDC (1-ethyl-3-(3-dimethylaminopropyl) carbodiimide hydrochloride) and NHS (N-hydroxysuccinimide) to react a polymer to a PEG group terminating in an amine, by ring opening polymerization techniques (ROMP), or the like A disclosed particle can for example comprise a diblock copolymer of PEG and PL(G)A, wherein for example, the PEG portion may have a number average molecular weight of about 1,000-20,000, e.g., about 2,000-20,000, e.g., about 2 to about 10,000, (for example about 5 kDa) and the PL(G)A portion may have a number average molecular weight of about 5,000 to about 20,000, or about 5,000-100,000, e.g., about 20,000-70,000, e.g., about 15,000-50,000 (for example, about 16 kDa).

For example, disclosed here is an exemplary therapeutic nanoparticle that includes about 10 to about 99 weight percent poly(lactic) acid-poly(ethylene)glycol copolymer or poly(lactic)-co-poly (glycolic) acid-poly(ethylene)glycol copolymer, or about 20 to about 80 weight percent, about 40 to about 80 weight percent, or about 30 to about 50 weight percent, or about 70 to about 90 weight percent poly(lactic) acid-poly(ethylene)glycol copolymer or poly(lactic)-co-poly (glycolic) acid-poly(ethylene)glycol copolymer. Exemplary poly(lactic) acid-poly(ethylene)glycol copolymers can include a number average molecular weight of about 15 to about 20 kDa, or about 10 to about 25 kDa of poly(lactic) acid and a number average molecular weight of about 4 to about 6, or about 2 kDa to about 10 kDa of poly(ethylene) glycol.

In some embodiments, the poly(lactic) acid-poly(ethylene)glycol copolymer may have a poly(lactic) acid number average molecular weight fraction of about 0.6 to about 0.95, in some embodiments between about 0.7 to about 0.9, in some embodiments between about 0.6 to about 0.8, in some embodiments between about 0.7 to about 0.8, in some embodiments between about 0.75 to about 0.85, in some embodiments between about 0.8 to about 0.9, and in some embodiments between about 0.85 to about 0.95. It should be understood that the poly(lactic) acid number average molecular weight fraction may be calculated by dividing the number average molecular weight of the poly(lactic) acid component of the copolymer by the sum of the number average molecular weight of the poly(lactic) acid component and the number average molecular weight of the poly (ethylene)glycol component.

Disclosed nanoparticles may optionally include about 1 to about 50 weight percent poly(lactic) acid or poly(lactic) acid-co-poly (glycolic) acid (which does not include PEG), or may optionally include about 1 to about 50 weight percent, or about 10 to about 50 weight percent or about 30 to about 50 weight percent poly(lactic) acid or poly(lactic) acid-co-poly (glycolic) acid. For example, poly(lactic) or poly(lactic)-co-poly(glycolic) acid may have a number average molecule weight of about 5 to about 15 kDa, or about 5 to about 12 kDa. Exemplary PLA may have a number average molecular weight of about 5 to about 10 kDa. Exemplary PLGA may have a number average molecular weight of about 8 to about 12 kDa.

A therapeutic nanoparticle may, in some embodiments, contain about 10 to about 30 weight percent, in some embodiments about 10 to about 25 weight percent, in some embodiments about 10 to about 20 weight percent, in some embodiments about 10 to about 15 weight percent, in some embodiments about 15 to about 20 weight percent, in some embodiments about 15 to about 25 weight percent, in some embodiments about 20 to about 25 weight percent, in some embodiments about 20 to about 30 weight percent, or in some embodiments about 25 to about 30 weight percent of poly(ethylene)glycol, where the poly(ethylene)glycol may be present as a poly(lactic) acid-poly(ethylene)glycol copolymer, poly(lactic)-co-poly (glycolic) acid-poly(ethylene) glycol copolymer, or poly(ethylene)glycol homopolymer.

EGFR Ligands

Provided herein are nanoparticles that may include an EGFR ligand. Contemplated EGFR moieties may include small molecules, peptides, or proteins. A targeting moiety can be an antibody, which term is intended to include antibody fragments, characteristic portions of antibodies. Antibody fragments may include scFv, Fv, scFab, Fab, VHH, or F(ab')2. Single chain targeting moieties can be identified, e.g., using procedures such as phage display. Targeting moieties may be a targeting peptide or targeting peptidomimetic with a length of up to about 50 residues or more. A disclosed polymeric conjugate may be formed using any suitable conjugation technique.

EGFR targeting moieties disclosed herein can be, in some embodiments, conjugated to a disclosed polymer or copolymer (e.g., PLA-PEG), and such a polymer conjugate may form part of a disclosed nanoparticle. For example, copper-mediated alkyne-azide cycloaddition chemistry (CuAAC) may be used to conjugate EGFR targeting peptides to PLA-PEG, e.g., to PEG on the surface of the nanoparticles. In another embodiment, strain-promoted azide alkyne cycloaddition (SPAAC) chemistry may be used. For example, a single large batch of PLA-PEG-azide polymer may be synthesized that presents an azide group at the PEG terminus (which may be substantially stable) and on the nanoparticle surface, rather than the targeting ligand itself. Nanoparticles formed with this polymer carry a number of azide groups on the surface of the nanoparticle and may be coupled at various densities to the ligands that have a corresponding strained alkyne functional group. In this way, many targeting ligands may be synthesized at single-digit milligram quantities and screened for binding as nanoparticle conjugates. For example, a more stable azide ($N_3$) group on the polymer excipient and targeting ligands can be functionalized with a reactive dibenzocyclooctyne moiety (DBCO).

An EGFR ligand and a biocompatible polymer (e.g., a biocompatible polymer and a poly(ethylene glycol)) may be conjugated together, in other embodiments, using techniques such as EDC-NHS chemistry (1-ethyl-3-(3-dimethylaminopropyl) carbodiimide hydrochloride and N-hydroxysuccinimide) or a reaction involving a maleimide or a carboxylic acid, which can be conjugated to one end of a thiol, an amine, or a similarly functionalized polyether. The conjugation of a targeting moiety or drug and a polymer to form a polymer-targeting moiety conjugate or a polymer-drug conjugate can be performed in an organic solvent, such as, but not limited to, dichloromethane, acetonitrile, chloroform, dimethylformamide, tetrahydrofuran, acetone, or the like. Specific reaction conditions can be determined by those of ordinary skill in the art using no more than routine experimentation.

In another set of embodiments, a conjugation reaction may be performed by reacting a polymer that comprises a carboxylic acid functional group (e.g., a poly(ester-ether) compound) with a polymer or other moiety (such as a EGFR moiety) comprising an amine. For instance, a targeting moiety may be reacted with an amine to form an amine-containing moiety, which can then be conjugated to the carboxylic acid of the polymer (e.g., PEG). Such a reaction may occur as a single-step reaction, i.e., the conjugation is performed without using intermediates such as N-hydroxysuccinimide or a maleimide. In some embodiments, the EGFR moiety may be reacted with a linker, e.g., an amine-containing linker to form an amine-containing moiety, which can then be conjugated to the carboxylic acid of the polymer as described above. The conjugation reaction between the amine-containing moiety and the carboxylic acid-terminated polymer (such as a poly(ester-ether) compound) may be achieved, in one set of embodiments, by adding the amine-containing moiety, solubilized in an organic solvent such as (but not limited to) dichloromethane, acetonitrile, chloroform, tetrahydrofuran, acetone, formamide, dimethylformamide, pyridines, dioxane, or dimethylsulfoxide, to a solution containing the carboxylic acid-terminated polymer. The carboxylic acid-terminated polymer may be contained within an organic solvent such as, but not limited to, dichloromethane, acetonitrile, chloroform, dimethylformamide, tetrahydrofuran, or acetone. Reaction between the amine-containing moiety and the carboxylic acid-terminated polymer may occur spontaneously, in some cases. Unconjugated reactants may be washed away after such reactions, and the polymer may be precipitated in solvents such as, for instance, ethyl ether, hexane, methanol, or ethanol. In certain embodiments, a conjugate may be formed between an alcohol-containing moiety and carboxylic acid functional group of a polymer, which can be achieved similarly as described above for conjugates of amines and carboxylic acids.

EGFR ligands contemplated herein as, e.g., part of a disclosed nanoparticle, include a peptide comprising a following sequence (or a portion thereof): YHWYGYTPQNVI (SEQ ID NO: 1), LARLLT (SEQ ID NO: 2), CEHGAMEIC (SEQ ID NO: 3), AKFNDYWRW (SEQ ID NO: 4), TDCV- IFGLETYCLR (SEQ ID NO: 5), SGCLDALWQCVY (SEQ ID NO: 6), LPDDSLPELICKVR (SEQ ID NO: 7), GPCV-LIRDYYLLCLE (SEQ ID NO: 8), VLCHRYYHPICYT (SEQ ID NO: 9), MFCFRWYAGWSCVS (SEQ ID NO: 10), HFYPTKTPGY (SEQ ID NO: 11), AASRALWAFNSD (SEQ ID NO: 12), SYYWGYTVDIRRGGK (SEQ ID NO: 13), DPCTWEVWGRECLQ (SEQ ID NO: 14) and SECF-PLAPDWLSCIL (SEQ ID NO: 15). It will be appreciated that EGFR peptides may be modified to include non-natural amino acids, deuterated amino acids, and the like. For example, tryptophan of disclosed sequences can be replaced by phenylalanine, alanine, and/or other natural or non-natural amino acids. In an additional embodiment, EGFR ligands may be modified using a reactive dibenzocyclooctyne moiety (DBCO).

For example, contemplated EGFR ligands include peptides having about 1200-to about 1900 M W. Exemplary modified EGFR peptides comprise a sequence selected from the group consisting of Ac-DPCTWEVWGRECLQGGK (PEG4-DBCO)-CONH2 (SEQ ID NO: 16), Ac-DACTW-EVWGRECLQGGK(PEG4-DBCO)-CONH2 (SEQ ID NO: 17), Ac-DPCT(2Ind)GEV(5MeO)WGRECLQGGK(PEG4-DBCO)-CONH2 (SEQ ID NO: 18), Ac-DPPenTW-EVWGREPenLQGGK(PEG4-DBCO)-CONH2 (SEQ ID NO: 19), AcDAPenTWEVWGREPenLQGGK(DBCO)-CONH2 (SEQ ID NO: 20), Ac-DACT(2Ind)GEV(5MeO)WGRECLQGGK(DBCO)-CONH2 (SEQ ID NO: 21), Ac-DPPenT(2Ind)GEV(5MeO)WGREPenLQGGK(DBCO)-CONH2 (SEQ ID NO: 22), Ac-DAPenT(2Ind)GEV(5MeO)WGREPenLQGGK(DBCO)-CONH2 (SEQ ID NO: 23), Ac-DAPenTWEVWGREPenLQGGK(DBCO)-CONH2 (SEQ ID NO: 24), Ac-DPCTWEVWGRE-CLQGGK(PEG5-DBCO)-CONH2 (SEQ ID NO: 25), Ac-DACT(2Ind)GEV(5MeO)WGRECLQGGK(DBCO)-CONH2 (SEQ ID NO: 26), AcDPPenT(2Ind)GEV(5MeO)WGREPenLQGGK(DBCO)-CONH2 (SEQ ID NO: 27), and AcDAPenT(2Ind)GEV(5MeO)WGREPenLQGGK(DBCO)-CONH2 (SEQ ID NO: 28), or fragments thereof.

In an embodiment, provided herein are nanoparticles having functionalized PLA-PEG (e.g., with azide groups that may be functionalized/coupled (e.g., covalently bound directly or indirectly to an EGFR ligand). Disclosed nanoparticles may include PLA-PEG-functionalized having about 10%, about 20%, about 30% of the total PEG end groups on the surface of the nanoparticle (e.g., about 10% to about 40% functionalized PLA-PEG-azide (with e.g., subsequent conjugation to azide functionalized nanoparticles with a ligand). For example, disclosed nanoparticles may have about 4 to about 12% ligand density (e.g., about 5% or about 10% ligand density, for example, to a lysine side chain at the C-terminus (including a Gly-Gly spacer) and then conjugated to azide nanoparticle. Disclosed nanoparticles may have for example, about 200 to about 500 EGFR ligands or about 225, or about 450 ligands (e.g., about 200 to about 230 ligands or about 400 to about 5000 ligands) per nanoparticle.

Therapeutic Agents

According to the present disclosure, any agents including, for example, therapeutic agents (e.g. anti-cancer agents), diagnostic agents (e.g. contrast agents; radionuclides; and fluorescent, luminescent, and magnetic moieties), prophylactic agents (e.g. vaccines), and/or nutraceutical agents (e.g. vitamins, minerals, etc.) may be delivered by the disclosed nanoparticles. Exemplary agents to be delivered and/or form part of the disclosed nanoparticles, include, but are not limited to, small molecules (e.g., cytotoxic agents), nucleic acids (e.g., siRNA, RNAi, and microRNA agents), proteins (e.g. antibodies), peptides, lipids, carbohydrates, hormones, metals, radioactive elements and compounds, drugs, vaccines, immunological agents, etc., and/or combinations thereof The active agent or drug may be a therapeutic agent such as an antineoplastic such as mTor inhibitors (e.g., sirolimus, temsirolimus, or everolimus), vinca alkaloids such as vincristine, a diterpene derivative or a taxane such as paclitaxel (or its derivatives such as DHA-paclitaxel or PG-paxlitaxel) or docetaxel.

As discussed above, the disclosed nanoparticles may contain a therapeutic agent. Contemplated agents include chemotherapeutic agents, such as taxane agents, kinase inhibitors, and the like. For example, disclosed nanoparticles may include (e.g., a therapeutic agent) one or more of an EGFR kinase inhibitor such as one or more of gefitinib, erlotninb, and/or lapatinib. Also contemplated are nanoparticles containing tyrosine kinase inhibitors such as imatinib, nilotinib, dasatinib, bosutinib, ponatinib, and bafetinib. Any embodiment of the nanoparticles could substitute dasatinib for imatinib, nilotinib, dasatinib, bosutinib, ponatinib, bafetinib, or e.g., any other Bcr-Abl tyrosine-kinase inhibitor.

In one set of embodiments, the therapeutic agent is a drug or a combination of more than one drug. Exemplary combination or solo therapeutic agents include chemotherapeutic agents such as doxorubicin (adriamycin), gemcitabine (gemzar), daunorubicin, procarbazine, mitomycin, cytarabine, etoposide, methotrexate, venorelbine, 5-fluorouracil (5-FU), vinca alkaloids such as vinblastine or vincristine; bleomycin, paclitaxel (taxol), docetaxel (taxotere), cabazitaxel, aldesleukin, asparaginase, busulfan, carboplatin, cladribine, camptothecin, CPT-11, 10-hydroxy-7-ethyl-camptothecin (SN38), dacarbazine, S-I capecitabine, ftorafur, 5'deoxyflurouridine, UFT, eniluracil, deoxycytidine, 5-azacytosine, 5-azadeoxycytosine, allopurinol, 2-chloroadenosine, trimetrexate, aminopterin, methylene-10-deazaaminopterin (MDAM), oxaplatin, picoplatin, tetraplatin, satraplatin, platinum-DACH, ormaplatin, CI-973, JM-216, and analogs thereof, epirubicin, etoposide phosphate, 9-aminocamptothecin, 10,11-methylenedioxycamptothecin, karenitecin, 9-nitrocamptothecin, TAS 103, vindesine, L-phenylalanine mustard, ifosphamidemefosphamide, perfosfamide, trophosphamide carmustine, semustine, epothilones A-E, tomudex, 6-mercaptopurine, 6-thioguanine, amsacrine, etoposide phosphate, karenitecin, acyclovir, valacyclovir, ganciclovir, amantadine, rimantadine, lamivudine, zidovudine, bevacizumab, trastuzumab, rituximab, 5-Fluorouracil, and combinations thereof Non-limiting examples of potentially suitable solo or combination drugs that may form part of a disclosed nanoparticle include anti-cancer agents, including, for example, cabazitaxel, mitoxantrone, and mitoxantrone hydrochloride. In another embodiment, the payload may be an anti-cancer drug such as 20-epi-1, 25 dihydroxyvitamin D3, 4-ipomeanol, 5-ethynyluracil, 9-dihydrotaxol, abiraterone, acivicin, aclarubicin, acodazole hydrochloride, acronine, acylfiilvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizdng morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisazuidinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caraceraide, cabazitaxel, carbetimer, carboplatin, carboxamide-amino-triazole, carboxyamidotriazole, carest M3, carmustine, earn 700, cartilage derived inhibitor, carubicin hydrochloride, carzelesin, casein kinase inhibitors, castanosperrnine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethyhiorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocannycin SA, ebselen, ecomustine, edatrexate, edelfosine, edrecolomab, eflomithine, eflomithine hydrochloride, elemene, elsarnitrucin, emitefur, enloplatin, enpromate, epipropidine, epirubicin, epirubicin hydrochloride, episteride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, flurocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ihnofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatm, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide, lobaplatin, lombricine, lometrexol, lometrexol sodium, lomustine, lonidamine, losoxantrone, losoxantrone hydrochloride, lovastatin, loxoribine, lurtotecan, lutetium texaphyrin lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C uihibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, O6-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazorurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RH retinarnide, RNAi, rogletimide, rohitukine, romurtide, roquinimex, rubiginone Bl, ruboxyl, safingol, safingol hydrochloride, saintopin, sarcnu, sarcophytol A, sargramostim, SDI1 mimetics, semustine, senescence derived inhibitor 1, sense oligonucleotides, signal transduction inhibitors, signal transduction modulators, simtrazene, single chain antigen binding protein, sizofiran, sobuzoxane, sodium borocaptate, sodium phenylacetate, solverol, somatomedin binding protein, sonermin, sparfosafe sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine or vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride.

In an embodiment, a disclosed nanoparticle may include a hydrophobic acid for example, in addition to the active agent. For example, a disclosed nanoparticle may also comprise a hydrophobic acid (such as a fatty acid and/or bile acid) and/or is prepared by a process that includes a hydrophobic acid. In this embodiment, any suitable hydrophobic acid is contemplated, for example, saturated fatty acid such as caproic acid, enanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachidic acid, heneicosanoic acid, behenic acid, tricosanoic acid, lignoceric acid, pentacosanoic acid, cerotic acid, heptacosanoic acid, montanic acid, nonacosanoic acid, melissic acid, henatriacontanoic acid, lacceroic acid, psyllic acid, geddic acid, ceroplastic acid, hexatriacontanoic acid, and combinations thereof Non-limiting examples of unsaturated fatty acids include hexadecatrienoic acid, alpha-linolenic acid, stearidonic acid, eicosatrienoic acid, eicosatetraenoic acid, eicosapentaenoic acid, heneicosapentaenoic acid, docosapentaenoic acid, docosahexaenoic acid, tetracosapentaenoic acid, tetracosahexaenoic acid, linoleic acid, gamma-linolenic acid, eicosadienoic acid, dihomo-gamma-linolenic acid, arachidonic acid, docosadienoic acid, adrenic acid, docosapentaenoic acid, tetracosatetraenoic acid, tetracosapentaenoic acid, oleic acid, eicosenoic acid, mead acid, erucic acid, nervonic acid, rumenic acid, α-calendic acid, β-calendic acid, jacaric acid, α-eleostearic acid, β-eleostearic acid, catalpic acid, punicic acid, rumelenic acid, α-parinaric acid, β-parinaric acid, bosseopentaenoic acid, pinolenic acid, podocarpic acid, palmitoleic acid, vaccenic acid, gadoleic acid, erucic acid, and combinations thereof. In some embodiments, the hydrophobic acid may be a bile acid. Non-limiting examples of bile acids include chenodeoxycholic acid, ursodeoxycholic acid, deoxycholic acid, hycholic acid, beta-muricholic acid, cholic acid, an amino acid-conjugated bile acid, and combinations thereof. An amino-acid conjugated bile acid may be conjugated to any suitable amino acid. In some embodiments, the amino acid-conjugated bile acid is a glycine-conjugated bile acid or a taurine-conjugated bile acid.

Disclosed therapeutic nanoparticles may include about 0.2 to about 25 weight percent therapeutic agent, or for example, about 1 to about 10 weight percent, about 0.5 to about 6 weight percent, about 0.1 to about 3 weight percent, or about 2 to about 12 weight percent of the nanoparticle.

In some embodiments, a therapeutic nanoparticle may include a polymer-drug conjugate. For example, a drug may be conjugated to a disclosed polymer or copolymer (e.g., PLA-PEG), and such a polymer-drug conjugate may form part of a disclosed nanoparticle. For example, a disclosed therapeutic nanoparticle may optionally include about 0.2 to about 30 weight percent of a PLA-PEG or PLGA-PEG, wherein the PEG is functionalized with a drug (e.g., PLA-PEG-Drug).

Pharmaceutical Formulations

Nanoparticles disclosed herein may be combined with pharmaceutically acceptable carriers to form a pharmaceutical composition, according to another aspect. As would be appreciated by one of skill in this art, the carriers may be chosen based on the route of administration as described below, the location of the target issue, the drug being delivered, the time course of delivery of the drug, etc.

The pharmaceutical compositions can be administered to a patient by any means known in the art including oral and parenteral routes. The term "patient," as used herein, refers to humans as well as non-humans, including, for example, mammals, birds, reptiles, amphibians, and fish. For instance, the non-humans may be mammals (e.g., a rodent, a mouse, a rat, a rabbit, a monkey, a dog, a cat, a primate, or a pig). In certain embodiments parenteral routes are desirable since they avoid contact with the digestive enzymes that are found in the alimentary canal. According to such embodiments, compositions may be administered by injection (e.g., intravenous, subcutaneous or intramuscular, intraperitoneal injection), rectally, vaginally, topically (as by powders, creams, ointments, or drops), or by inhalation (as by sprays).

In a particular embodiment, the nanoparticles are administered to a subject in need thereof systemically, e.g., by IV infusion or injection.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In one embodiment, the conjugate is suspended in a carrier fluid comprising 1% (w/v) sodium carboxymethyl cellulose and 0.1% (v/v) TWEEN™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the encapsulated or unencapsulated conjugate is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

It will be appreciated that the exact dosage of a nanoparticle containing a therapeutic agent is chosen by the individual physician in view of the patient to be treated, in general, dosage and administration are adjusted to provide an effective amount of the therapeutic agent nanoparticle to the patient being treated. As used herein, the "effective amount" of a nanoparticle containing a therapeutic agent refers to the amount necessary to elicit the desired biological response. As will be appreciated by those of ordinary skill in this art, the effective amount of a nanoparticle containing a therapeutic agent may vary depending on such factors as the desired biological endpoint, the drug to be delivered, the target tissue, the route of administration, etc. For example, the effective amount of a nanoparticle containing a therapeutic agent might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy.

The nanoparticles may be formulated in dosage unit form for ease of administration and uniformity of dosage. The expression "dosage unit form" as used herein refers to a physically discrete unit of nanoparticle appropriate for the patient to be treated. It will be understood, however, that the total daily usage of the compositions will be decided by the attending physician within the scope of sound medical judgment. For any nanoparticle, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of nanoparticles can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments. The data obtained from cell culture assays and animal studies can be used in formulating a range of dosage for human use.

In some embodiments, a composition suitable for freezing is contemplated, including nanoparticles disclosed herein and a solution suitable for freezing, e.g., a sugar such as a mono, di, or poly saccharide, e.g., sucrose and/or a trehalose, and/or a salt and/or a cyclodextrin solution is added to the nanoparticle suspension. The sugar (e.g., sucrose or trehalose) may act, e.g., as a cryoprotectant to prevent the particles from aggregating upon freezing. For example, provided herein is a nanoparticle formulation comprising a plurality of disclosed nanoparticles, sucrose, an ionic halide, and water; wherein the nanoparticles/sucrose/water/ionic halide is about 3-40%/10-40%/20-95%/0.1-10% (w/w/w/w) or about 5-10%/10-15%/80-90%/1-10% (w/w/w/w). For example, such solution may include nanoparticles as disclosed herein, about 5% to about 20% by weight sucrose and an ionic halide such as sodium chloride, in a concentration of about 10-100 mM. In another example, provided herein is a nanoparticle formulation comprising a plurality of disclosed nanoparticles, trehalose, cyclodextrin, and water; wherein the nanoparticles/trehalose/water/cyclodextrin is about 3-40%/1-25%/20-95%/1-25% (w/w/w/w) or about 5-10%/1-25%/80-90%/10-15% (w/w/w/w).

For example, a contemplated solution may include nanoparticles as disclosed herein, about 1% to about 25% by weight of a disaccharide such as trehalose or sucrose (e.g., about 5% to about 25% trehalose or sucrose, e.g. about 10% trehalose or sucrose, or about 15% trehalose or sucrose, e.g. about 5% sucrose) by weight) and a cyclodextrin such as β-cyclodextrin, in a concentration of about 1% to about 25% by weight (e.g. about 5% to about 20%, e.g. 10% or about 20% by weight, or about 15% to about 20% by weight cyclodextrin). Contemplated formulations may include a plurality of disclosed nanoparticles (e.g. nanoparticles having PLA-PEG and an active agent), and about 2% to about 15 wt % (or about 4% to about 6 wt %, e.g. about 5 wt %) sucrose and about 5 wt % to about 20% (e.g. about 7% wt percent to about 12 wt %, e.g. about 10 wt %) of a cyclodextrin, e.g., HPbCD).

Dynamic light scattering (DLS) may be used to measure particle size, but it relies on Brownian motion so the technique may not detect some larger particles. Laser diffraction relies on differences in the index of refraction between the particle and the suspension media. The technique is capable of detecting particles at the sub-micron to millimeter range. Relatively small (e.g., about 1-5 weight %) amounts of larger particles can be determined in nanoparticle suspensions. Single particle optical sensing (SPOS) uses light obscuration of dilute suspensions to count individual particles of about 0.5 μm. By knowing the particle concentration of the measured sample, the weight percentage of aggregates or the aggregate concentration (particles/mL) can be calculated.

In some embodiments, one or more ionic halide salts may be used as an additional lyoprotectant to a sugar, such as sucrose, trehalose or mixtures thereof. Sugars may include disaccharides, monosaccharides, trisaccharides, and/or polysaccharides, and may include other excipients, e.g. glycerol and/or surfactants. Optionally, a cyclodextrin may be included as a lyoprotectant alone or in addition to other excipients, for example, cyclodextrin may be added in place of an ionic halide salt or sugar. Alternatively, the cyclodextrin may be added in addition to the ionic halide salt and/or sugar.

Suitable ionic halide salts may include sodium chloride, calcium chloride, zinc chloride, or mixtures thereof. Additional suitable ionic halide salts include potassium chloride, magnesium chloride, ammonium chloride, sodium bromide, calcium bromide, zinc bromide, potassium bromide, magnesium bromide, ammonium bromide, sodium iodide, calcium iodide, zinc iodide, potassium iodide, magnesium iodide, or ammonium iodide, and/or mixtures thereof. In one embodiment, about 1 to about 15 weight percent sucrose may be used with an ionic halide salt. A suitable cyclodextrin may include α-cyclodextrin, β-cyclodextrin, γ-cyclodextrin, or mixtures thereof. Exemplary cyclodextrins contemplated for use in the compositions disclosed herein include hydroxypropyl-β-cyclodextrin (HPbCD), hydroxyethyl-β-cyclodextrin, sulfobutylether-β-cyclodextrin, methyl-β-cyclodextrin, dimethyl-β-cyclodextrin, carboxymethyl-β-cyclodextrin, carboxymethyl ethyl-β-cyclodextrin, diethyl-β-cyclodextrin, tri-O-alkyl-β-cyclodextrin, glocosyl-β-cyclodextrin, and maltosyl-β-cyclodextrin. In one embodiment, about 1 to about 25 weight percent trehalose (e.g. about 10% to about 15%, e.g. 5 to about 20% by weight) may be used with cyclodextrin. In one embodiment, the lyophilized pharmaceutical composition may comprise about 1 to about 25 weight percent β-cyclodextrin. An exemplary composition may comprise nanoparticles comprising PLA-PEG-EGFR ligand, an active/therapeutic agent, about 4% to about 6% (e.g. about 5% wt percent) sucrose, and about 8 to about 12 weight percent (e.g. about 10 wt. %) HPbCD.

Methods of Treatment

In some embodiments, targeted nanoparticles may be used to treat, alleviate, ameliorate, relieve, delay onset of, inhibit progression of, reduce severity of, and/or reduce incidence of one or more symptoms or features of a disease, disorder, and/or condition. In some embodiments, targeted nanoparticles may be used to treat cancer, e.g., solid tumor cancers and/or for example, lung cancer (e.g., non-small cell lung carcinoma), anal cancer, and/or glioblastoma multiforme, wherein e.g., the treatment comprises administering an effective amount of certain disclosed nanoparticles. In other embodiments, provided herein are method of treating and/or alemoriating an inflammatory disease (e.g., psoriasis, eczema, and/or atherosclerosis) in a patient in need thereof, comprising administering an effective amount of disclosed nanoparticles.

In one aspect, a method for administering compositions to a subject suffering from cancer or other disclosed indications is provided. The term "cancer" includes pre-malignant as well as malignant cancers. Cancers include, but are not limited to, blood (e.g., chronic myelogenous leukemia, chronic myelomonocytic leukemia, Philadelphia chromosome positive acute lymphoblastic leukemia, mantle cell lymphoma), prostate, gastric cancer, oropharyngeal cancer, cervical cancer, anal cancer, gallbladder cancer, bile duct cancer, cancer of the bowel, colorectal cancer, skin cancer, e.g., melanomas or basal cell carcinomas, lung cancer (e.g., small-cell lung cancer or non-small cell lung cancer (e.g. adenocarcinoma, squamous cell carcinoma)), breast cancer, cancers of the head and neck, bronchus cancer, pancreatic cancer, urinary bladder cancer, brain or central nervous system cancer, tonsillar cancer, peripheral nervous system cancer, esophageal cancer, cancer of the oral cavity or pharynx, liver cancer (e.g., hepatocellular carcinoma), kidney cancer (e.g., renal cell carcinoma), testicular cancer, biliary tract cancer, small bowel or appendix cancer, gastrointestinal stromal tumor, salivary gland cancer, thyroid gland cancer, (e.g., follicular thyroid cancer and undifferentiated thyroid cancer) adrenal gland cancer, osteosarcoma, chondrosarcoma, cancer of hematological tissues, treating cancers with KRas mutations, treating refractory cancers, and the like. "Cancer cells" can be in the form of a tumor (i.e., a solid tumor), exist alone within a subject (e.g., leukemia cells), or be cell lines derived from a cancer. Disclosed nanoparticles, may be used to treat renal cell carcinoma. In another embodiment, disclosed nanoparticles may be used to treat kidney cancer, glioblastoma multiforme, mantle cell lymphoma, or dermal Kaposi's sarcoma.

Cancer can be associated with a variety of physical symptoms. Symptoms of cancer generally depend on the type and location of the tumor. For example, lung cancer can cause coughing, shortness of breath, and chest pain, while colon cancer often causes diarrhea, constipation, and blood in the stool. However, to give but a few examples, the following symptoms are often generally associated with many cancers: fever, chills, night sweats, cough, dyspnea, weight loss, loss of appetite, anorexia, nausea, vomiting, diarrhea, anemia, jaundice, hepatomegaly, hemoptysis, fatigue, malaise, cognitive dysfunction, depression, hormonal disturbances, neutropenia, pain, non-healing sores, enlarged lymph nodes, peripheral neuropathy, and sexual dysfunction. Disclosed nanoparticles may be used to treat the physical symptoms of cancer.

In one aspect, a method for the treatment of cancer (e.g., leukemia) is provided. It should be appreciated that that other methods of treatments, such as infection, inflammation, genetic disorders, etc., can be accomplished as disclosed herein. In some embodiments, the treatment of cancer comprises administering a therapeutically effective amount of disclosed nanoparticles to a subject in need thereof, in such amounts and for such time as is necessary to achieve the desired result. In certain embodiments, a "therapeutically effective amount" of disclosed nanoparticles is that amount effective for treating, alleviating, ameliorating, relieving, delaying onset of, inhibiting progression of, reducing severity of, and/or reducing incidence of one or more symptoms or features of cancer.

In one aspect, a method for administering compositions to a subject suffering from cancer (e.g., leukemia) is provided. In some embodiments, particles may be administered to a subject in such amounts and for such time as is necessary to achieve the desired result (i.e., treatment of cancer). In some embodiments, particles may be administered to a subject in such amounts and for such time as is necessary to achieve the desired result (i.e., remission of cancer). In certain embodiments, a "therapeutically effective amount" of particle disclosed nanoparticle is that amount effective for treating, alleviating, ameliorating, relieving, delaying onset of, inhibiting progression of, reducing severity of, and/or reducing incidence of one or more symptoms or features of an disclosed disorder.

Also contemplated here are methods of treating patients that have been subject to organ transplantation, by administering disclosed nanoparticles. Other methods contemplated herein include methods of treating patients having tuberous sclerosis complex, and/or autism by administering an effective amount of a disclosed nanoparticle.

Methods contemplated herein include, for example, a method of preventing or deterring neointimal hyperplasia in a blood vessel of a patient, for example, a patient receiving a bare metal stent in a lesion of the blood vessel, is disclosed, comprising administering a composition comprising disclosed nanoparticles. Also contemplated herein are methods of treating or preventing restenosis (e.g., in a patient receiving a stent) comprising administering disclosed nanoparticles.

Contemplated methods comprise treating inflammatory diseases, which may be inflammatory bowel disease, such as Crohn's disease, ulcerative colitis, collagenous colitis, lymphocytic colitis, ischemic colitis, diversion colitis, Behcet's disease, or indeterminate colitis. In other embodiments, a method of treating irritable bowel syndrome in a patient in need thereof is provided. The method comprises administering to the patient a therapeutically effective amount of nanoparticles. In some embodiments, the nanoparticles may contain a therapeutic agent. For example, in certain embodiments, the therapeutic agent may be an anti-inflammatory agent, such as described above.

Therapeutic protocols involve administering a therapeutically effective amount of a disclosed nanoparticle to a healthy individual (i.e., a subject who does not display any symptoms of cancer and/or who has not been diagnosed with cancer). For example, healthy individuals may be "immunized" with a disclosed nanoparticle prior to development of cancer and/or onset of symptoms of cancer; at risk individuals (e.g., patients who have a family history of cancer; patients carrying one or more genetic mutations associated with development of cancer; patients having a genetic polymorphism associated with development of cancer; patients infected by a virus associated with development of cancer; patients with habits and/or lifestyles associated with development of cancer; etc.) can be treated substantially contemporaneously with (e.g., within 48 hours, within 24 hours, or within 12 hours of) the onset of symptoms of cancer. Of course individuals known to have cancer may receive treatment at any time.

In other embodiments, disclosed nanoparticles can be used to inhibit the growth of cancer cells, e.g., myelogenous leukemia cancer cells. As used herein, the term "inhibits growth of cancer cells" or "inhibiting growth of cancer cells" refers to any slowing of the rate of cancer cell proliferation and/or migration, arrest of cancer cell proliferation and/or migration, or killing of cancer cells, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, deter the growth, reduce the aggressiveness, or prevent or inhibit metastasis of a cancer in a patient. Those skilled in the art can readily determine, by any of a variety of suitable indicia, whether cancer cell growth is inhibited.

Inhibition of cancer cell growth may be evidenced, for example, by arrest of cancer cells in a particular phase of the cell cycle, e.g., arrest at the G2/M phase of the cell cycle. Inhibition of cancer cell growth can also be evidenced by direct or indirect measurement of cancer cell or tumor size. In human cancer patients, such measurements generally are made using well known imaging methods such as magnetic resonance imaging, computerized axial tomography and X-rays. Cancer cell growth can also be determined indirectly, such as by determining the levels of circulating carcinoembryonic antigen, prostate specific antigen or other cancer-specific antigens that are correlated with cancer cell growth. Inhibition of cancer growth is also generally correlated with prolonged survival and/or increased health and well-being of the subject. Also provided herein are methods of administering to a patient a nanoparticle disclosed herein including an active agent and an EGFR targeting moiety, wherein, upon administration to a patient, such nanoparticles substantially reduces the volume of distribution and/or substantially reduces free $C_{max}$, as compared to administration of the agent alone (i.e., not as a disclosed nanoparticle).

U.S. Pat. No. 8,206,747, issued Jun. 26, 2012, entitled "Drug Loaded Polymeric Nanoparticles and Methods of Making and Using Same" is hereby incorporated by reference in its entirety.

EXAMPLES

The disclosed nanoparticles now being generally described, it will be more readily understood by reference to the following examples which are included merely for purposes of illustration of certain aspects and embodiments, and are not intended to limit the disclosed nanoparticles in any way.

Example 1

Nanoparticle Emulsion Process

Figure 2A:
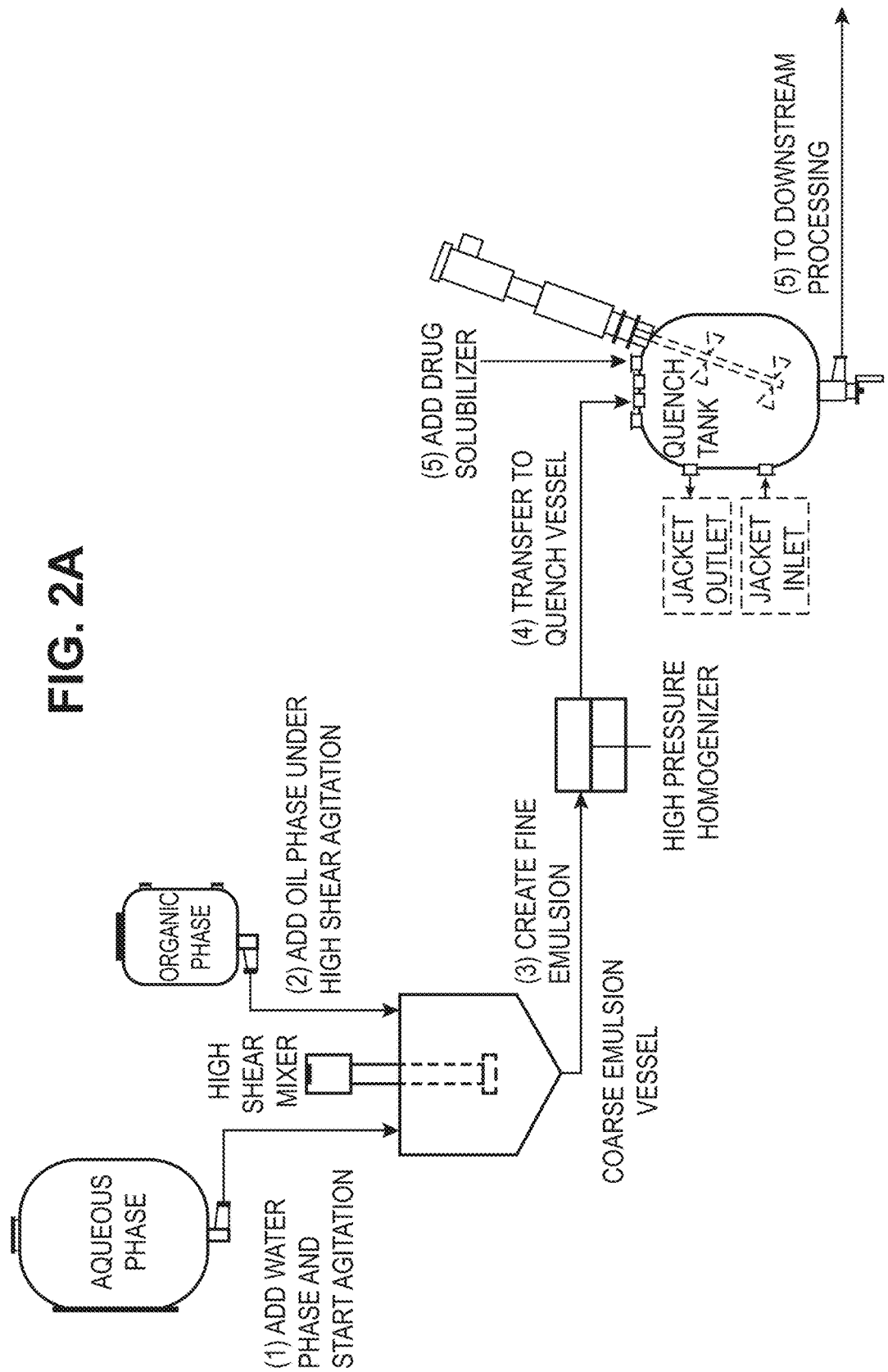
FIG. 2A is a flow diagram for a disclosed emulsion process.
Figure 2B:
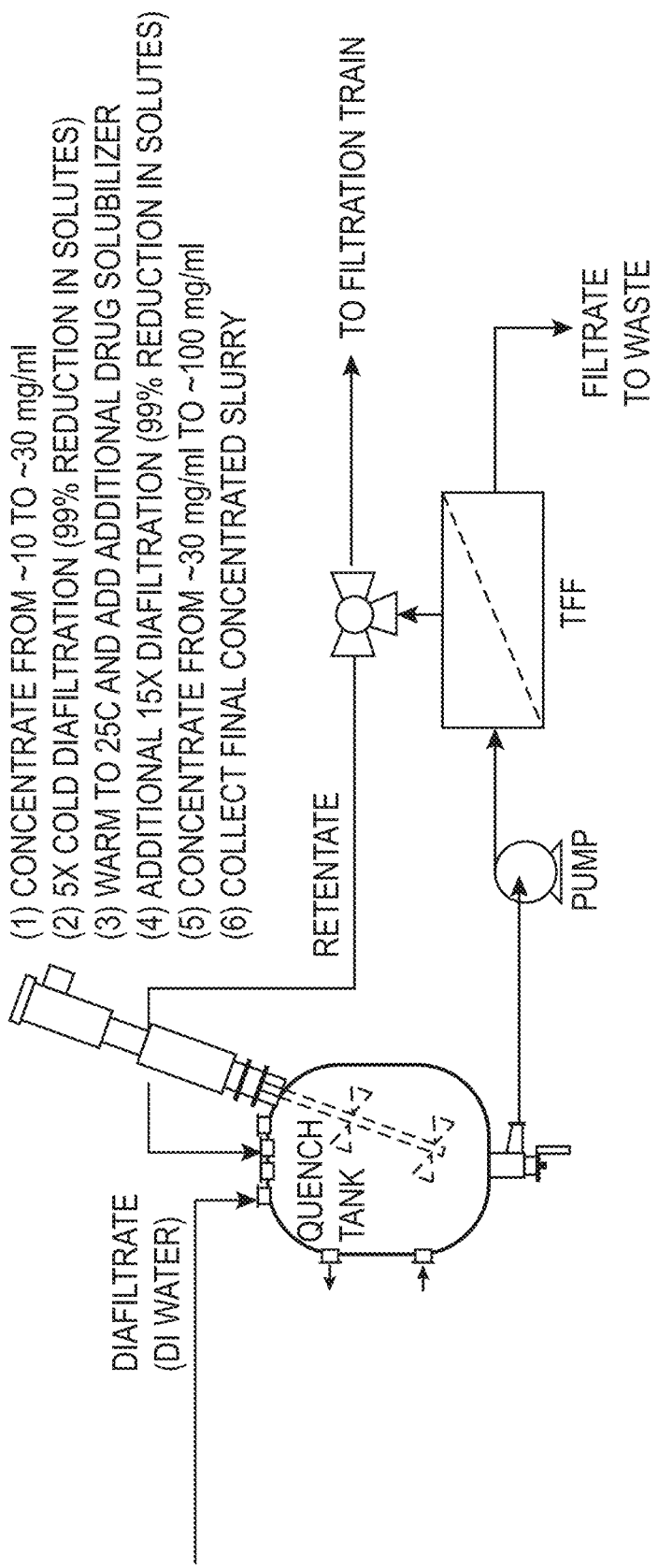
FIG. 2B is a flow diagram for a disclosed emulsion process.

The process described below uses an increase in the solids content of the oil phase. A general flow chart of the process is depicted in FIG. 1, and a process flow diagram is depicted in FIGS. 2A and 2B. By reducing the solvent content of the emulsified oil phase, less drug is lost to the quench fluid when the nanoparticles (NPs) are hardened. A solids and solvent system are chosen to avoid being overly viscous, which may limit the ability to emulsify into ~100 nm droplets. The use of a relatively low molecular weight copolymer (PLA-PEG of ~16 kDa-5 kDa) allows the formulation to remain of low enough viscosity at high solids content. A solvent system is chosen having a suitable solvating power to keep the drug in solution at high concentrations. Use of a co-solvent system (typically 79:21 ethylacetate:benzyl alcohol) allows for a continuous solution up to 50% solids with an 80:20 polymer:active agent blend.

An organic phase is formed composed of a mixture of active agent and polymer (co-polymer and co-polymer with ligand). The organic phase is mixed with an aqueous phase at approximately a 1:5 ratio (oil phase:aqueous phase) where the aqueous phase is composed of a surfactant and some dissolved solvent. In order to achieve high drug loading, about 30% solids in the organic phase is used.

An organic phase is formed composed of a mixture of active agent and polymer (homopolymer, co-polymer, and co-polymer with ligand). Compositions and organic solvents are listed in Table 1. The organic phase is mixed with an aqueous phase at approximately a 1:5 ratio (oil phase: aqueous phase) where the aqueous phase is composed of a surfactant and some dissolved solvent. The primary emulsion is formed by the combination of the two phases under simple mixing or through the use of a rotor stator homogenizer. The primary emulsion is then formed into a fine emulsion through the use of a high pressure homogenizer. The fine emulsion is then quenched by addition to deionized water under mixing. The quench:emulsion ratio is approximately 8.5:1. Then, a solution of 25% (wt %) of Tween 80 is added to the quench to achieve approximately 2% Tween 80 overall. This serves to dissolve free, unencapsulated drug, and makes the nanoparticle isolation process feasible. The nanoparticles are then isolated through either centrifugation or ultrafiltration/diafiltration.

A standard set of nanoemulsion conditions are provided as follows:

TABLE 1

| Targeted Nanoparticle Batch - 30% solids | |
|---|---|
| Attribute | Example value |
| Copolymer (type/amount) | 16/5 PLA-PEG, 40%, with 1 wt % as ligand-PEG-PLA |
| Drug (amount) | 20% |
| Organic solvent (type/amount) | Ethyl acetate (EA), 79% |
| Organic cosolvent (type/amount) | Benzyl alcohol (BA), 21% |

TABLE 1-continued

Targeted Nanoparticle Batch - 30% solids

| Attribute | Example value |
| --- | --- |
| Water phase | 1% sodium cholate, 2% BA, 4% EA in water |
| [solids] in oil phase | 30 wt % |
| Particle size | 114.1 nm |
| Drug load | 11.85% |

Example 2

Materials and Methods

Unless indicated otherwise, the following materials and methods were used for all experiments described in the Examples section herein.

Peptide Synthesis

Peptide synthesis was performed using standard Fmoc/tBu solid phase peptide synthesis (SPPS) on a CEM Liberty Blue microwave assisted, automated peptide synthesizer. All amino acids were obtained from commercial sources (Novabiochem, Anaspec, Bachem, Chem-Impex). Rink amide resin (Novabiochem, San Dieago, Calif.) was used along with the activator N,N'-Diisopropylcarbodiimide (Sigma-Aldrich), Oxyma Pure (Novabiochem) and N,N-Diisopropylethylamine (DIEA) as the base. Removal of the N-terminal Fmoc group was accomplished using 20 vol % piperidine in dimethylformamide (DMF). All peptides were acetylated at the N-terminus and amidated at the C terminus unless otherwise noted. Acetylation was done using a solution of 15 vol % Acetic anhydride (Sigma-Aldrich) in DMF. After the synthesis of the peptides the resin was washed 3 times with 20 mL dichloromethane (DCM) and dried under vacuum. Peptides were cleaved with a solution of 2.5 vol % triisopropylsilane (TIS, Sigma-Aldrich), 2.5 vol % water, 2.5 wt % dithiothreitol (DTT) and 92.5 vol % trifluoroacetic acid (TFA, Alfa Aesar) for 1-2 hours. The resin was filtered off and the TFA solution was concentrated using a flow of nitrogen. The peptide was precipitated from the TFA solution using ~20 volumes of cold diethyl ether, collected by centrifugation and triturated with cold ether (3×, 20 mL each).

Peptide Disulfide Formation

Crude cysteine-containing peptides were oxidized to the corresponding disulfides by dissolving the peptides in 20% DMSO/water at 1 mg/mL and stirring at room temperature. Reactions were monitored by LC/MS. Upon completion the crude peptide was isolated using solid phase extraction (2 g Sep-Pak tC18 cartridges, Waters) and lyophilized to dryness. Peptides were dissolved in water/acetonitrile and purified by reverse phase HPLC using a 250×21.2 mm C18 column (Phenomenex) with an acetonitrile/water gradient containing 0.1% TFA. Pure fractions were pooled and lyophilized and determined to be >90% pure by LCMS. Correct peptide structure was confirmed using electrospray mass spectrometry. All peptides reported herein had expected m/z values.

Lactam Formation

In order to ensure site specific lactam formation we used methyltrityl (Mtt) and 2-phenylisopropyl oxy (O-2PhiPr) protecting groups that can be removed using a mild acid cleavage leaving the other side chains protected and the peptide attached to the solid support. A mixture of 94% DCM, 5% TIS and 1% TFA was run slowly through the resin. The release of the protecting groups can be observed as the free Mtt has a strong, yellow/orange colour. The cleavage solution is run through the resin until a yellow colour is observed, and then recedes again. The resin is washed with DCM (20 mL, 3×) and DMF (20 mL, 3×). Next, the resin is soaked on 20 mL DMF followed by the addition of PyBOP (3 equiv.) and DIEA (9 equiv.). The solution is allowed to rock for six hours and then washed with DCM (20 mL, 3×) and cleaved as described above.

$P_2$-Biotin Dimer Synthesis $P_2$-Biotin dimer was synthesized using Fmoc-PEG Biotin NovaTag resin (Novabiochem). The peptide was cleaved and oxidized as reported above and dimerized via the free amine of the lysine residue using BS(PEG)5 (PEGylated bis(sulfosuccinimidyl)suberate) (ThermoFisher Scientific). The dimerization reaction was performed in DMF with DIEA as base (6 equivalents) and then diluted into water and purified by RP-HPLC to yield the $P_2$-Biotin-dimer. This reagent was used in the $P_2$ competition ELISA. The expected MW was 5167.9, the deconvoluted Mass: 5167.6, and the ions observed were 1292.9 and 1723.5.

Typical Procedure for DBCO Conjugation to Peptides

Crude peptides were conjugated to DBCO for copper free click chemistry post disulfide oxidation (if applicable). $P_1$ (22.96 mg, 11.88 μmop was dissolved in 1.2 mL dry DMF. DBCO-PEG5-NHS ester (12.4 mg, 17.8 μmol, 1.5 equivalents) was dissolved in 0.3 mL of dry DMF and added to the peptide solution followed by the addition of N,N-Diisopropylethylamine (12.4 uL, 71.3 μmol, 6 equivalents). The reaction was allowed to stir for one hour while being monitored by LCMS. After one hour the starting material was consumed and the product was purified via RP-HPLC using acetonitrile (0.1% TFA) and water (0.1% TFA).

Intact Mass Measurements of Peptides by LC-MS

Samples were injected onto a C18 Jupiter© column (250×2 mm, 5 μm, 300 Å, Phenomenex) with an Agilent 1200 HPLC, using acetonitrile (0.02% TFA, 0.08% formic acid) and water (0.02% TFA, 0.08% formic acid) as mobile phase at 0.5 mL/min. The method was a linear gradient from 5% to 75% acetonitrile over 10 min, with the peptides eluting within the range 3-10 min and being directed to the Agilent 6220 TOF. Electrospray conditions consisted of a gas temperature at 350° C., capillary voltage at 3500 V, and fragmentor at 120 V. The m/z mass range was 100-3000 Da. Acquisition software was MassHunter (Agilent).

Synthesis of DBCO-Aldehyde Linker

DBCO-PEG4-Amine (19.24 mg, 0.037 mmol) was dissolved in DMF (700 uL) followed by the addition of p-Formylbenzoic acid N-hydroxysuccinimide ester (9.1 mg, 0.037 mmol) and DIEA (38.4 uL, 0.22 mmol). The reaction was allowed to stir at room temperature for 3 hours after which it was shown to be complete by LCMS. The crude product was purified by RP-HPLC and the pure product was lyophilized to give 11.3 mg of pure product (47% yield). The expected MW was 655.75, and the observed MW+1=656.296.

Reductive Alkylation of EGF

Recombinant human EGF (R&D systems) was conjugated to DBCO-Aldehyde using a method similar to one previously reported. A solution of EGF (6.4 mg, 7.95 mL, 0.806 mg/ml in PBS) was combined with 1 mL of sodium acetate buffer (500 mM, pH 5.5). DBCO-Aldehyde (9.92 mg, 15 equiv.) was dissolved in 950 uL of DMF and added to the EGF solution. The reaction was allowed to stir for 30 min followed by the addition of sodium cyanoborohydride (100 uL, 1 M in THF) to give a final concentration of 10 mM. The reaction was allowed to stir at room temperature overnight. The reaction was monitored by LCMS and was determined complete when approximately 70% conversion to the desired product was detected by UV (expected MW 6986.92, observed MW 6986.9). The reaction mixture was concentrated using an Amicon Ultra 5K Centrifugal Filter Device (EMD Millipore) and the desired product was purified via a Zeba Spin Column, 7K MWCO (ThermoFisher). The concentration of the final product was determined by UV analysis. The integrity of the DBCO moiety was tested by reaction with 10 equivalents of 4-azidoaniline hydrochloride. Complete reaction of the EGF-DBCO with azidoaniline was observed by LCMS (expected MW 7121.06, observed MW 7120.85).

Synthesis of PLA-PEG-Azide

Commercially available α-Hydroxy-ω-azido-polyethylene glycol (HO-PEG-azide, Rapp Polymere) was used as a macro-initiator in the ring opening polymerization of D,L-lactide using Tin (II) 2-ethylhexanoate as a catalyst under monomer melt condition at 130° C. The resulting PLA-PEG-azide was dissolved in dichloromethane and then recovered by precipitation into methyl tert-butyl ether (MTBE) and heptane (70/30 v/v).

Synthesis of PLA-Cy5

10 kDa PLA-COOH (1 gram, 0.1 mmol) was dissolved in 10 mL DMSO for a final concentration of 100 mg/mL. To this was added Cy5-Amine (0.058 g, 0.1 mmol), PyBOP (0.052 g, 0.1 mmol), and DIEA (0.087 mL, 0.5 mmol). The coupling reaction was monitored by LCMS and upon completion the polymer product was purified by precipitation in 20% heptane in MBTE. The resulting blue solid was filtered off and washed with 20% heptane in MTBE.

Nanoparticle Preparation

A general emulsion procedure for the preparation of PLA-Cy5 loaded nanoparticles in aqueous suspension is as follows: An organic phase was formed composed of 20% solids (wt %) including 19.8% polymer and 0.2% PLA-Cy5. The organic solvents are ethyl acetate (EA) and benzyl alcohol (BA), where BA comprises 20% (wt %) of the organic phase. The organic phase was mixed with an aqueous phase at approximately a 1:5 ratio (organic phase: aqueous phase) where the aqueous phase was composed of 0.25% sodium cholate, 2% BA, and 4% EA (wt %) in water. The primary emulsion was formed by the combination of the two phases under simple mixing or through the use of a rotor stator homogenizer. The primary emulsion was then formed into a fine emulsion through the use of a high pressure homogenizer. The fine emulsion was then quenched by addition to chilled (0-5° C.) deionized water under mixing. The quench:emulsion ratio was approximately 10:1. Then, a solution of 35% (wt %) of Tween-80 was added to the quench to achieve approximately 4% Tween-80 overall. The nanoparticles were isolated and concentrated through ultra-filtration/diafiltration.

Polymer Characterization

The number average molecular weight, weight average molecular weight, and the polydispersity index of the polymers were determined by size exclusion chromatograph on a Tosoh Biosciences EcoSEC (Model HLC-8320GPC). The samples were injected (10 uL, 1 mg/mL) onto a TSKgel Column (4.6mmx15 cm, 3 um, Tosoh Biosciences #W00013) and run at 0.25 mL/min at 35° C.

Nanoparticle Size Analysis

The particle size distribution was determined by dynamic light scattering (DLS) of a dilute aqueous suspension at 25° C. on a Wyatt DynaPro plate reader with a 830 nm laser scattered at 158°. The particle size analysis was performed in triplicate and the average value for mean particle diameter is reported. For all samples, the standard deviation of the triplicate measurements was ≤3 nm.

Zeta Potential Analysis

Zeta potential was determined on Brookhaven Instruments, PALS Zeta Potential Analyzer. The samples were diluted into 1 mM NaCl solution to a final concentration of ~1 mg/mL of nanoparticles. 1.7 mL of each sample was added to a cuvette; each cuvette was placed into the Brookhaven ZetaPlus and then allowed to equilibrate to 25° C. for 5 minutes before taking the measurement.

ELISA

Recombinant human EGFR (5 µg/mL, R&D Systems) was captured on 96-well plates in 0.1 M carbonate/bicarbonate buffer (Sigma-Aldrich) at 4° C. overnight. Plates were blocked for 2 h with 2% BSA in PBS at RT. For EGFR-targeted peptides and nanoparticles known to compete with EGF for EGFR binding, serial dilutions of peptides and nanoparticles, (targeted and non-targeted) were incubated with 0.7 nM biotinylated recombinant human EGF (Molecular Probes) in assay buffer (2% BSA, 0.05% Tween-20 in PBS) for 90 min at RT. For peptides and targeted nanoparticles derived from the $P_2$ ligand, serial dilutions of peptides and nanoparticles (targeted and non-targeted) were incubated with 1 nM $P_2$-Biotin dimer and 50 nM recombinant human EGF (R&D Systems) in assay buffer for 90 min at RT. Plates were washed three times with PBS containing 0.05% Tween-20 (PBS-T) and then incubated with a 1:10,000 dilution of streptavidin-HRP (Thermo Fisher Scientific) diluted in assay buffer for 90 min at RT. Plates were washed an additional three times with PBS-T, and then incubated with TMB substrate (BioFx) for 15 min at RT. Reactions were stopped with stop solution (BioFx) and absorbance was read at 450 nm in a microplate reader (SpectraMax M5e, Molecular Devices).

Screening ELISA

A different format of the EGFR-binding ELISA was developed to screen peptides reported to compete with EGF. As with the previously described ELISA method, recombinant human EGFR (5 µg/mL, R&D Systems) was captured on 96-well plates in 0.1 M carbonate/bicarbonate buffer (Sigma-Aldrich) at 4° C. overnight. Plates were blocked for 2 h with 2% BSA in PBS at RT. Peptides were incubated at one concentration, 100 uM, with 0.7 nM biotinylated recombinant human EGF (Molecular Probes) in assay buffer (2% BSA, 0.05% Tween-20 in PBS) for 90 min at RT. Peptides were reconstituted as 100% DMSO stocks, resulting in a final concentration of DMSO in the assay of 2% for all samples. Plates were washed three times with PBS containing 0.05% Tween-20 (PBS-T) and then incubated with a 1:10,000 dilution of streptavidin-HRP (Piece) diluted in assay buffer for 90 min at RT. Plates were washed an additional three times with PBS-T, and then incubated with TMB substrate (BioFx) for 15 min at RT. The reaction was stopped with stop solution (BioFx) and absorbance was read at 450 nm in a microplate reader (SpectraMax M5e, Molecular Devices).

Cell Culture

Human epidermoid carcinoma cell line A431 (ATCC) that overexpresses EGFR was cultured in RPMI media, supplemented with 10% fetal bovine serum (FBS) and 100 Units/mL penicillin-streptomycin (all tissue culture reagents from Thermo Fisher Scientific), at 37° C. in 5% CO2 atmosphere.

Surface Binding

Cultured A431 cells were resuspended in 5% BSA in PBS at $2\times10^6$ cells/mL. Serially diluted targeted and non-targeted Cy5 conjugated nanoparticles were incubated with A431 cells in V-bottom 96-well plates for 1 h at 4° C. Samples were washed three times with ice cold PBS to remove unbound nanoparticles, and resuspended in ice cold PBS. Samples were analyzed on an Accuri C6 flow cytometer (BD Biosciences).

Internalization Assay

Cultured A431 cells were resuspended in 5% BSA in PBS at $2\times10^6$ cells/mL as in surface binding assay. Serially diluted targeted and non-targeted Cy5 conjugated nanoparticles were incubated with A431 cells in V-bottom 96-well plates for various times at 37° C. Samples were washed three times with ice cold PBS to remove unbound nanoparticles. Half of each sample was resuspended in ice cold PBS and analyzed on the Accuri C6 to generate the surface-bound nanoparticle fluorescence. The remaining half of the sample was treated with 0.2 M acetic acid and 0.5 M NaCl acid wash buffer for 5 minutes. Samples were then centrifuged and resuspended in ice cold PBS, and analyzed for retained fluorescence on the Accuri C6.

SPR

Surface plasmon resonance (SPR) binding studies were carried out on a Biacore T200 instrument (GE Healthcare). Approximately 10,000 RU of anti-Fc antibody (GE Healthcare, Cat# BR100839) was immobilized via amine coupling on each of flow cells 1 and 2 of a CM5 dextran-coated gold sensor chip (GE Healthcare, Cat# BR100530). Fc tagged recombinant human EGFR (rhEGFR-Fc, R&D systems, Cat#344-ER-050) was reconstituted at 10 µg/mL in PBS and captured on flow cell 2. The contact time and resulting amount of rhEGFR-Fc capture was varied based on the nature of the analyte, namely whether it was a peptide or nanoparticle. When testing the binding of analytes in the presence of EGF, a solution of rhEGF (R&D Systems, Cat#236-EG) in PBS was pre-injected over the rhEGFR-Fc before introducing the analyte.

Peptide binding assays were carried out in 10 mM PBS buffer supplemented with 0.05% surfactant P20 and 5% DMSO by volume, at 25° C. Peptides were injected over the rhEGFR-Fc surface for 60 s, followed by dissociation (buffer injection) for 60 s and regeneration with a 10 s pulse of 3M $MgCl_2$. A fresh rhEGFR-Fc surface was generated for each concentration of each peptide tested. Peptide binding data was analyzed by fitting to a 1:1 Langmuir kinetic model to obtain the on-rate ($k_a$), off-rate ($k_d$) and/or equilibrium binding constant (KD) of the interaction.

Nanoparticle binding assays were carried out in 10 mM HBS-EP+ buffer (GE Healthcare, Cat# BR100669) at 25° C. Nanoparticles were injected over the rh EGFR-Fc surface for 60 s, followed by dissociation for 60 s and regeneration with a 10 s pulse of 3M $MgCl_2$. A fresh rhEGFR-Fc surface was generated for each concentration of each nanoparticle tested. Nanoparticle sensograms could not be fit accurately to the 1:1 Langmuir kinetic model due to the multivalent nature of the binding interaction between nanoparticle and target. Instead, nanoparticle binding data was presented as a plot of binding response vs. concentration at a single time point after the injection end.

In Vitro Release Kinetics of Cy5

PLA-Cy5 release kinetics were determined in vitro under physiological sink conditions. Nanoparticles were suspended in 10% polysorbate 20 in phosphate buffered saline (PBS), and incubated with mild agitation in a 37° C. water bath. Periodically, an aliquot of the suspension was removed and ultracentrifuged at 264,000 g for 30 minutes. Samples of the supernatant and the suspension prior to ultracentrifugation were analyzed by fluorescence (ex 650 nm, em 670 nm), and the percent release was calculated by comparing the released PLA-Cy5 concentration in the supernatant with the total concentration in the uncentrifuged sample.

Example 3

Click Chemistry-enabled Nanoparticles

In clinical development and large-scale manufacturing, receptor-targeted nanoparticles are produced by incorporation of a targeting polymer comprising PLA-PEG covalently conjugated at the PEG terminus to a low molecular weight targeting ligand. During the nanoemulsion manufacturing process, the targeting ligand is oriented to the surface of the nanoparticle along with the hydrophilic PEG chains. While the synthesis of targeting polymers is desirable for large scale nanoparticle production, it can require hundreds of milligram to gram quantities of targeting ligand and a significant chemistry effort that may preclude the evaluation of larger numbers of molecules. We have therefore developed a surface conjugation strategy that enables a more rapid and ligand-efficient screening of different targeting molecules conjugated to nanoparticles.

To enable nanoparticle surface conjugation, we explored various chemistries that were orthogonal to the functional groups found in most targeting ligands, compatible with aqueous suspensions of nanoparticles, and that would be stable to long-term storage of nanoparticle stocks. While copper-mediated alkyne-azide cycloaddition chemistry (CuAAC) initially appeared a promising strategy, this approach was found to be inconsistently compatible with the variety of ligands that were typically being screened (small molecules, peptides, proteins), despite evaluation of several reaction conditions. In some cases reactions did not proceed efficiently, and in other cases significant ligand based impurities were formed during the reaction. The potential for ligand degradation is exacerbated by the fact that characterization of molecular structure post-conjugation is a significant challenge, and thus this chemistry was considered unsuitable for evaluation of receptor-targeted nanoparticles.

The most reliable and efficient chemistry was the strain-promoted azide alkyne cycloaddition (SPAAC). In this approach, a single large batch of PLA-PEG-azide polymer was synthesized that presents the azide group at the PEG terminus which is subsequently presented on the nanoparticle surface. Nanoparticles that incorporate this polymer carry a number of azide groups on the surface and may be coupled at various densities to the ligands that contain a corresponding strained alkyne functional group. We selected dibenzocyclooctyne (DBCO) due to its balance of reactivity and stability, its water solubility, and its commercial availability. In this way, many targeting ligands may be synthesized at single-digit milligram quantities and screened for binding as nanoparticle conjugates.

Figures 3A, 3B:
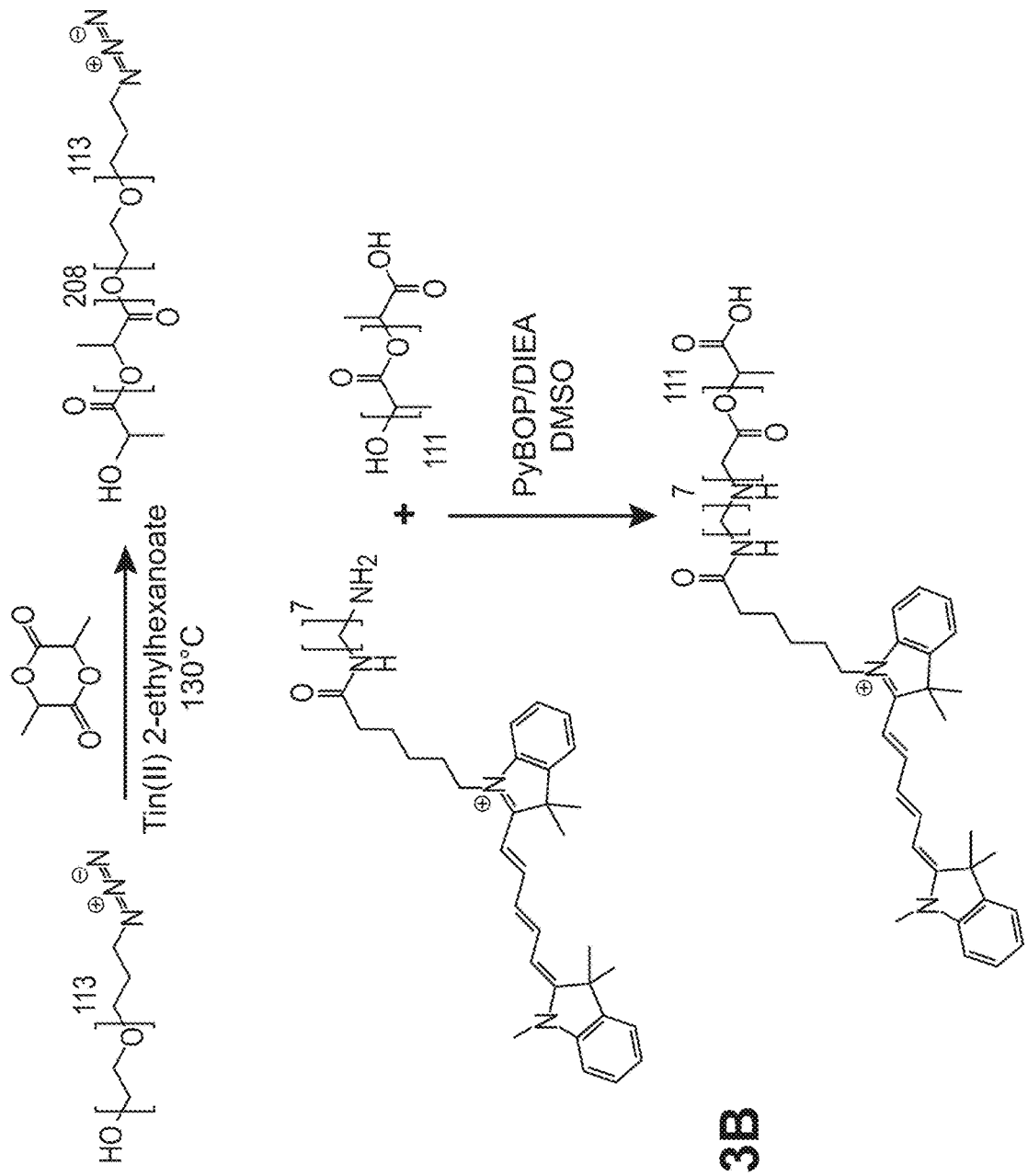
FIG. 3A depicts the synthesis of polymer component PLA-PEG-azide from commercially available HO-PEG-azide.
FIG. 3B depicts the synthesis of polymer PLA-Cy5 fluorescent payload.
Figure 4A:
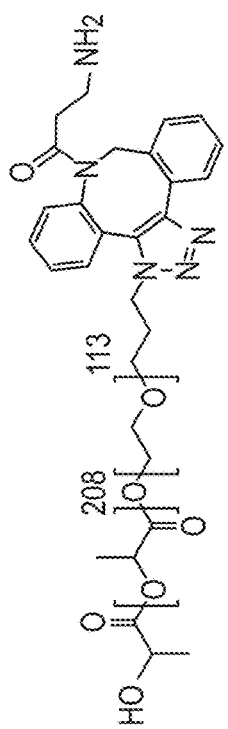
FIGS. 4A-4C depict conjugation of DBCO-amine to PLA-PEG-azide (FIG. 4A), liquid chromatography-mass spectrometry (LCMS) analysis of click reaction demonstrating 99% consumption of DBCO amine when reacted with PLA-PEG-azide (FIG. 4B), and LCMS analysis of click reaction demonstrating 98% consumption of DBCO amine when applied to azide nanoparticles (FIG. 4C).
Figure 4A:
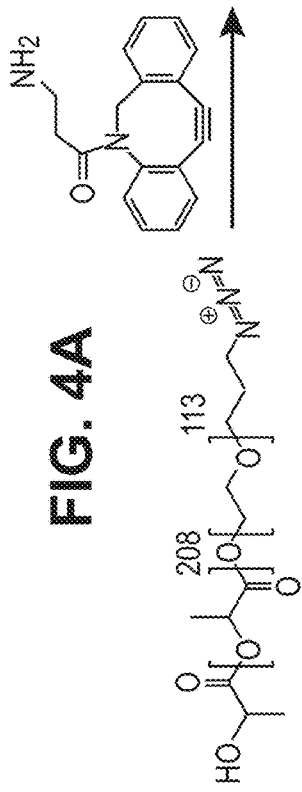
Figure 4B:
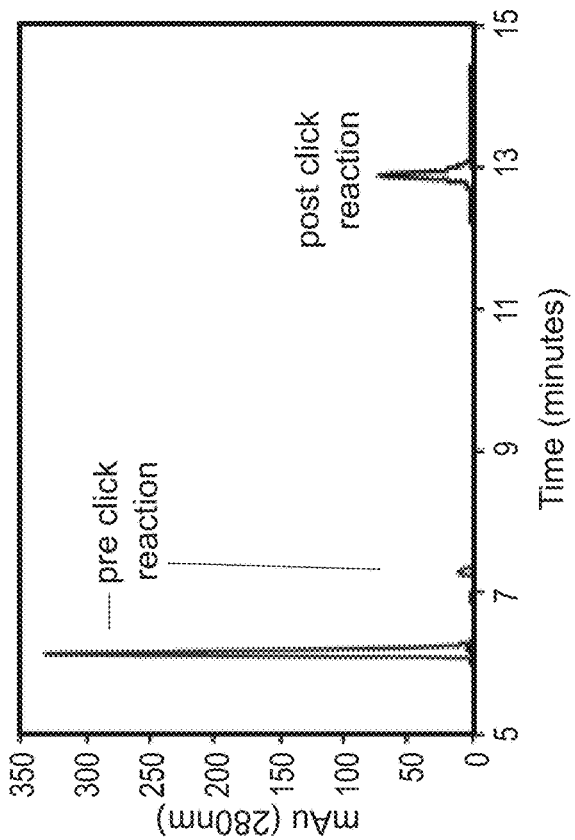

PLA-PEG-azide was synthesized by tin octanoate-catalyzed ring opening polymerization from HO-PEG-azide (FIGS. 3A and 3B). Polymer was generated that matched the properties of the polymer that comprised the bulk of the nanoparticle (16 kDa PLA, 5 kDa PEG). The integrity of the azide functional group on this polymer was confirmed by reaction with commercially available DBCO amine (FIG. 4A). Unreacted DBCO is detected both by ultraviolet (UV) A280 and mass spectrometry and the product PLA-PEG-azide-DBCO is detected by monitoring the A280 in the PLGA-PEG elution region of the chromatogram. Since PLA-PEG-azide does not have 280-nm absorptivity, an increase in absorbance is indicative that the reaction has proceeded and the UV properties of the DBCO moiety have been transferred to the polymer (FIG. 4B). It should be noted that the absorptivity of the DBCO moiety decreased when the triazole ring was formed, thus the polymer UV absorbance did not reach the same intensity as the starting free DBCO. This analysis demonstrated that the azide functional group was not altered during the polymerization conditions and a 99% consumption of DBCO amine was observed.

Figure 26:
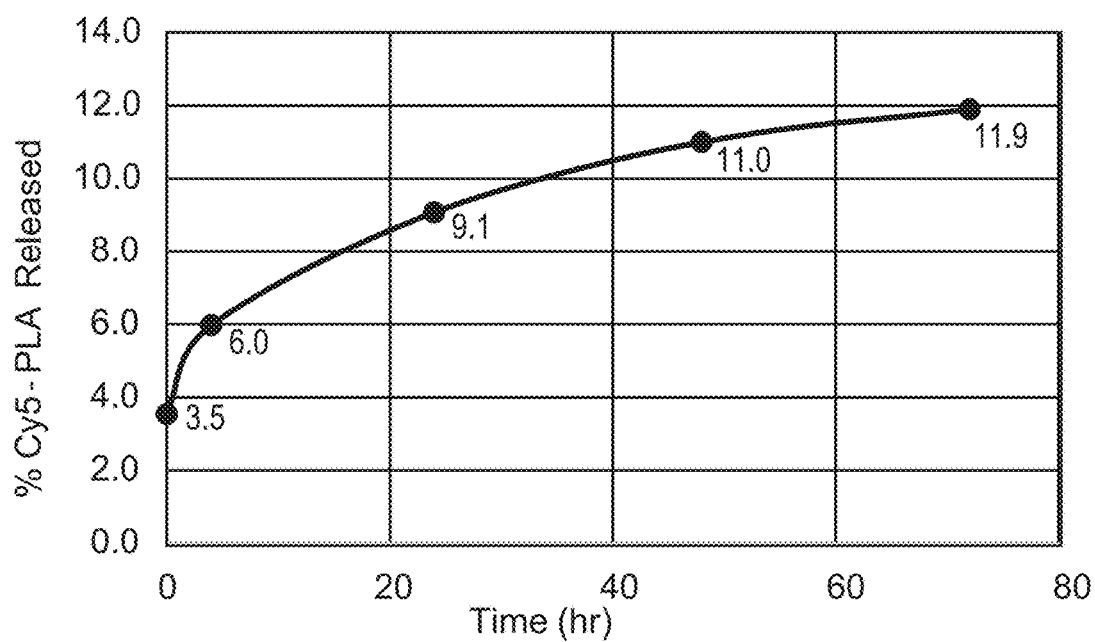
FIG. 26 depicts release of Cy5 PLA from nanoparticles over time at 37° C. measured by HPLC and in vitro release.

To enable nanoparticle detection in flow cytometry and other assays, we endeavored to incorporate a fluorescent label into the nanoparticle structure. While the click chemistry enables efficient surface modification of the nanoparticle with both ligands and fluorophores, it was preferable that the surface of the nanoparticle be modified only with the targeting ligands to prevent nonspecific binding. Thus, a Cy5 fluorescent payload that could be stably encapsulated in the nanoparticle core was synthesized. A 10-kDa PLA-carboxylic acid polymer was conjugated to a Cy5-amine fluorophore derivative. This polymer is hydrophobic and of sufficient molecular weight that it will remain largely encapsulated within the nanoparticle under assay conditions. This was confirmed using an in vitro release method, which demonstrated 4% release of Cy5 at T=0 followed by a<10% Cy5 over 48 hours, as depicted in FIG. 26.

Nanoparticles were generated by a nanoemulsion process, as described in Examples 1 and 2. Briefly, all of the nanoparticle components (PLA-PEG, PLA-PEG-azide, and PLA-Cy5) were dissolved in an organic phase consisting of benzyl alcohol and ethyl acetate. The organic phase was emulsified with an aqueous phase containing surfactants, and the emulsion passed through a high-pressure homogenizer to obtain the desired droplet size. The final emulsion was created by dilution into a large excess of water in order to extra solvents from the emulsions droplets and form particles. The final step was tangential flow filtration which removed unencapsulated components and solvents. Inclusion of the azide polymer at 30% (mole % of PLA-PEG polymers) and PLA-Cy5 polymer (1% by weight of total polymers) appeared to have little impact on particle size or polydispersity compared to a nanoparticle lacking these constituents, as shown in Table 2.

TABLE 2

Properties of PLA-PEG-azide polymer, non-azide polymers, azide functionalized nanoparticles and non-azide functionalized nanoparticles.

| | Polymer properties | | | | Nanoparticle properties | |
|---|---|---|---|---|---|---|
| | Mn (NMR) | Mn (SEC) | Mw (SEC) | PDI (SEC) | Size | Zeta Potential |
| 16-5-Azide | 20246 | 24663 | 27674 | 1.12 | 106.6 | −11.74 |
| 16-5-OMe | 19855 | 24213 | 27380 | 1.13 | 105.1 | −9.21 |

Figure 4C:
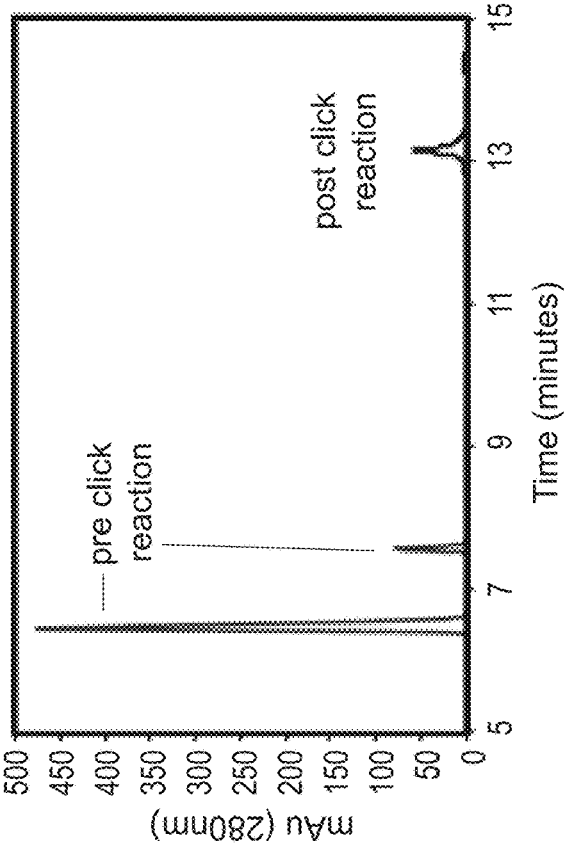

The final aqueous suspension of nanoparticles was characterized with respect to surface presentation and reactivity of the azide functional groups by using the DBCO-amine as a surrogate ligand. The azide groups are expected to represent 30% of the total PEG end groups on the surface of the nanoparticle. If all of the PEG chains were presented on the surface of the nanoparticle, then a stoichiometric amount of DBCO-amine should be fully consumed. Indeed, the reaction was very efficient and consumed approximately 100% of the DBCO-amine, indicating that the azide functional groups were presented nearly quantitatively on the nanoparticle surface (FIG. 4C). On the same 30% nanoparticle, lower stoichiometries of DBCO ligand can be used, producing nanoparticles with different levels of surface conjugated ligand. We observed approximately quantitative conjugation of DBCO ligand over 0.25% to 30% ranges tested. The reaction was incubated overnight at 4° C. to minimize nanoparticle degradation and Cy5 payload release.

Thus, use of azide nanoparticles and DBCO reagent was determined to be an effective methodology to introduce targeting ligands at various levels on the surface of nanoparticles. The high efficiency of the conjugation obviates the need for excess ligand, simplifying the post conjugation purification, and minimizing the risk of free ligand interfering with binding assays. In addition, the desired level of ligand can be controlled precisely and easily by varying the input ligand stoichiometry.

Example 4

EGF Targeted Nanoparticle

Figure 5:
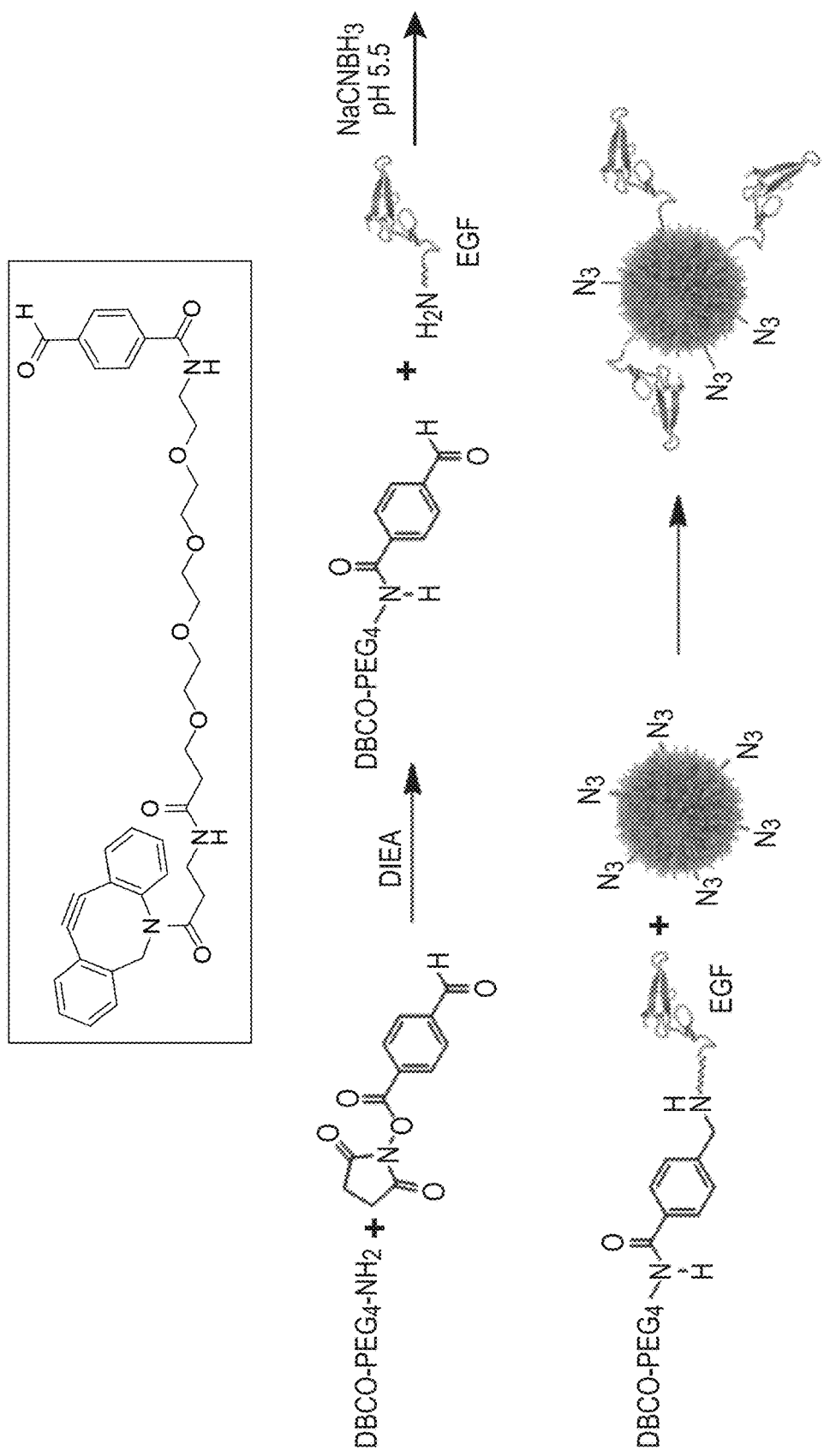
FIG. 5 depicts a DBCO aldehyde linker (top) and the preparation of DBCO-aldehyde for reductive amination to the N-terminus of EGF and subsequent conjugation to azide functionalized nanoparticles (bottom).

To establish a positive control for these studies, epidermal growth factor (EGF), a naturally occurring ligand for EGFR, was covalently tethered to DBCO to allow conjugation to the nanoparticle surface (FIG. 5). EGF is an approximately 6-kDa protein of 53 amino acids. Modification of EGF amino groups (lysines and N-terminal amine) indiscriminately using amide bond-forming reagents (such as NHS esters) can result in an impairment of EGF affinity toward EGFR. Selective N-terminal modification of EGF was achieved via reductive alkylation with a bifunctional DBCO-aldehyde linker. The aldehyde linker was reacted with EGF under various conditions and the products analyzed by LCMS. Reductive alkylation at pH 5.5 with 10 to 15 equivalents of the aldehyde and 10-mM sodium cyanoborohydride resulted in predominantly the singly alkylated EGF with 10% to 20% each of the doubly alkylated or unmodified EGF (Table 3). All reactions were run in 10% DMF (v/v) in 50-mM sodium acetate buffer, pH 5.5. Product distribution was measured by LC/MS (UV absorption at 280 nm).

TABLE 3

Reaction conditions screened for reductive animation of EGF.

| Reaction Conditions | | | Product Distribution | |
|---|---|---|---|---|
| mM NaCNBH3 | Equiv. Aldehyde | % EGF | % EGF-DBCO$_2$ | % EGF-DBCO |
| 10 | 5 | 35 | 6 | 59 |
| 10 | 10 | 26 | 8 | 66 |
| 10 | 15 | 12 | 16 | 72 |
| 10 | 20 | 11 | 18 | 71 |
| 15 | 20 | 7 | 23 | 70 |
| 20 | 20 | 6 | 26 | 68 |

Figure 6:
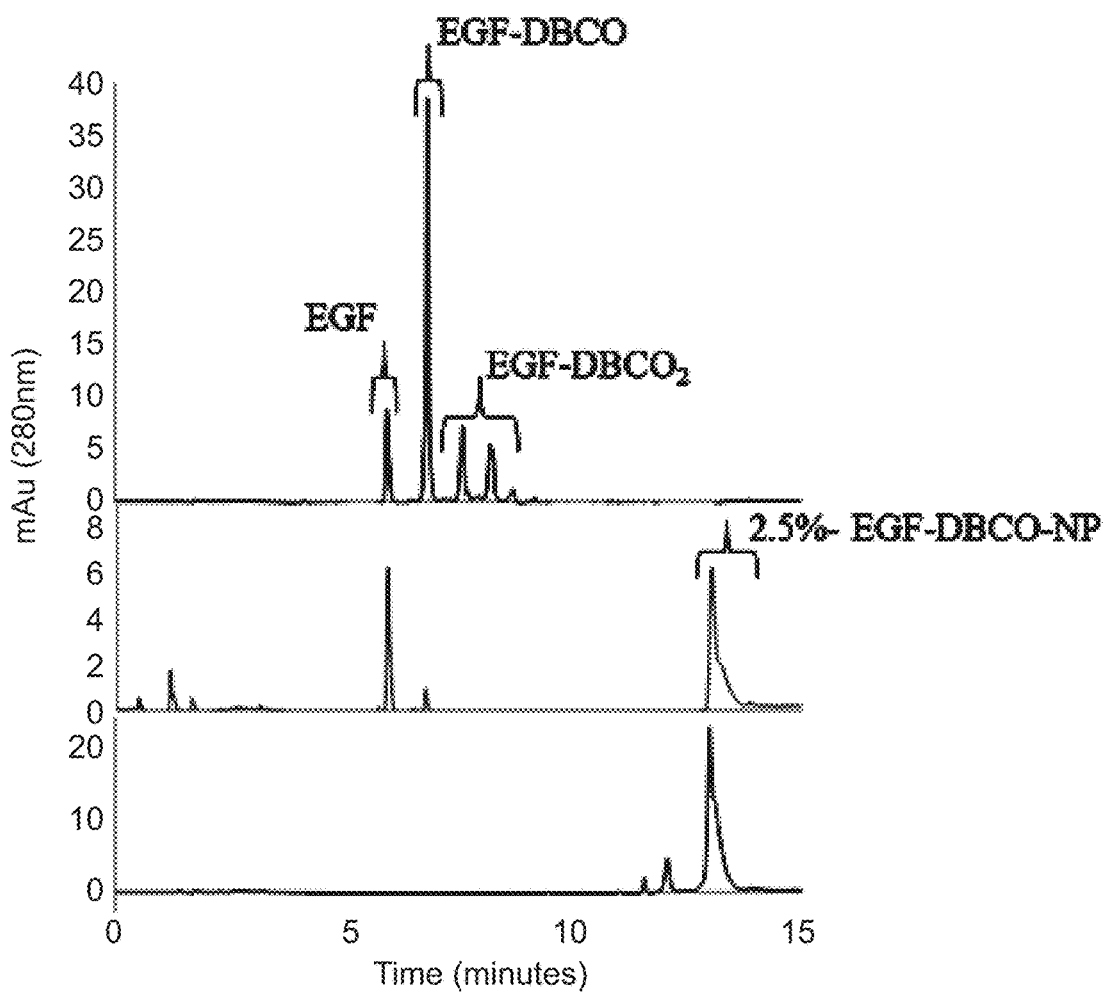
FIG. 6 LCMS analysis of EGF-DBCO post purification by Zeba Spin (top), after EGF-DBCO has been clicked to azide functionalized nanoparticles (middle), and after purification of nanoparticles by Zeba Spin (bottom).

While increasing the concentration of the reducing agent led to a higher consumption of EGF, this also produced a greater proportion of the doubly alkylated product. This was undesirable as it may be less active or could lead to nanoparticle cross-linking. In addition, unmodified EGF would not conjugate to the nanoparticles and could be removed subsequently using size exclusion chromatography (SEC). The resulting DBCO-EGF was purified from residual reagents using a desalting column and then concentrated using a centrifugal concentrator. The integrity of the DBCO moiety was confirmed by reacting the DBCO-EGF product with azido-aniline hydrochloride (AAHC). The singly and doubly modified DBCO-EGF were efficiently conjugated to AAHC while the unmodified EGF remained intact (FIG. 6 and Table 4).

TABLE 4

EGF-DBCO conjugation expected and observed molecular weights

| Compound | MW calculated | MW observed |
|---|---|---|
| EGF | 6347.1 | 6347.6 |
| EGF-DBCO | 6986.9 | 6986.9 |
| EGF-DBCO2 | 7626.7 | 7627.2 |
| EGF-DBCO-azidoanaline | 7121.1 | 7120.9 |

The DBCO-EGF ligand was next conjugated onto azide nanoparticles at approximately 2.5% ligand density (e.g., 1 out of every 12 azides would be conjugated with an EGF ligand) and the resulting conjugate purified by size exclusion chromatography. The singly and doubly labeled DBCO-EGF components were efficiently coupled to the nanoparticle while the unmodified EGF remained and was removed by SEC.

Example 5

Binding of EGF-NP to Recombinant EGFR

Figure 7A:
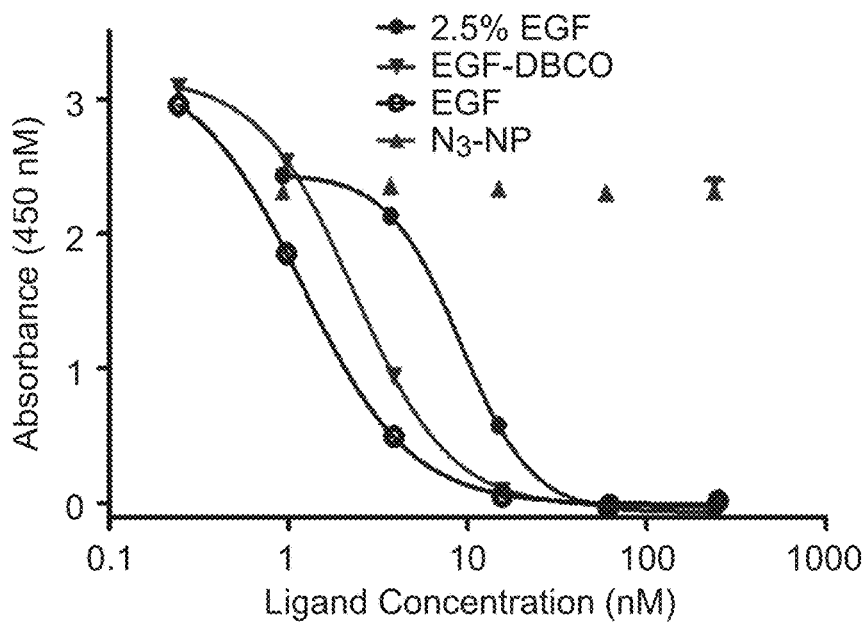
FIG. 7A depicts EGF nanoparticles and DBCO ligands binding to EGFR by EGF competition ELISA (EGF $IC_{50}$=1.2 nM, EGF-DBCO $IC_{50}$=2.3 nM, 2.5% EGF $IC_{50}$=9 nM).

The binding properties of the EGF-nanoparticles (EGF-NP) were evaluated by surface plasmon resonance (SPR, or Biacore) and using a competition ELISA assay. In the ELISA assay, nanoparticles or free EGF ligand are competed with a commercially available biotin-EGF conjugate for binding to recombinant human EGFR-Fc coated on 96-well plates. Recombinant human EGFR (5 μg/mL, R&D Systems) was captured on 96-well plates in 0.1-M carbonate/bicarbonate buffer (Sigma-Aldrich) at 4° C. overnight. Plates were blocked for 2 hours with 2% BSA in PBS at room temperature (RT). Peptides were incubated at 100 μM, with 0.7-nM biotinylated recombinant human EGF (Molecular Probes) in assay buffer (2% BSA, 0.05% Tween-20 in PBS) for 90 minutes at RT. Peptides were reconstituted as 100% DMSO stocks, resulting in a final concentration of DMSO in the assay of 2% for all samples. Plates were washed three times with PBS containing 0.05% Tween-20 (PBS-T) and then incubated with a 1:10,000 dilution of streptavidin-HRP (Piece) diluted in assay buffer for 90 minutes at RT. Plates were washed an additional three times with PBS-T and then incubated with TMB substrate (BioFx) for 15 minutes at RT. The reaction was stopped with stop solution (BioFx) and absorbance was read at 450 nm in a microplate reader (SpectraMax M5e, Molecular Devices). FIG. 7 shows the results of this analysis. As shown by ELISA, nanoparticles and free EGF-DBCO ligand compete with commercially available biotin-EGF for binding to recombinant human EGFR-Fc fusion protein coated onto 96-well plates. The DBCO-EGF ligand bound to EGFR approximately 2 fold worse (e.g., a 2 fold higher $IC_{50}$) than unmodified EGF, indicating that the DBCO modification chemistry had minimal impact on binding affinity (FIG. 7A). The nanoparticle-EGF conjugate has an $IC_{50}$ approximately 10-fold higher than unmodified EGF and 4 fold higher than DBCO-EGF. However, this is not entirely unexpected given that the EGF conjugated to the nanoparticle surface would not all be expected to make contact with the EGFR due to the three-dimensional structure and size of the nanoparticle. Therefore, conjugation of the EGF to the nanoparticle has modestly altered its binding affinity. Unmodified azide nanoparticles did not compete with EGF-biotin for binding to EGFR, demonstrating no nonspecific nanoparticle binding.

Figure 7B:
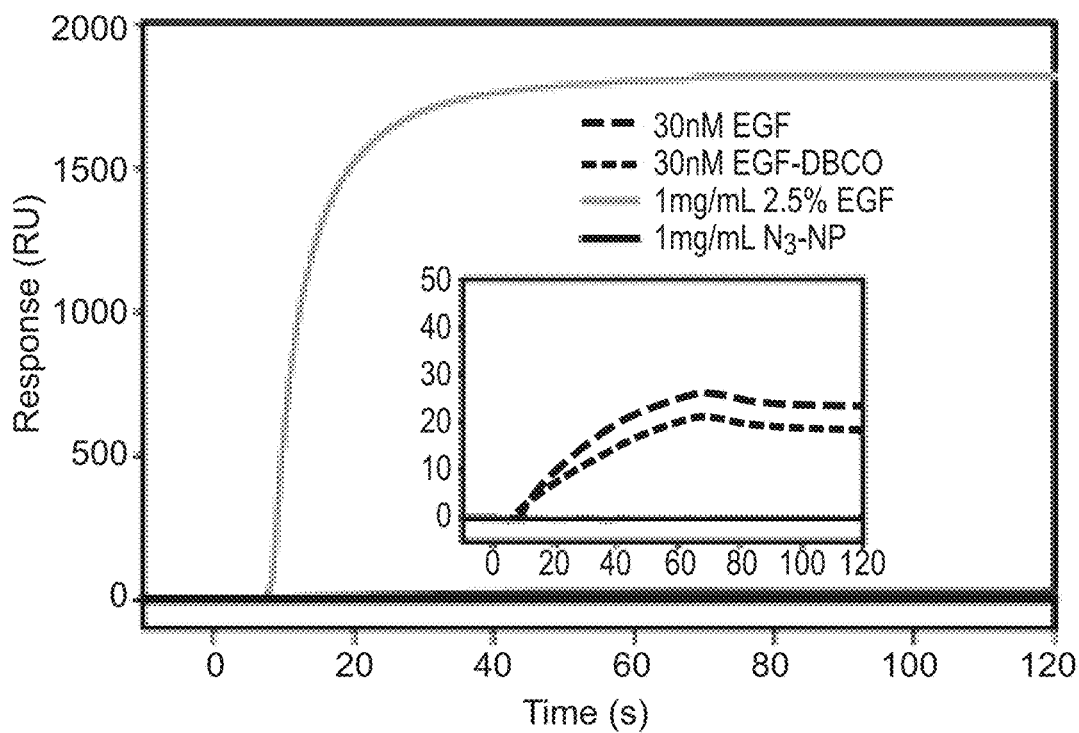
FIG. 7B depicts SPR analysis of EGF, EGF-DBCO, EGF nanoparticle, and base azide nanoparticle binding to EGFR-Fc surface. Inset zooms in on lower signal from unmodified EGF and minimal nonspecific binding of base azide nanoparticle. PTNP inidicates non-functionalized nanoparticle.

SPR was used as an orthogonal method to characterize unmodified EGF and EGF-nanoparticle conjugate binding to recombinant EGFR-Fc fusion protein. As seen in FIG. 7B, DBCO modified EGF has a slightly altered sensorgram, in agreement with ELISA data. The EGF-nanoparticle gives a distinctly larger response compared to unmodified EGF, due to the larger molar mass of the analyte. Non-functionalized azide-nanoparticles exhibit minimal binding to the EGFR-Fc coated surface, indicating that the response of the EGF nanoparticle results from specific receptor binding. Due to the multivalent nature of the interaction of the nanoparticle with the EGFR receptor surface and the difficulty to accurately characterize the molecular weight of the nanoparticle, an equilibrium binding constant ($K_D$) was not determined for this interaction. However, the binding kinetics of the SPR curve suggest a tight interaction with a slow off-rate, which would be expected for a multivalent binding interaction.

Example 6

Low Molecular Weight EGFR Ligand Screening

While EGF served as a reliable proof-of-concept ligand for nanoparticle targeting to EGFR, we sought a lower molecular weight ligand that would be compatible with the nanoparticle manufacturing process. As a first approach, overlapping 10 amino acid-long peptide fragments of the naturally occurring ligands EGF and TGFα (transforming growth factor alpha) were synthesized and screened for binding to EGFR using the EGFR competition ELISA and SPR. Unfortunately, and contrary to reports that indicated some of the fragments synthesized retained EGFR binding capability, none of the peptides generated demonstrated binding to EGFR by either method (Tables 5 and 6).

TABLE 5

EGF fragments

| Name | SEQ ID NO: | Sequences[a] | $K_D$ | % inhibition of EGF |
|---|---|---|---|---|
| EGFf-1 | 29 | H2N-NSDSECPLSH-CONH2 | No binding | <20 |
| EGFf-2 | 30 | H2N-CPLSHDGYCL-CONH2 | Not observed | No tested |
| EGFf-3 | 31 | H2N-DGYCLHDGVC-CONH2[b] | No binding | 62.5 |
| EGFf-4 | 32 | H2N-HDGVCMYIEA-CONH2 | Not observed | Not tested |
| EGFf-5 | 33 | H2N-MYIEALDKYA-CONH2 | No binding | <20 |
| EGFf-6 | 34 | H2N-LDKYACNC(Acm)VV-CONH2 | No binding | <20 |
| EGFf-7 | 35 | H2N-C(Acm)NCVVGYIGE-CONH2 | No binding | <20 |
| EGFf-8 | 36 | H2N-GYIGERCQYR-CONH2 | No binding | <20 |
| EGFf-9 | 37 | H2N-RCQYRDLKWW-CONH2[b] | >100 mM | 63.8 |

TABLE 5-continued

EGF fragments

| Name | SEQ ID NO: | Sequences[a] | $K_D$ | % inhibition of EGF |
|---|---|---|---|---|
| EGFf-10 | 38 | H2N-YRDLKWWELR-CONH2 | No binding | <20 |
| EGFf-11 | 39 | H2N-CLHDGVC(Acm)MYIEALDKYACN-CONH2 | Not observed | Not tested |
| EGFf-12 | 40 | H2N-CMYIEALDKYACN-CONH2 | Not observed | Not tested |
| EGFf-13 | 41 | H2N-CVVGYIGERC-CONH2 | Not observed | Not tested |

[a]Disulfide bonds link the underlined cysteines. Acm protecting groups were left on unpaired cysteines.
[b]Decreased binding over time, due to oxidative dimerization via free cysteines

TABLE 6

TGF fragments

| Name | SEQ ID NO: | Sequences[a] | $K_D$ | % inhibition of EGF @100 μM |
|---|---|---|---|---|
| TGFf-1 | 42 | H2N-G-Par-GG-CHSGYVGARC-CONH2 | No binding | Not tested |
| TGFf-2 | 43 | H2N-G-Par-GG-CFHGTC(Acm)RFLVQEDKPAC-CONH2 | No binding | Not tested |
| TGFf-3 | 44 | H2N-G-Par-GG-CPDSHTQFC(Acm)FHGTC-CONH2 | Not soluble | Not tested |
| TGFf-4 | 45 | H2N-G-Par-GG-ADLLAVVAA-CONH2 | No binding | <20 |
| TGFf-5 | 46 | H2N-G-Par-GG-ARCEHADADL-CONH2 | No binding | <20 |
| TGFf-6 | 47 | H2N-G-Par-GG-SGYVGARCEH-CONH2 | No binding | <20 |
| TGFf-7 | 48 | H2N-G-Par-GG-AC(Acm)VCHSGYVG-CONH2 | No binding | <20 |
| TGFf-8 | 49 | H2N-G-Par-GG-QEDKPAC(Acm)VCH-CONH2 | No binding | <20 |
| TGFf-9 | 50 | H2N-G-Par-GG-CRFLVQEDKP-CONH2 | No binding | <20 |
| TGFf-10 | 51 | H2N-G-Par-GG-C(Acm)FHGTCRFV-CONH2 | No binding | <20 |
| TGFf-11 | 52 | H2N-G-Par-GG-SHTQFCFHGT-CONH2 | No binding | <20 |
| TGFf-12 | 53 | H2N-G-Par-GG-NDCPDSHTQF-CONH2 | No binding | <20 |
| TGFf-13 | 54 | H2N-G-Par-GG-WSHFNDCPD-CONH2 | No binding | <20 |
| TGFf-14 | 55 | H2N-G-Par-GG-ARCEHADLLA-CONH2 | No binding | <20 |

[a]Disulfide bonds link the underlined cysteines. Acm protecting groups were left on unpaired cysteines.

Figure 8A:
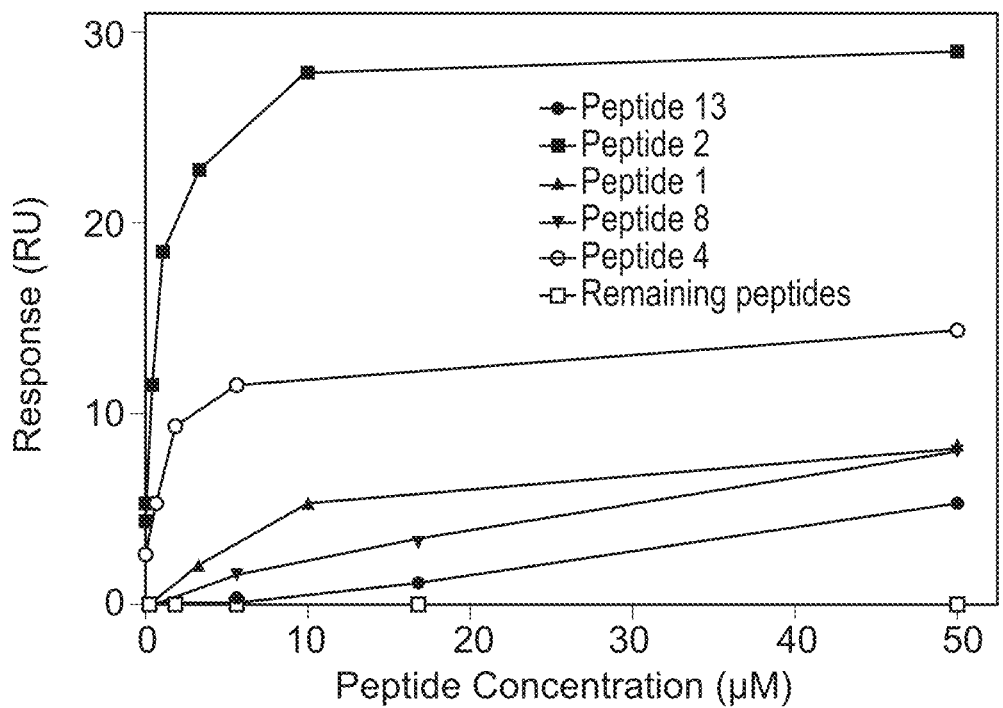
FIG. 8A depicts a plot of SPR binding data for reported EGFR binding peptides.
Figure 8B:
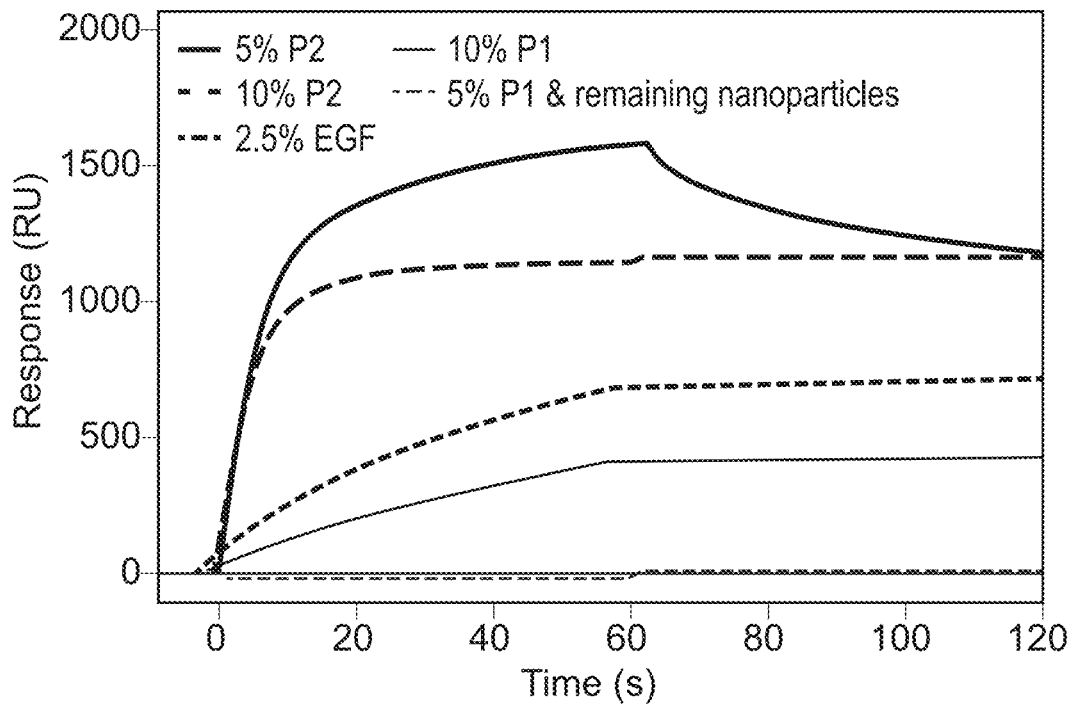
FIG. 8B depicts SPR analysis of selected literature peptides conjugated to nanoparticles (1 mg/mL) at 5% and 10%. 2.5% EGF nanoparticle is shown for comparison.

A review of the literature revealed several peptides (MW range 1200-1900) reported to bind to EGFR. All of the peptides were synthesized and evaluated for EGFR binding using SPR (Table 7). Competition ELISA was not used for screening these peptides, since not all are reported to compete with EGF for binding to EGFR. Surprisingly, only a small number of the reported peptides exhibited reproducible binding to EGFR. FIGS. 8A and 8B show a summary of the SPR binding data for the peptides. Only 5 of the 17 peptides synthesized gave binding signals above baseline, and of these only 3 showed saturable binding at a concentration less than 50 μM. All 5 binding peptides and a selection of the other nonbinding peptides were resynthesized with DBCO moieties attached to a lysine side chain at the C-terminus (including a Gly-Gly spacer) and then conjugated to azide nanoparticles at ligand densities of 5% and 10% (~225 and 450 ligands per nanoparticle).

TABLE 7

Sequences of peptides reported to bind to EGF.

| SEQ ID NO: | Sequences | Reported EGF Competitor | Peptide ID | Molecular Weight |
|---|---|---|---|---|
| 56 | SECFPLAPDWLSCIL | + | 1 | 1689.79 |
| 57 | DPCTWEVWGRECLQ | - | 2 | 1717.73 |
| 58 | TDCVIFGLETYCLR | - | 3 | 1628.77 |
| 59 | SGCLDALWQCVY | - | 4 | 1353.58 |
| 60 | LPDDSLPELICKVR | - | 5 | 1652.89 |
| 61 | GPCVLIRDYYLLCLE | - | 6 | 1765.89 |
| 62 | VLCHRYYHPICYT | + | 7 | 1663.78 |
| 63 | MFCFRWYAGWSCVS | + | 8 | 1738.72 |
| 64 | HFYPTKTPGY | - | 9 | 1451.72 |
| 65 | AASRALWAFNSD | - | 10 | 1307.62 |
| 66 | SYYWGYTVDIRRGGK | - | 11 | 1577.76 |
| 67 | KTCVSTTFDLWFVCFA | + | 12 | 1863.87 |
| 68 | YHWYGYTPQNVI | + | 13 | 1538.73 |

TABLE 7-continued

Sequences of peptides reported to bind to EGF.

| SEQ ID NO: | Sequences | Reported EGF Competitor | Peptide ID | Molecular Weight |
|---|---|---|---|---|
| 69 | LARLLT | - | 14 | 684.46 |
| 70 | CEHGAMEIC | + | 15 | 988.36 |
| 71 | AKFNDYWRW | + | 16 | 1283.62 |
| 72 | CPAKFSPSVC | + | 17 | 1628.77 |
| 73 | YCPIWKFPDEECY | - | 18 | 1688.7 |

Binding of nanoparticles to EGFR-Fc was evaluated using SPR. FIG. 8B shows the binding sensorgrams for the nanoparticle conjugates. A nanoparticle binding signal comparable to EGF-NP was demonstrated for $P_1$, a slightly lower binding was observed for $P_2$. However, no binding for the other peptide-nanoparticle conjugates was observed under these conditions. The binding response for $P_1$ conjugated to nanoparticle at 10 mol % was higher and the kinetics seem to be faster (on and off rates) than $P_2$ nanoparticles at 5 and 10% although $P_2$ did bind to EGFR at both ligand densities. The faster kinetics exhibited by $P_1$ may explain why $P_1$ was only capable of mediating binding of the nanoparticle to EGFR at higher (10%) ligand density. We believe that increasing the local concentration of $P_1$ by loading more onto the particle in turn leads to more opportunities for binding despite the fact kinetics exhibited by the ligand. $P_1$ was studied further to identify the critical binding elements.

Example 7

Structure Activity Relationship of $P_1$

Figures 9A, 9B:
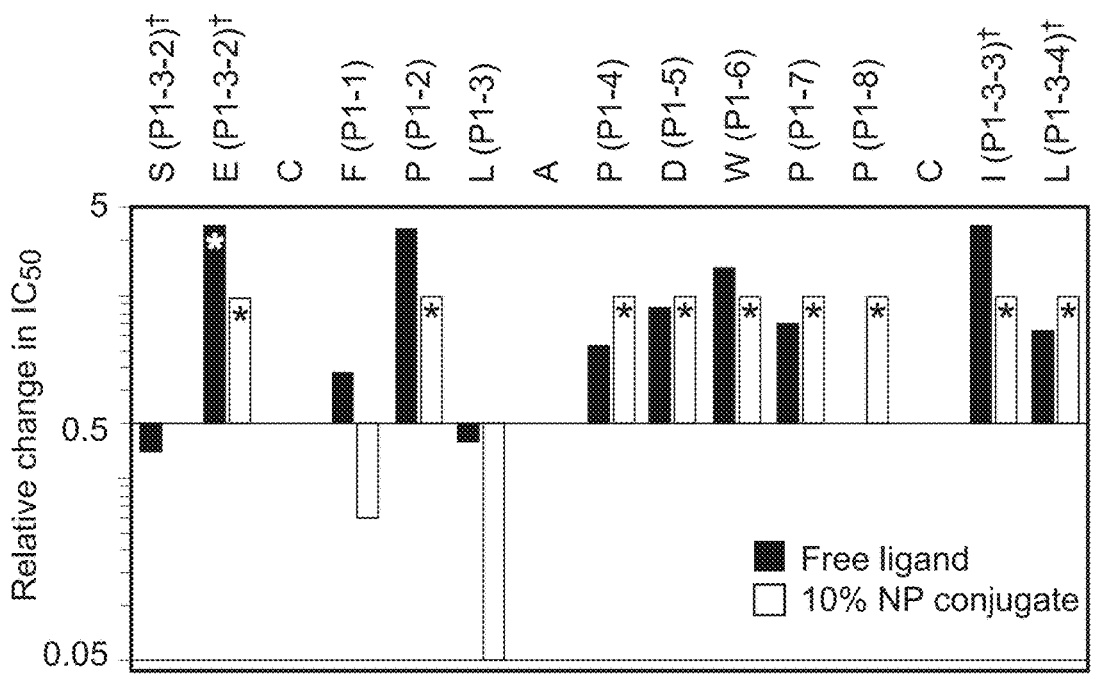
FIG. 9A depicts the relative $IC_{50}$ for free ligand and nanoparticle conjugate binding by EGF competition ELISA. Each amino acid in $P_1$ was replaced with alanine and the impact on binding was compared to the parent peptide or peptide-NP.
FIG. 9B depicts $P_1$ alanine scan nanoparticles binding by EGFR competition ELISA ($P_{1-3}$ $IC_{50}$=10.3 µg/mL, $P_1$ $IC_{50}$=211 µg/mL).

An alanine scan was performed on the amino acids within the cyclic portion of the peptide structure to determine which amino acids were critical for binding. Each amino acid within the peptide was individually replaced with alanine. $P_1$ demonstrated competition with EGF so an EGF competition ELISA was used to evaluate for binding to EGFR (FIG. 9A and Table 8). Data indicated that most amino acids in this peptide sequence were required for optimal peptide binding to EGFR since binding was reduced in the alanine mutated peptides. However, one amino acid (Leu6), when changed to alanine, results in a peptide with a slightly higher affinity than $P_1$ ($P_{1-3}$). Subsequently, an alanine scan of the flanking amino acids on $P_{1-3}$ was performed. Three of the four flanking residues also played a significant role in binding to EGFR as demonstrated by reduced EGFR binding in the alanine mutated peptides. However, alanine at position 1 demonstrated a minimally improved affinity relative to $P_{1-3}$.

TABLE 8

$P_1$ alanine scan

Ac-$S_1E_2C_3F_4P_5L_6A_7P_8D_9W_{10}L_{11}S_{12}C_{13}I_{14}L_{15}$GGK(DBCO)-CONH2 (SEQ ID NO: 74)

| AA Position | Peptide ID | Peptide Relative $IC_{50}$ (normalized to $P_1$) | 10% NP Relative $IC_{50}$ (normalized to $P_1$) |
|---|---|---|---|
| 3 | x | — | — |
| 4 | $P_{1-1}$ | 1.9 | ~0.3 |
| 5 | $P_{1-2}$ | 11.5 | >2.5 |
| 6 | $P_{1-3}$ | 0.8 | 0.05 |
| 7 | x | | |
| 8 | $P_{1-4}$ | 2.7 | >3 |
| 9 | $P_{1-5}$ | 4.4 | >3 |
| 10 | $P_{1-6}$ | 7.1 | >3 |
| 11 | $P_{1-7}$ | 3.5 | >3 |
| 12 | $P_{1-8}$ | 1 | >3 |
| 13 | x | — | — |
| 1 | $P_{1-3-1}$ | 0.7 | 1 |
| 2 | $P_{1-3-2}$ | >5 | >10 |
| 14 | $P_{1-3-3}$ | >5 | >10 |
| 15 | $P_{1-3-4}$ | 3.2 | >10 |

All of the alanine scan peptides were conjugated to nanoparticles at 10 mol % and evaluated for binding using the EGF competition ELISA. The $P_{1-3}$ (Leu6-Ala) conjugate demonstrated enhanced EGFR binding compared to the $P_1$ conjugate. As shown in FIG. 9B, the affinity of the $P_{1-3}$ nanoparticle was increased approximately 20-fold relative to $P_1$ nanoparticles, indicating that this single amino acid mutation, while having a modest impact on free ligand affinity, led to an unexpected improvement in binding to EGFR when conjugated to nanoparticles.

Figure 9C:
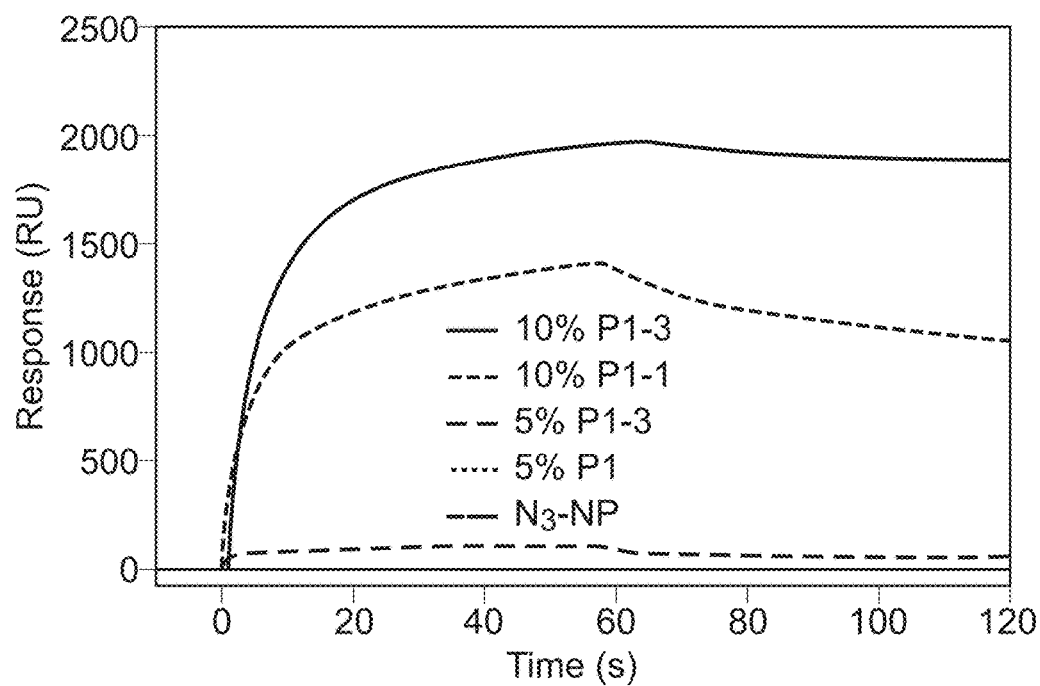
FIG. 9C depicts $P_1$ and $P_{1-3}$ NP binding by SPR at 1 mg/mL

SPR analysis was performed to compare $P_1$ and $P_{1-3}$ nanoparticle binding to EGFR. Sensorgrams of $P_1$ and $P_{1-3}$ nanoparticles at 1 mg/mL nanoparticle concentration demonstrate minimal binding at 5% density and a more robust binding at 10% ligand density (FIG. 9C). Additionally, the 10% $P_{1-3}$ nanoparticle exhibited a notably slower off-rate compared to the 10% $P_1$ nanoparticle. Thus, a small improvement in free peptide affinity resulted in a significant change in nanoparticle binding properties.

While encouraging EGFR binding was obtained with $P_{1-3}$ nanoparticles, this ligand shares an epitope with EGF, which may cause targeted nanoparticles to suffer from competition with the natural ligand in vivo. Additionally, we desired a ligand that could achieve robust nanoparticle binding at lower densities such that the nanoparticle surface is minimally decorated which may be important for maintaining particle stealth and long circulation. Additional analogs of $P_{1-3}$ were generated including replacement with N-methyl amino acids and other natural and unnatural amino acid point mutations, but none of the resulting peptides demonstrated any additional EGFR binding over $P_{1-3}$ (Table 9).

TABLE 9

$K_D$ and relative IC50 of $P_{1-3}$ truncation and N-methyl analogs.

| Peptide | SEQ ID NO: | Sequence[a] | $K_D$ (µM) |
|---|---|---|---|
| *$P_{1-3}$ truncations* | | | |
| $P_{1-3-5}$ | 75 | Ac-SECFPAAPDWLSCGGK(DBCO)-CONH2 | |
| $P_{1-3-6}$ | 76 | Ac-CFPAAPDWLSCGGK(DBCO)-CONH2 | NB |
| $P_{1-3-7}$ | 77 | Ac-CFPAAPDWLSCGGK(DBCO)--CONH2 | NB |
| *$P_{1-3}$ N-methyl scan* | | | |
| $P_{1-3-8}$ | 78 | Ac-SECFPA(Me)APDWLSCILGGK(DBCO)-CONH2 | NB |
| $P_{1-3-9}$ | 79 | Ac-SECFPAAPDWL(Me)SCILGGK-CONH2 | NB |
| $P_{1-3-10}$ | 80 | Ac-SECFPAAPDWLSCI(Me)LGGK-CONH2 | NB |
| $P_{1-3-11}$ | 81 | Ac-SECFPAAPDWL(Me)SCILGGK-CONH2 | NB |
| $P_{1-3-12}$ | 82 | Ac-SE(ME)CFPAAPDWLSCILGGK(DBCO)-CONH2 | 4.4 |
| $P_{1-3-13}$ | 83 | Ac-SECF(ME)PAAPDWLSCILGGK(DBCO)-CONH2 | 1.4 |
| $P_{1-3-8}$ | 84 | Ac-SECFPA(Me)APDWLSCILGGK(DBCO)-CONH2 | NB |
| *Alternate DBCO placement* | | | |
| $P_{1-3-14}$ | 85 | (DBCO)SECFPAAPDWLSCIL-CONH2 | NB |

[a]Disulfide bonds link the underlined cysteines.

Example 8

Structure Activity Relationship of $P_2$

Another literature EGFR binding peptide demonstrated to mediate nanoparticle binding, $P_2$, was reported to have enhanced affinity when EGF is also bound to EGFR. In our hands, however, SPR analysis of the affinity of this peptide in the presence or absence of EGF revealed a comparable $K_D$ (Table 10).

TABLE 10

Affinity of $P_2$ for apo-EGFR is comparable to the affinity for EGF bound EGFR

| | Without EGF | With EGF |
|---|---|---|
| $k_a$ (M$^{-1}$s$^{-1}$) | $3.7 \pm 0.2 \times 10^4$ | $3.8 \pm 0.4 \times 10^4$ |
| $k_d$ (s$^{-1}$) | $9 \pm 2 \times 10^{-3}$ | $7 \pm 2 \times 10^{-3}$ |
| $K_D$ (M) | $2.4 \pm 0.3 \times 10^{-7}$ | $1.7 \pm 0.6 \times 10^{-7}$ |

Figure 10:
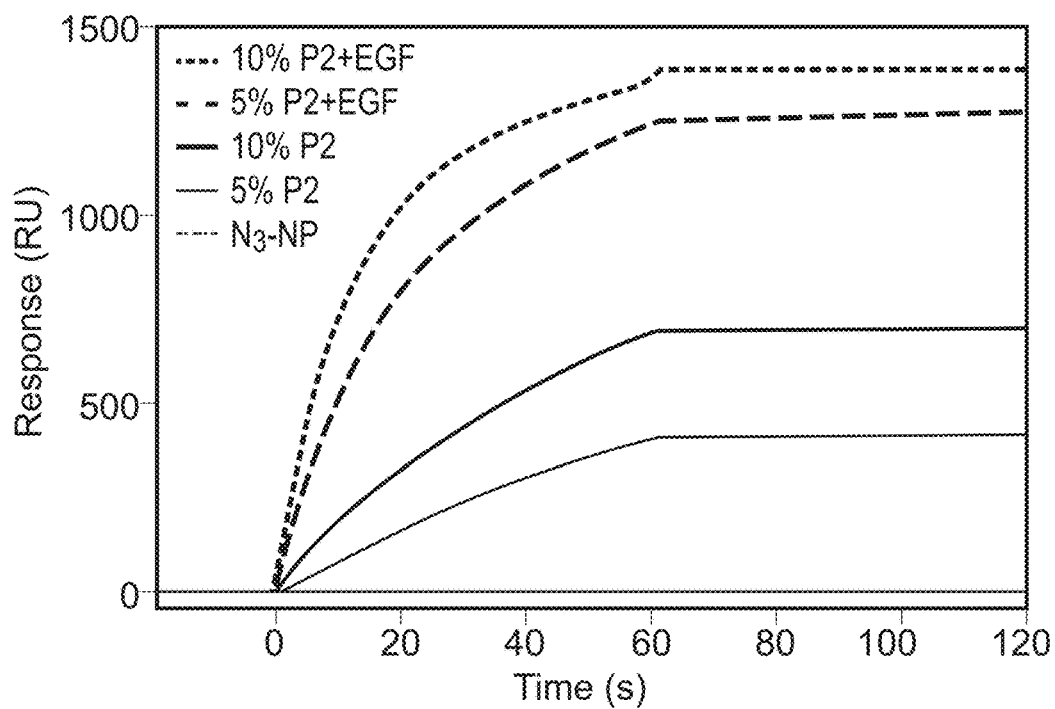
FIG. 10 depicts SPR analysis of the affinity of $P_2$-NP conjugates (1 mg/mL) at 5 and 10% ligand density in the presence or absence of EGF
Figure 11:
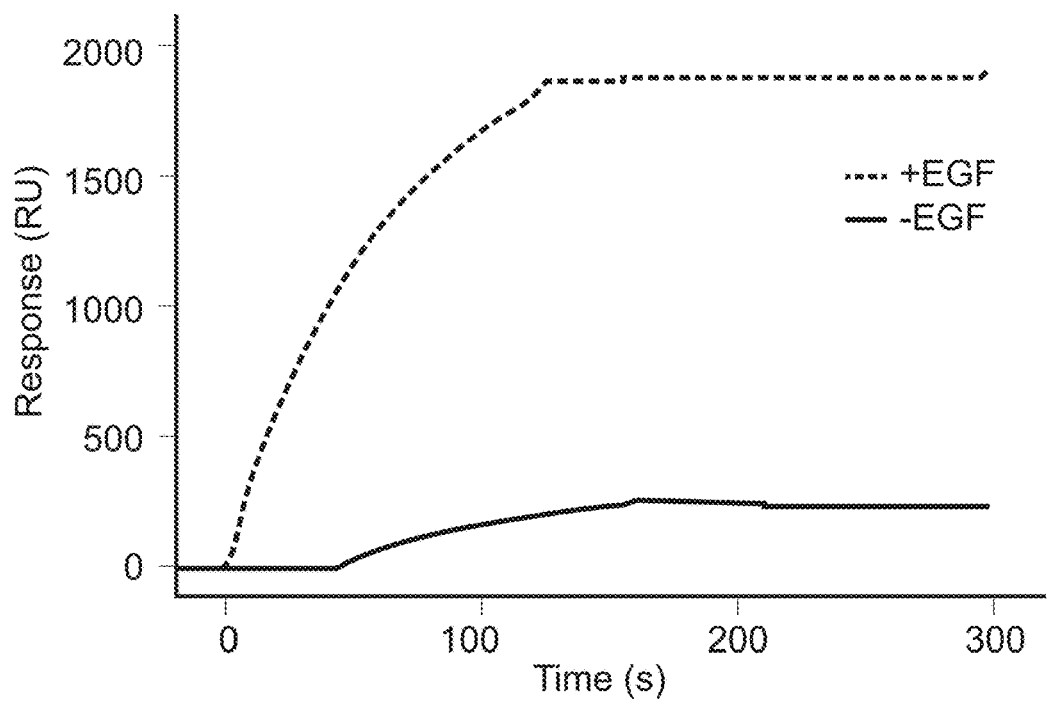
FIG. 11 depicts SPR analysis of $P_2$-NP conjugate binding (at 0.25 mg/ml) in the presence or absence or EGF.
Figure 12:
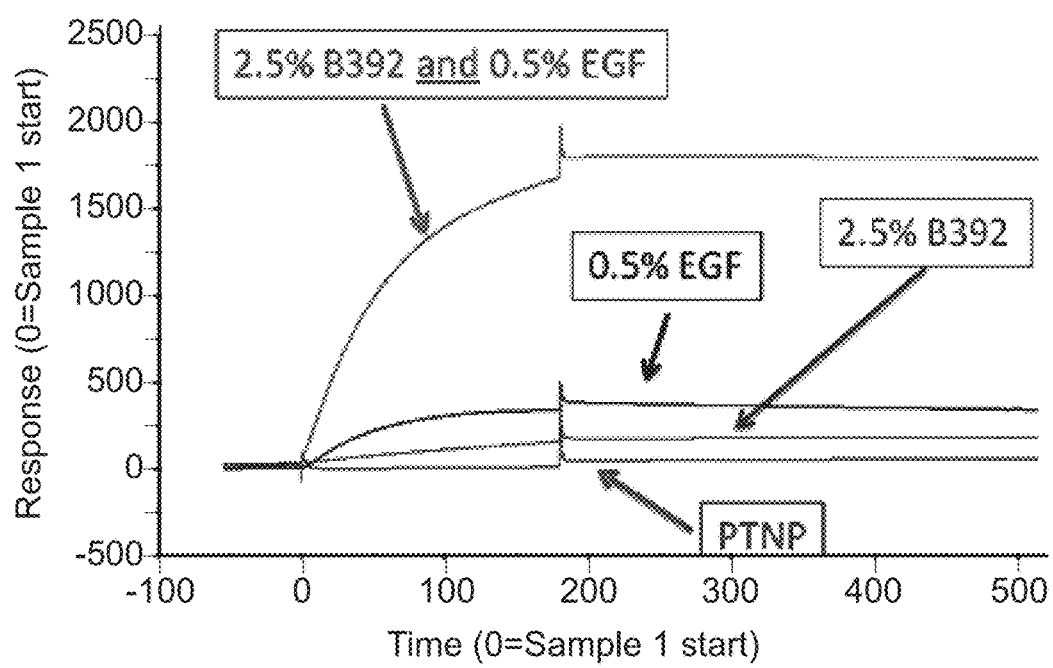
FIG. 12 depicts the synergistic impact of EGF/$P_2$ dual targeted NPs. PTNP inidicates non-functionalized nanoparticle.

Interestingly, nanoparticle conjugates of $P_2$ at both 5 and 10% ligand density exhibited enhanced binding to EGFR in the presence of bound EGF (FIG. 10 and FIG. 11). Furthermore, a synergistic effect was seen for dual-targeted nanoparticles that included both EGF and $P_2$ (FIG. 12). EGFR is known to undergo a conformational change that is stabilized upon EGF binding, converting to a more "open" configuration that enables EGFR dimerization. The original peptide was discovered by phage display in the presence of EGF and was studied as a liposome conjugate. Therefore, the binding epitope may be present in the bound or unbound state of EGFR, but the epitope may be more accessible when the EGFR is in the EGF bound state, allowing a less sterically inhibited approach of the nanoparticle, liposome, or phage particle.

Since a ligand that was not competitive with EGF was desirable for targeted nanoparticle delivery, $P_2$ was further evaluated to understand its properties and to optimize binding affinity. Three features were successfully modulated to improve nanoparticle binding.

Analogs of peptide $P_2$ were initially generated with C-terminal propargyl glycine moieties, which were intended for conjugation to azide nanoparticles using CuAAC. However, in later work the alkyne was replaced with the DBCO moiety as the SPAAC chemistry was determined to be more efficient and less likely to generate impurities of the ligand during conjugation. Nevertheless, free ligands were evaluated containing this C-terminal moiety to evaluate the structure activity relationship for the peptide.

Figure 13:
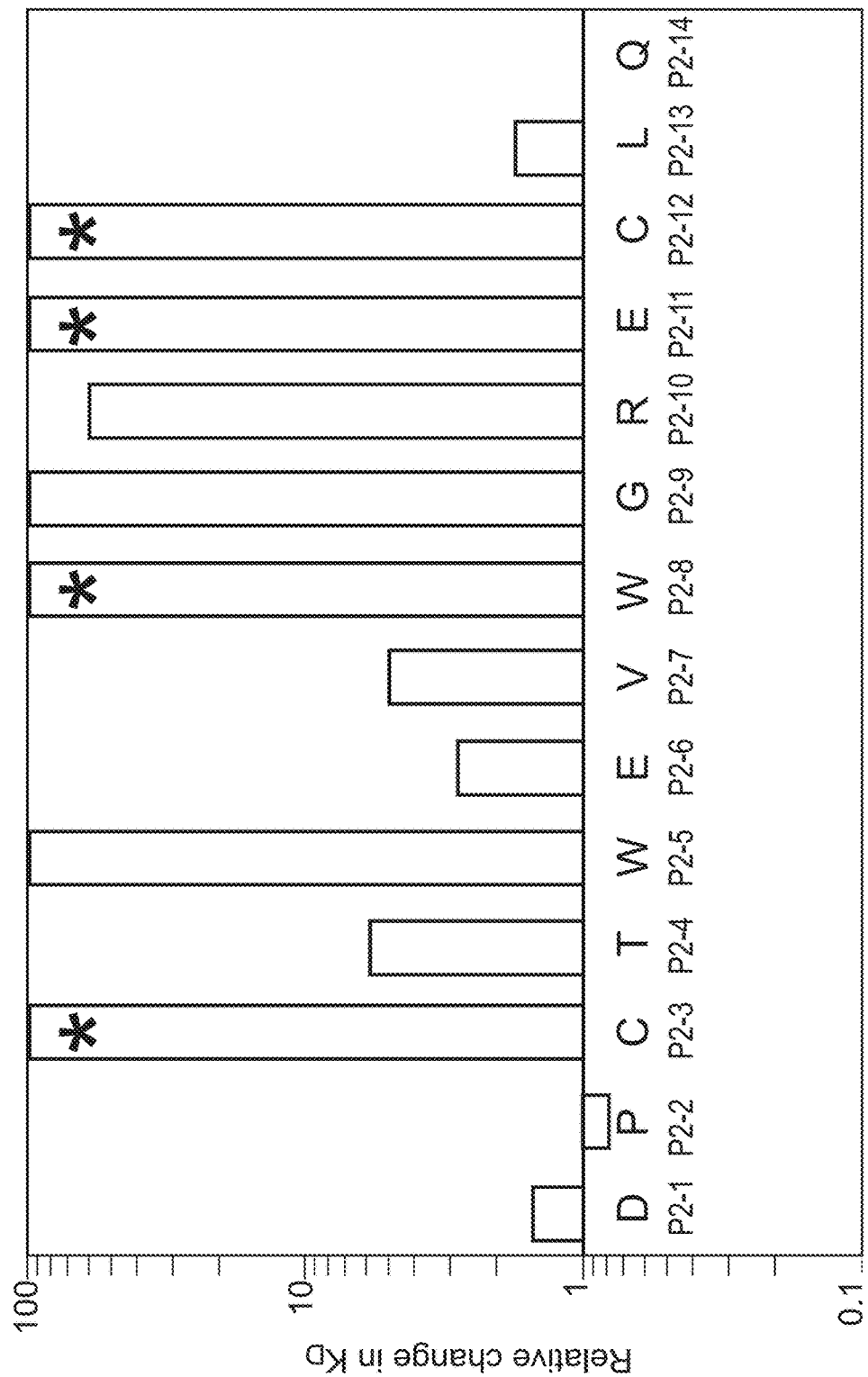
FIG. 13 shows results of alanine scanning of the $P_2$ peptide that indicates the critical residues for binding EGFR. Relative binding affinity as measured by SPR is indicated for each peptide relative to the $K_D$ of the parent peptide $P_2$. *Value is higher than it appears in graph. Figure discloses SEQ ID NO: 199.

Alanine scan analysis on $P_2$ highlighted the critical components of the peptide structure (FIG. 13 and Table 11). In particular, the cyclic structure and one aromatic residue (Trp8) were most critical to binding. Other important residues included the other aromatic residue (Trp 5) and residues 9 to 11 (Gly-Arg-Glu). Residues 4, 6, and 7 and the flanking amino acids 1, 2, 13, and 14 (outside the cyclic portion) had minor to no impact on binding when changed to alanine. Notably replacement of Pro2 with alanine ($P_{2-2}$) appeared to yield a modestly higher affinity peptide. Truncation analysis indicated that the core binding elements were contained within the residues between the cysteines, which corroborated the alanine scan analysis (Table 12).

TABLE 11

$P_2$ Ala Scan

| AA Position | Peptide ID | $K_D$ (µM) | Relative Affinity |
|---|---|---|---|
| Parent | $P_2$ | 0.8 | 1 |
| 1 | $P_{2-1}$ | 1.3 | 1.6 |
| 2 | $P_{2-2}$ | 0.6 | 0.8 |
| 3 | $P_{2-3}$ | nb | nb |
| 4 | $P_{2-4}$ | 4.4 | 5.7 |
| 5 | $P_{2-5}$ | 75 | 96 |
| 6 | $P_{2-6}$ | 2.3 | 2.9 |
| 7 | $P_{2-7}$ | 4.0 | 5.1 |
| 8 | $P_{2-8}$ | nb | nb |
| 9 | $P_{2-9}$ | 78 | 100 |
| 10 | $P_{2-20}$ | 50 | 63 |
| 11 | $P_{2-11}$ | ~300 | >100 |
| 12 | $P_{2-12}$ | nb | nb |
| 13 | $P_{2-13}$ | 1.4 | 1.8 |
| 14 | $P_{2-14}$ | 1.7 | 2.1 |

TABLE 12

Truncations, including those with alternative alkyne positioning

| Name | SEQ ID NO: | Sequences[a] | $K_D/P_2$ $K_D$ |
|---|---|---|---|
| $P_{2-15}$ | 86 | H2N-DPCTWEVWGREC-GG-Par-G-CONH2 | 0.9 |
| $P_{2-16}$ | 87 | H2N-CTWEVWGRECLQ-GG-Par-G-CONH2 | 2.0 |
| $P_{2-17}$ | 88 | H2N-CTWEVWGREC-GG-Par-G-CONH2 | 0.4 |
| $P_{2-18}$ | 89 | H2N-DACTWEVWGREC-GG-Par-G-CONH2 | 1.6 |

TABLE 12-continued

Truncations, including those with alternative alkyne positioning

| Name | SEQ ID NO: | Sequences[a] | $K_D/P_2 K_D$ |
|---|---|---|---|
| $P_{2-19}$ | 90 | H2N-A<u>C</u>TWEVWGRE<u>C</u>-GG-Par-G-CONH2 | 2.4 |
| $P_{2-20}$ | 91 | Ac-A<u>C</u>TWEVWGRE<u>C</u>-GG-Par-G-CONH2 | 3.0 |
| $P_{2-21}$ | 92 | H2N-Par-A<u>C</u>TWEVWGRE<u>C</u>-CONH2 | 6.7 |
| $P_{2-22}$ | 93 | H2N-DP<u>C</u>TWEVWGRE<u>C</u>-Par-CONH2 | 1.8 |
| $P_{2-23}$ | 94 | H2N-Par-<u>C</u>TWEVWGRE<u>C</u>-CONH2 | 4.5 |

[a]Disulfide bonds link the underlined cysteines.

Certain positions were additionally mutated to other amino acids to determine the range of similar amino acids that could be accommodated at each position (Table 13).

TABLE 13

Point mutations on key amino acids in $P_2$

| Name | SEQ ID NO: | Sequences[a] | $K_D/P_2 K_D$ |
|---|---|---|---|
| Substitutions at Thr-4 | | | |
| $P_{2-24}$ | 95 | H2N-DP<u>C</u>AWEVWGRE<u>C</u>LQ-GG-Par-G-CONH2 | 5.45 |
| $P_{2-25}$ | 96 | H2N-DP<u>C</u>VWEVWGRE<u>C</u>LQ-GG-Par-G-CONH2 | 1.10 |
| $P_{2-26}$ | 97 | H2N-DP<u>C</u>SWEVWGRE<u>C</u>LQ-GG-Par-G-CONH2 | 1.68 |
| $P_{2-27}$ | 98 | H2N-DP<u>C</u>-Par-WEVWGRE<u>C</u>LQ-CONH2 | 5.40 |
| Substitutions at Trp-5 | | | |
| $P_{2-28}$ | 99 | H2N-DP<u>C</u>TAEVWGRE<u>C</u>LQ-GG-Par-G-CONH2 | 62.49 |
| $P_{2-29}$ | 100 | H2N-DP<u>C</u>TFEVWGRE<u>C</u>LQ-GG-Par-G-CONH2 | 9.24 |
| Substitutions at Glu-6 | | | |
| $P_{2-30}$ | 101 | H2N-DP<u>C</u>TWAVWGRE<u>C</u>LQ-GG-Par-G-CONH2 | 2.89 |
| $P_{2-31}$ | 102 | H2N-DP<u>C</u>TW-Par-VWGRE<u>C</u>LQ-CONH2 | 0.86 |
| $P_{2-32}$ | 103 | H2N-DP<u>C</u>TWRVWGRE<u>C</u>LQ-GG-Par-G-CONH2 | 1.21 |
| $P_{2-33}$ | 104 | H2N-DP<u>C</u>TWGVWGRE<u>C</u>LQ-GG-Par-G-CONH2 | 42.69 |
| Substitutions at Val-7 | | | |
| $P_{2-34}$ | 105 | H2N-DP<u>C</u>TWEAWGRE<u>C</u>LQ-GG-Par-G-CONH2 | 5.79 |
| $P_{2-35}$ | 106 | H2N-DP<u>C</u>TWE-Par-WGRE<u>C</u>LQ-CONH2 | 5.69 |
| $P_{2-36}$ | 107 | H2N-DP<u>C</u>TWEIWGRE<u>C</u>LQ-GG-Par-G-CONH2 | 3.48 |
| $P_{2-37}$ | 108 | H2N-DP<u>C</u>TWELWGRE<u>C</u>LQ-GG-Par-G-CONH2 | 10.1 |
| $P_{2-38}$ | 109 | H2N-DP<u>C</u>TWETWGRE<u>C</u>LQ-GG-Par-G-CONH2 | 12.3 |
| Substitutions at Trp-8 | | | |
| $P_{2-39}$ | 110 | H2N-DP<u>C</u>TWEVAGRE<u>C</u>LQ-GG-Par-G-CONH2 | NB |
| $P_{2-40}$ | 111 | H2N-DP<u>C</u>TWEVFGRE<u>C</u>LQ-GG-Par-G-CONH2 | NS at 100 nm |
| Substitutions at Gly-9 | | | |
| $P_{2-41}$ | 112 | H2N-DP<u>C</u>TWEVWARE<u>C</u>LQ-GG-Par-G-CONH2 | NS at 100 nm |
| $P_{2-42}$ | 113 | H2N-DP<u>C</u>TWEVWaRE<u>C</u>LQ-GG-Par-G-CONH2 | NB |
| $P_{2-43}$ | 114 | H2N-DP<u>C</u>TWEVW-Sar-RE<u>C</u>LQ-GG-Par-G-CONH2 | NB |
| $P_{2-44}$ | 115 | H2N-DP<u>C</u>TWEVW-βA-RE<u>C</u>LQ-GG-Par-G-CONH2 | NB |

TABLE 13-continued

Point mutations on key amino acids in $P_2$

| Name | SEQ ID NO: | Sequences[a] | $K_D/P_2$ $K_D$ |
|---|---|---|---|
| | | Substitutions at Arg-10 | |
| $P_{2-45}$ | 116 | H2N-DP<u>C</u>TWEVWGAE<u>C</u>LQ-GG-Par-G-CONH2 | NS at 100 nm |
| $P_{2-46}$ | 117 | H2N-DP<u>C</u>TWEVWGKE<u>C</u>LQ-GG-Par-G-CONH2 | 13.94 |
| $P_{2-47}$ | 118 | H2N-DP<u>C</u>TWEVWG-F(pg)-E<u>C</u>LQ-GG-Par-G-CONH2 | 37.08 |
| | | Substitutions at Glu-11 | |
| $P_{2-48}$ | 119 | H2N-DP<u>C</u>TWEVWGAE<u>C</u>LQ-GG-Par-G-CONH2 | NS at 100 nm |
| $P_{2-49}$ | 120 | H2N-DP<u>C</u>TWEVWGRD<u>C</u>LQ-GG-Par-G-CONH2 | 3.39 |

[a]Disulfide bonds link the underlined cysteines.

Figure 14:
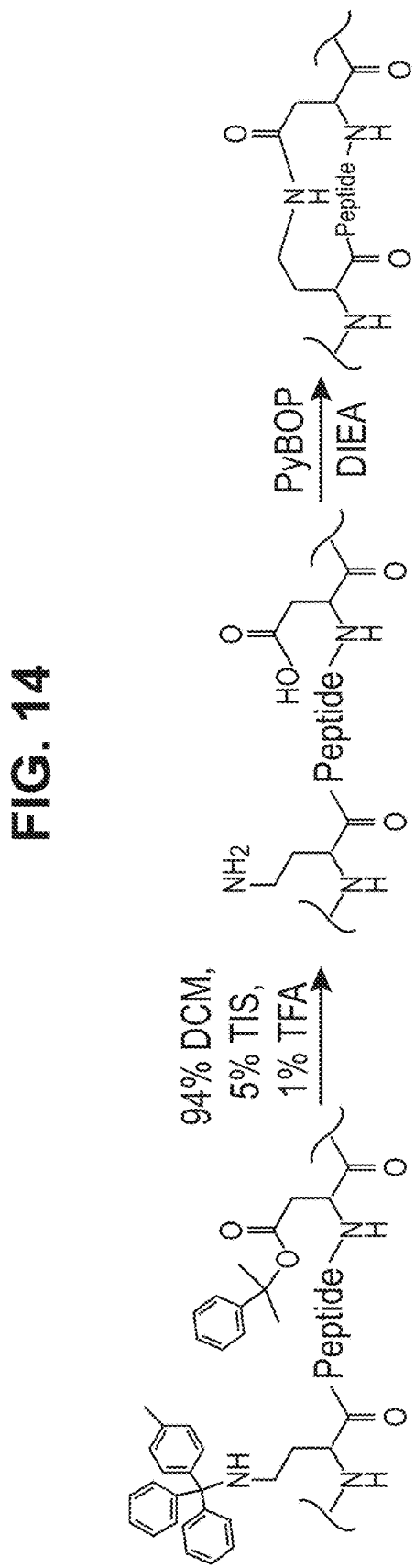
FIG. 14 depicts an example of internal amide bond formation between diaminobutyric acid (Dab) and aspartic acid residues.

As expected, the residues that were tolerant of an alanine substitution could likewise be changed to other amino acids with little impact on binding. To determine if the disulfide bridge could be modulated or replaced, a series of lactam and disulfide cyclized peptide analogs were generated. An example of internal amide bond formation between diaminobutyric acid (Dab) and aspartic acid residues is depicted in FIG. 14. All of the lactam cyclized peptides lost considerable activity indicating that the more polar amide bond cyclization was not well tolerated within the peptide structure (Table 14).

TABLE 14

Disulfide bond replacement with lactam cyclizations utilizing various amine and carboxylic acid-containing amino acids

| Name | SEQ ID NO: | Sequence | Result |
|---|---|---|---|
| | | Disulfide substitutions at Cys-3 and Cys-12 | |
| $P_{2-50}$ | 121 | H2N-DP<u>C</u>TWEVWGRE-<u>homoC</u>-LQ-GG-Par-G-CONH2 | 4.56 |
| $P_{2-51}$ | 122 | H2N-DP-<u>homoC</u>-TWEVWGRE<u>C</u>LQ-GG-Par-G-CONH2 | 8.88 |
| $P_{2-52}$ | 123 | H2N-DP-<u>homoC</u>-TWEVWGRE-<u>homoC</u>-LQ-GG-Par-G-CONH2 | 14.04 |
| $P_{2-53}$ | 124 | H2N-DP<u>C</u>TWEVWGRE-<u>Pen</u>-LQ-GG-Par-G-CONH2 | 2.64 |
| $P_{2-54}$ | 125 | H2N-DP-<u>Pen</u>-TWEVWGRE<u>C</u>LQ-GG-Par-G-CONH2 | 4.78 |
| $P_{2-55}$ | 126 | H2N-DP-<u>Pen</u>-TWEVWGRE-<u>Pen</u>-LQ-GG-Par-G-CONH2 | 1.18 |
| $P_{2-56}$ | 127 | H2N-DP-<u>homoC</u>-TWEVWGRE-<u>Pen</u>-LQ-GG-Par-G-CONH2 | >100 mM |
| | | Lactam substitutions[b] | |
| $P_{2-58}$ | 128 | H2N-GDP-<u>Orn</u>-TWEVWGRE<u>D</u>LQ-GG-Par-G-CONH2 | No binding |
| $P_{2-59}$ | 129 | H2N-GDP-<u>Dap</u>-TWEVWGRE<u>D</u>LQ-GG-Par-G-CONH2 | No binding |
| $P_{2-60}$ | 130 | H2N-GDP<u>K</u>TWEVWGRE<u>E</u>LQ-GG-Par-G-CONH2 | No binding |
| $P_{2-61}$ | 131 | H2N-GDP-<u>Orn</u>-TWEVWGRE<u>E</u>LQ-GG-Par-G-CONH2 | No binding |
| $P_{2-62}$ | 132 | H2N-GDP-<u>Dab</u>-TWEVWGRE<u>E</u>LQ-GG-Par-G-CONH2 | Not saturated at 17 μm |
| $P_{2-63}$ | 133 | H2N-GDP-<u>Dap</u>-TWEVWGRE<u>E</u>LQ-GG-Par-G-CONH2 | No binding |
| $P_{2-64}$ | 134 | H2N-GDP<u>D</u>TWEVWGRE<u>K</u>LQ-GG-Par-G-CONH2 | No binding |
| $P_{2-65}$ | 135 | H2N-GDP<u>D</u>TWEVWGRE-<u>Orn</u>-LQ-GG-Par-G-CONH2 | No binding |
| $P_{2-66}$ | 136 | H2N-GDP<u>D</u>TWEVWGRE-<u>Dap</u>-LQ-GG-Par-G-CONH2 | No binding |

TABLE 14-continued

Disulfide bond replacement with lactam cyclizations utilizing various amine and carboxylic acid-containing amino acids

| Name | SEQ ID NO: | Sequence | Result |
|---|---|---|---|
| $P_{2-67}$ | 137 | H2N-GGDP<u>E</u>TWEVWGRE<u>K</u>LQ-GG-Par-G-CONH2 | Not saturated at 100 μm |
| $P_{2-68}$ | 138 | H2N-GDP<u>E</u>TWEVWGRE-<u>Orn</u>-LQ-GG-Par-G-CONH2 | No binding |
| $P_{2-69}$ | 139 | H2N-GDP<u>E</u>TWEVWGRE-<u>Dap</u>-LQ-GG-Par-G-CONH2 | No binding |

[b]Lactam bonds link the underlined amino acids.

Figure 15:
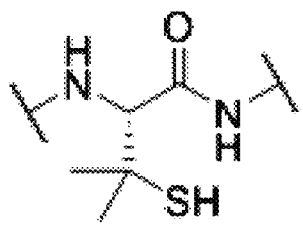
FIG. 15 shows structures of penicilamine (pen) and homocysteine (homocys).
Figure 15:
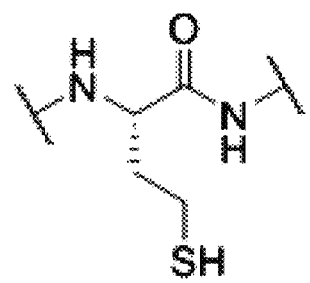
Figure 16:
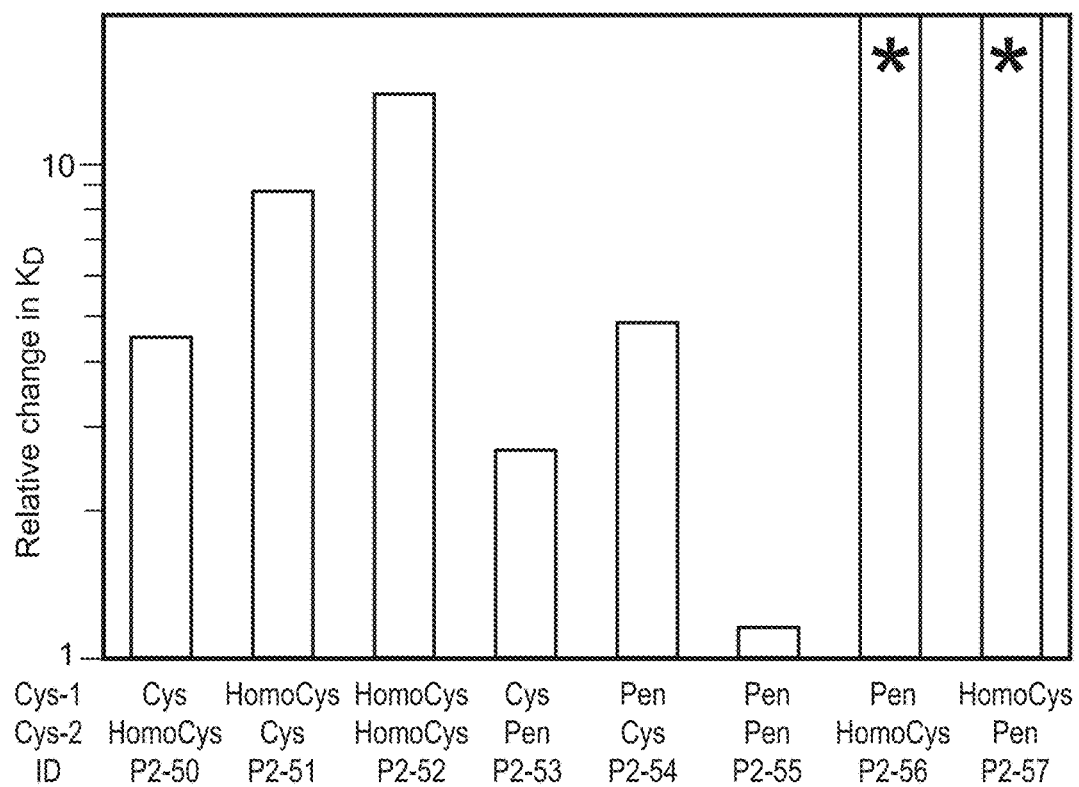
FIG. 16 depicts alternative disulfide variants of $P_2$. The Cys replacement is indicated for each of the two positions (Cys3 or Cys12) and the relative affinity as measured by SPR is compared to the $K_D$ of the parent peptide ($P_2$). *Value is higher than it appears in graph.

Replacing the Cys-Cys disulfide with other disulfide bonds generated analogs with varying degrees of binding. Selected cysteine analogs are depicted in FIG. 15, and effects of cysteine analogs on binding are depicted in FIG. 16 and Table 14. Inclusion of homocysteine (homocys), which has an additional methylene between the backbone and the disulfide, appeared to be detrimental to binding, suggesting that a larger macrocycle was not favored. Inclusion of penicillamine (pen) was tolerated only in combination with Cys, however the PenPen analog was comparable in affinity to the parent Cys-Cys peptide.

In an attempt to improve binding affinity, the critical aromatic residues for peptide binding were individually replaced with various aromatic amino acids (Table 15). Since the aromatic residues mediate key contacts with EGFR, it may be possible to enhance binding by introducing alternative functional groups that have improved or additional contacts with the receptor. Phenylalanine replacement at the less critical tryptophan residue retained some of the binding, however, at the more critical Trp8 position phenylalanine was not tolerated. Each tryptophan was also replaced individually with 15 un-natural amino acids. Of these, one amino acid at each position demonstrated slightly improved affinity. The 2-indanoyl-glycine residue at position 5 was able to achieve slightly enhanced binding relative to tryptophan, however binding was completely abolished with this residue at position 8. At position 8, 5-methoxy tryptophan was approximately two fold better than tryptophan, however, synthesis of this amino acid at position 5 was unsuccessful.

TABLE 15

Substitution of unnatural aromatic amino acids for tryptophan 5 and 8

| R Name | R Structure | Position W5 | Position W8 | Peptide ID | $K_D$ Relative to $P_2$ |
|---|---|---|---|---|---|
| Phenyl-alanine | | R | Trp | $P_{2-70}$ | 9.24 |
| | | Trp | R | $P_{2-71}$ | >100 |
| 2-Pyridyl Alanine-1 | | R | Trp | $P_{2-72}$ | ** |
| | | Trp | R | $P_{2-73}$ | >100 |
| 3-Pyridyl Alanine-1 | | R | Trp | $P_{2-74}$ | 11.8 |
| | | Trp | R | $P_{2-75}$ | >100 |
| 4-Pyridyl Alanine-1 | | R | Trp | $P_{2-76}$ | >100 |
| | | Trp | R | $P_{2-77}$ | >100 |
| 1-Naphthyl Alanine-1 | | R | Trp | $P_{2-78}$ | >100 |
| | | Trp | R | $P_{2-79}$ | 42.9 |
| 2-Naphthyl Alanine-1 | | R | Trp | $P_{2-80}$ | >100 |
| | | Trp | R | $P_{2-81}$ | >100 |
| 4-Nitro Phenyl-alanine-1 | | R | Trp | $P_{2-82}$ | >100 |
| | | Trp | R | $P_{2-83}$ | >100 |
| 4-Trifluoromethyl Phenyl-alanine-1 | | R | Trp | $P_{2-84}$ | >100 |
| | | Trp | R | $P_{2-85}$ | >100 |

TABLE 15-continued

Substitution of unnatural aromatic amino acids for tryptophan 5 and 8

| R Name | R Structure | Position W5 | Position W8 | Peptide ID | $K_D$ Relative to $P_2$ |
|---|---|---|---|---|---|
| 4-Amino Phenyl-alanine-1 | | R Trp | Trp R | $P_{2\text{-}86}$ $P_{2\text{-}87}$ | 9 ** |
| Pentafluoro Phenyl-alanine-1 | | R Trp | Trp R | $P_{2\text{-}88}$ $P_{2\text{-}89}$ | 8.5 >100 |
| 3-Benzo-thienyl Alanine-1 | | R Trp | Trp R | $P_{2\text{-}90}$ $P_{2\text{-}91}$ | 1.6 123.5 |
| 2-Thienyl Alanine-1 | | R Trp | Trp R | $P_{2\text{-}92}$ $P_{2\text{-}93}$ | 15.9 >100 |
| Homo-phenyl-alanine-1 | | R Trp | Trp R | $P_{2\text{-}94}$ $P_{2\text{-}95}$ | 9.1 >100 |
| Diphenyl-alanine-1 | | R Trp | Trp R | $P_{2\text{-}96}$ $P_{2\text{-}97}$ | 8.9 >100 |
| 2-Indanyl Glycine-1 | | R Trp | Trp R | $P_{2\text{-}98}$ $P_{2\text{-}99}$ | 0.3 >100 |
| 5-Methoxy Tryptophan-1 | | R Trp | Trp R | $P_{2\text{-}100}$ $P_{2\text{-}101}$ | ** 0.5 |

Figure 17:
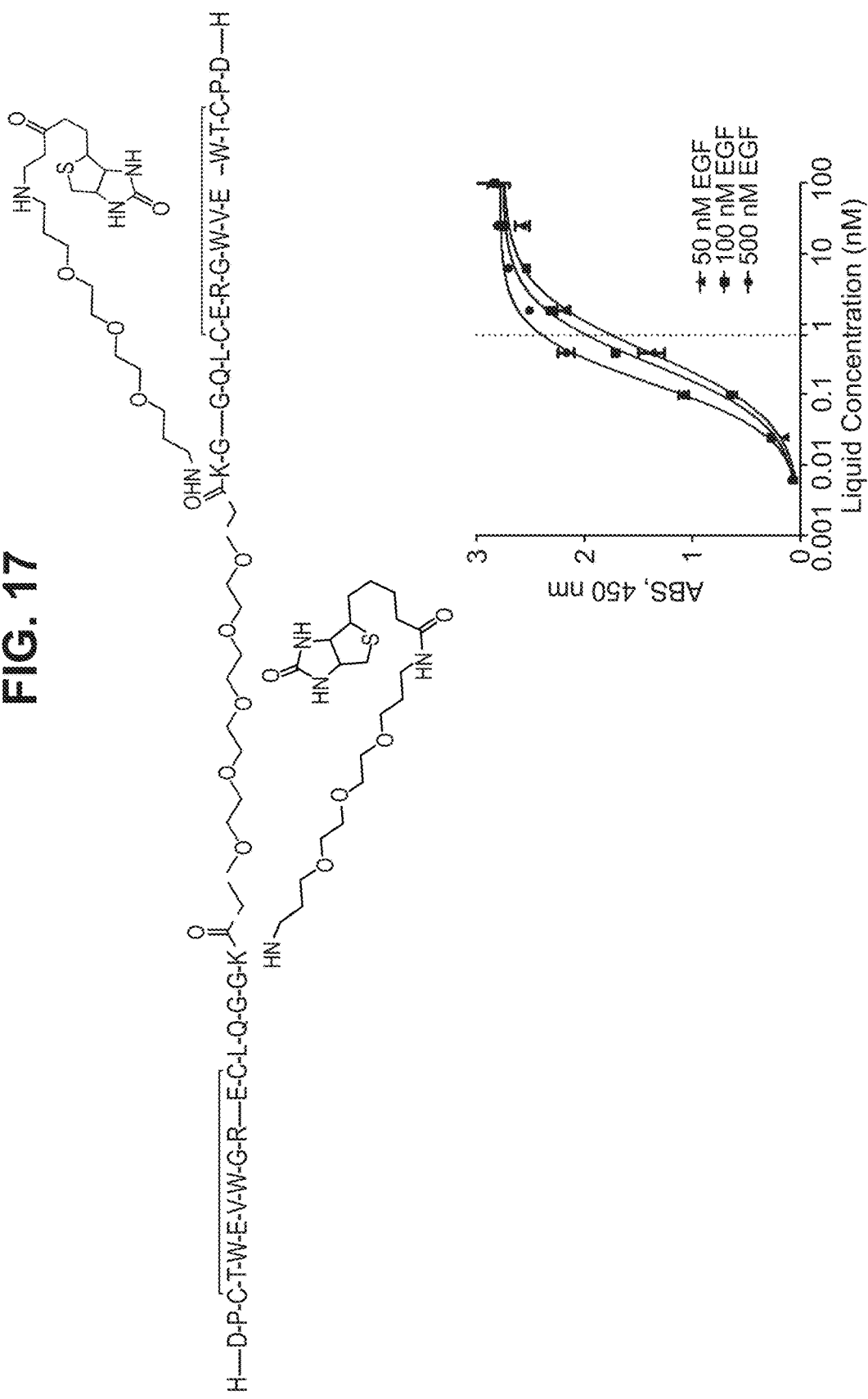
FIG. 17 depicts a $P_2$-Biotin dimer (top) and shows the dependence of biotinylated $P_2$ derivative binding on EGF concentration (bottom). Figure discloses SEQ ID NOS 200 and 200, respectively, in order of appearance.
Figure 18:
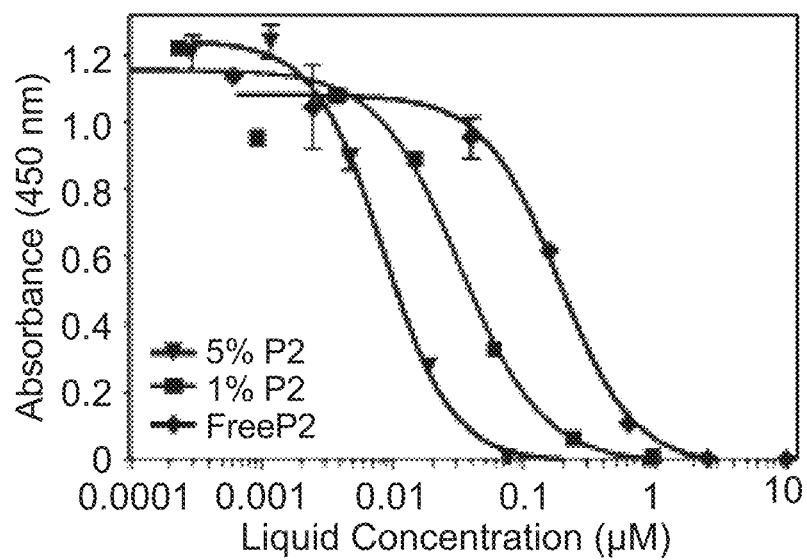
FIG. 18 depicts $P_2$ competition assay results comparing free $P_2$ to 1 and 5% $P_2$-conjugated nanoparticles.
Figure 19:
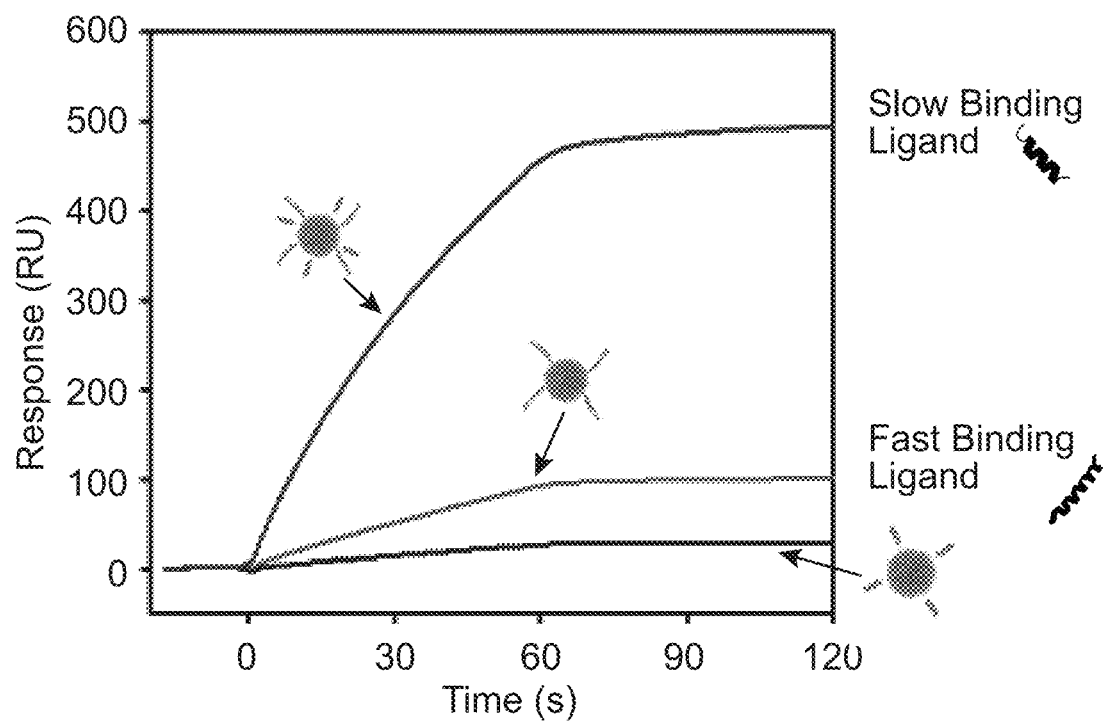
FIG. 19 depicts synergistic NP binding from ligands with distinct kinetic profiles.

An additional assay was developed to provide an orthogonal assay to SPR during the evaluation of the $P_2$ peptide analogs and nanoparticle conjugates. Since these peptides are not competitive with EGF, a novel biotinylated, dimeric form of $P_2$ was synthesized (FIG. 17). This peptide in the presence of EGF is a good tracer for use in a competition ELISA format. FIG. 18 shows the results from competing free peptide $P_2$ or NP conjugates at 1 or 5% ligand density. Notably, $P_2$ demonstrated improved EGFR binding on a molar basis when conjugated to the nanoparticle, which is in contrast to the natural ligand EGF which decreased slightly in affinity. Conjugation to the nanoparticle, and the resulting decrease in off rate due to multivalent binding, is probably more impactful to the peptide ligand which has a fast on and off rate than to the EGF ligand which has a high affinity binding resulting from a fast on and slow off rate. The combination of ligands with distinct kinetic profiles can yield synergistic nanoparticle binding (FIG. 19).

Figure 20:
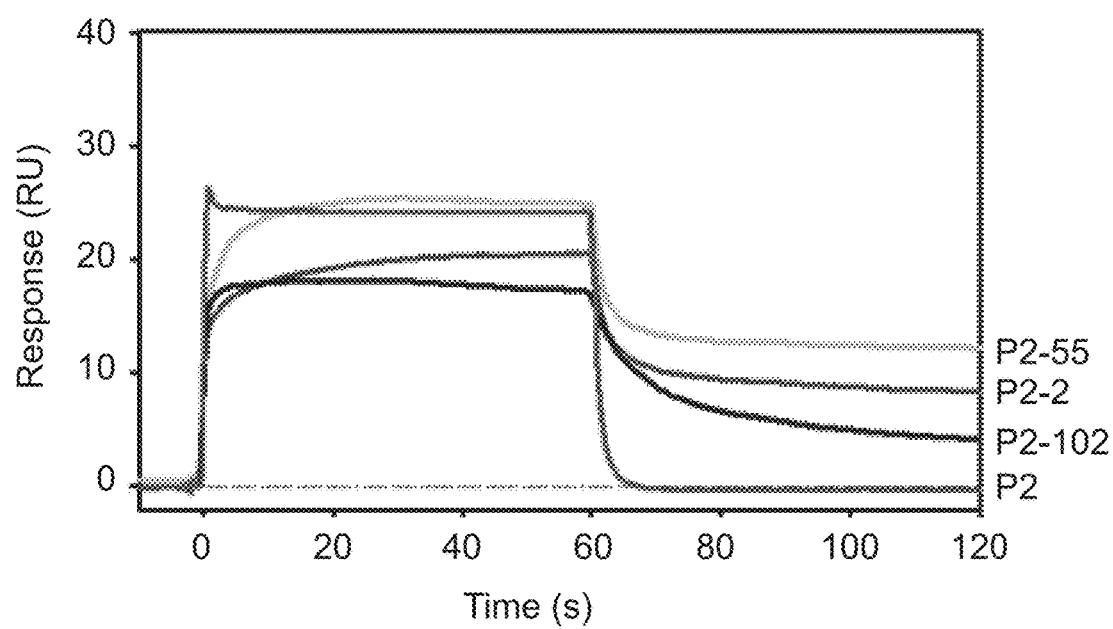
FIG. 20 shows binding of optimized $P_2$ analogs by SPR at 3.2 µM.

Of the many analogs that were generated in the structure activity relationship work, three were further evaluated. These three peptides ($P_{2\text{-}2}$, $P_{2\text{-}102}$, and $P_{2\text{-}55}$) were synthesized as DBCO conjugates and compared to the parent peptide ($P_2$). The two aromatic mutations $P_{2\text{-}98}$ and $P_{2\text{-}101}$ were combined into one peptide ($P_{2\text{-}102}$). $P_{2,2}$ was generated from the alanine scan series and $P_{2\text{-}55}$ incorporated Pen-Pen cyclization. SPR analysis, depicted in FIG. 20, of these three analogs showed all three exhibiting improved affinity relative to the parent peptide ($P_{2\text{-}2}$, $P_{2\text{-}102}$, $P_{2\text{-}55}$ compared to $P_2$). Once again, the $K_D$ in the presence or absence of EGF was not significantly different (Table 16).

TABLE 16

SPR analysis of binding affinity for $P_2$ and analogs that incorporate the alanine, pen and aromatic substitutions, and SPR analysis of the hybrid peptide ligands.

| Ligand | SEQ ID NO: | Sequence | $K_D$ - EGF (nM) | $K_D$ + EGF (nM) |
|---|---|---|---|---|
| $P_2$ | 140 | Ac-DPCTWEVWGRECLQGGK(PEG4-DBCO)-CONH2 | 240 ± 30 | 170 ± 60 |
| $P_{2\text{-}2}$ | 141 | Ac-DACTWEVWGRECLQGGK(PEG4-DBCO)-CONH2 | 29 ± 10 | 54 ± 21 |
| $P_{2\text{-}102}$ | 142 | Ac-DPCT(2Ind)GEV(5MeO)WGRECLQGGK(PEG4-DBCO)-CONH2 | 38 ± 14 | 32 ± 13 |
| $P_{2\text{-}55}$ | 143 | Ac-DPPenTWEVWGREPenLQGGK(PEG4-DBCO)-CONH2 | 74 ± 14 | 69 ± 24 |
| $P_{2\text{-}2/55}$ | 144 | Ac-DAPenTWEVWGREPenLQGGK(DBCO)-CONH2 | 137 ± 56 | 97 ± 7 |
| $P_{2\text{-}2/102}$ | 145 | Ac-DACT(2Ind)GEV(5MeO)WGRECLQGGK(DBCO)-CONH2 | 23.8 ± 4.5 | 23.3 ± 0.3 |

TABLE 16-continued

SPR analysis of binding affinity for P$_2$ and analogs that incorporate the alanine, pen and aromatic substitutions, and SPR analysis of the hybrid peptide ligands.

| Ligand | SEQ ID NO: | Sequence | K$_D$ - EGF (nM) | K$_D$ + EGF (nM) |
|---|---|---|---|---|
| P$_{2-55/102}$ | 146 | Ac-DPPenT(2Ind)GEV(5MeO)WGREPenLQGGK(DBCO)-CONH2 | 72.0 ± 4.8 | 75.4 ± 1.4 |
| P$_{2-2/55/102}$ | 147 | Ac-DAPenT(2Ind)GEV(5MeO)WGREPenLQGGK(DBCO)-CONH2 | 53 ± 26 | 33.4 ± 2.9 |

Nanoparticle conjugates of these three analogs were prepared at 1% and 5% ligand density and evaluated by SPR and/or P$_2$ competition ELISA. Rather than trying to fit the sensorgram data to derive K$_D$s, the SPR data was converted to a "snapshot" plot that represents the concentration-dependent binding response observed after 2 minutes injection (FIGS. 21A, 21B). Sensorgram response data for these plots was normalized to take into account experimental differences in capture level. Comparison of the capture normalized responses for the parent P$_2$ conjugated nanoparticle (5%) to the new analogs all at 5% ligand density revealed a modest improvement in binding for all three analogs in the absence of EGF, a modest improvement for the alanine and aromatic analogs, and a substantial increase in binding for the Pen analog in the presence of EGF (FIG. 21C). Penicillamine contains gem-dimethyl groups on the beta carbon of the amino acid, which reduces conformational flexibility. Given that this peptide did not display superior binding affinity as a free ligand relative to the other analogs, it may be that this more rigid peptide structure has altered the binding kinetics, which may have an impact on nanoparticle binding.

single peptide sequences were synthesized and evaluated as free ligands and as nanoparticle conjugates. Analysis of the K$_D$ of the free ligands reveals moderate impacts on affinity. In general, inclusion of the aromatic residues appears to improve affinity and all of the free ligand affinities were insensitive to the presence of EGF (Table 16).

Figure 22:
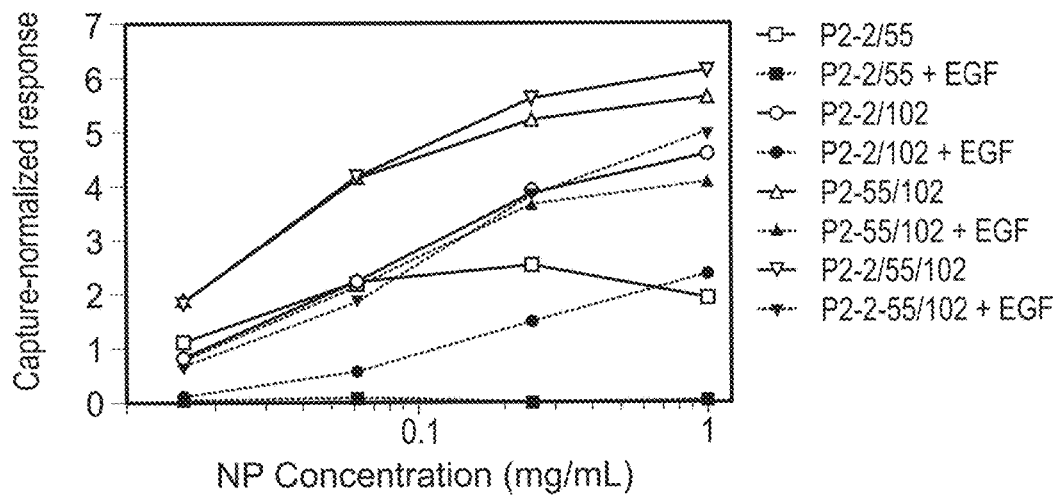
FIG. 22 shows relative binding of nanoparticles conjugated to nanoparticles bearing $P_2$ analogs with two or three amino acid substitutions at 5% ligand density in the presence and absence of EGF as measured by SPR.

Nanoparticle conjugates of the hybrid peptides by contrast demonstrate some significant differences in binding. FIG. 22 shows SPR snapshot plots of the three double and one triple mutant. The most striking trend is that inclusion of the aromatic residues dramatically improves binding of the nanoparticle conjugates to EGFR in the absence of EGF binding. The combination of Ala2 and Pen appears to have a negative impact on binding. This is highlighted by comparing the double mutant that only contains the Pen and Ala2 substitutions (P$_{2-2155}$) to those that contain the aromatic substitutions. This nanoparticle exhibits moderate EGFR binding in the presence of EGF, however very low binding to the receptor alone. All nanoparticles that contain the aromatic substitutions exhibit minimal change of binding upon EGF binding and the double and triple mutant ligands with aromatic substitutions exhibit improved overall nanoparticle binding.

TABLE 17

ELISA analysis of binding affinity for P$_2$ and analogs that incorporate the alanine, pen and aromatic substitutions.

| | | | 5% Ligand Density NP | | 1% Ligand Density NP | |
|---|---|---|---|---|---|---|
| Ligand | SEQ ID NO: | Sequence | IC$_{50}$ (μg/mL) | Rel IC$_{50}$ | IC$_{50}$ (μg/mL) | Rel IC$_{50}$ |
| P$_2$ | 148 | Ac-DPCTWEVWGRECLQGGK(PEG4-DBCO)-CONH2 | 4.3 | Ref | 81 | Ref |
| P$_{2-2}$ | 149 | Ac-DACTWEVWGRECLQGGK(PEG4-DBCO)-CONH2 | 3 | 0.7 | 17 | 0.2 |
| P$_{2-102}$ | 150 | Ac-DPCT(2Ind)GEV(5MeO)WGRECLQGGK(PEG4-DBCO)-CONH2 | 2.6 | 0.6 | 7.6 | 0.09 |
| P$_{2-55}$ | 151 | Ac-DPPenTWEVWGREPenLQGGK(PEG4-DBCO)-CONH2 | 3.4 | 0.79 | 135 | 1.67 |

ELISA data is depicted in Table 17. P$_2$ competition ELISA results were consistent with the SPR data. EGF is required in the P$_2$ ELISA for high-affinity binding of the tracer, therefore nanoparticle binding cannot be assessed +/−EGF. The results indicate a modest improvement in affinity for all three analog-conjugates at 5% ligand density.

Given there were modest improvements with all three analogs as nanoparticle conjugates, hybrid sequences that incorporate the features of two or all three analogs into The P$_2$ competition ELISA, depicted in Table 18, demonstrated a similar result, with the Ala2-Pen being relatively unchanged compared to the parent peptide-nanoparticle conjugate at 5%, while the hybrid analogs containing the aromatic substitutions had lower IC$_{50}$ values. While the ligands containing the aromatic residues had improved affinity relative to the original parent peptide, they are not substantially different from the peptides with the single substitutions (Tables 16). Therefore, the clear improvements in nanoparticle binding cannot be explained merely by ligand affinity.

TABLE 18

ELISA binding analysis of 5% hybrid peptide ligand conjugated nanoparticles

| Ligand | SEQ ID NO: | Sequence | IC$_{50}$ (µg/mL) | Rel. Diff. |
|---|---|---|---|---|
| P$_2$ | 152 | Ac-DPCTWEVWGR ECLQGGK(PEG5-DBCO)-CONH2 | 6 | Ref |
| P$_{2-2/55}$ [DA PenPen] | 153 | Ac-DAPenTWEVW GREPenLQGGK (DBCO)-CONH2 | 6.3 | 1.05 |
| P$_{2-2/102}$ [DA Aro] | 154 | Ac-DACT(2Ind) GEV(5MeO)WGRE CLQGGK(DBCO)-CONH2 | 3.7 | 0.62 |
| P$_{2-55/102}$ [Aro PenPen] | 155 | AcDPPenT(2Ind) GEV(5MeO)WGRE PenLQGGK(DBCO)-CONH2 | 2.2 | 0.37 |
| P$_{2-2/55/102}$ [DA Aro PenPen] | 156 | AcDAPenT(2Ind) GEV(5MeO)WGRE PenLQGGK(DBCO)-CONH2 | 1.6 | 0.27 |

Example 9

Flow Cytometry Analysis

Peptide nanoparticle conjugates incorporating PLA-Cy5 were evaluated further for binding to EGFR expressed on the surface of human epithelial carcinoma A$_{431}$ cells by flow cytometry. Nanoparticles were incubated with A$_{431}$ cells at 4° C. in the presence or absence of EGF and then washed to remove any unbound nanoparticles. Nanoparticle binding was analyzed in a flow cytometer. At 4° C., EGFR receptor internalization is minimized and the observed signal is predominantly due to cell surface binding.

Figure 23A:
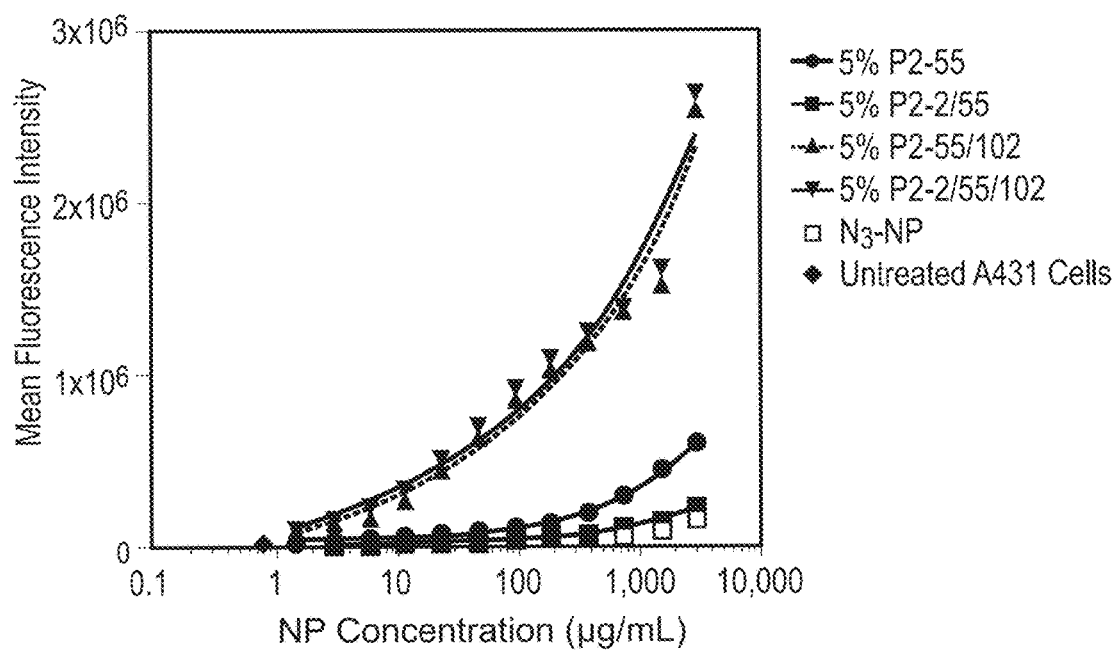
FIGS. 23A-23C depict EGFR-targeting nanoparticles binding $A_{431}$ cells without EGF (FIG. 23A) and with 50-nM EGF (FIG. 23B).
Figure 23B:
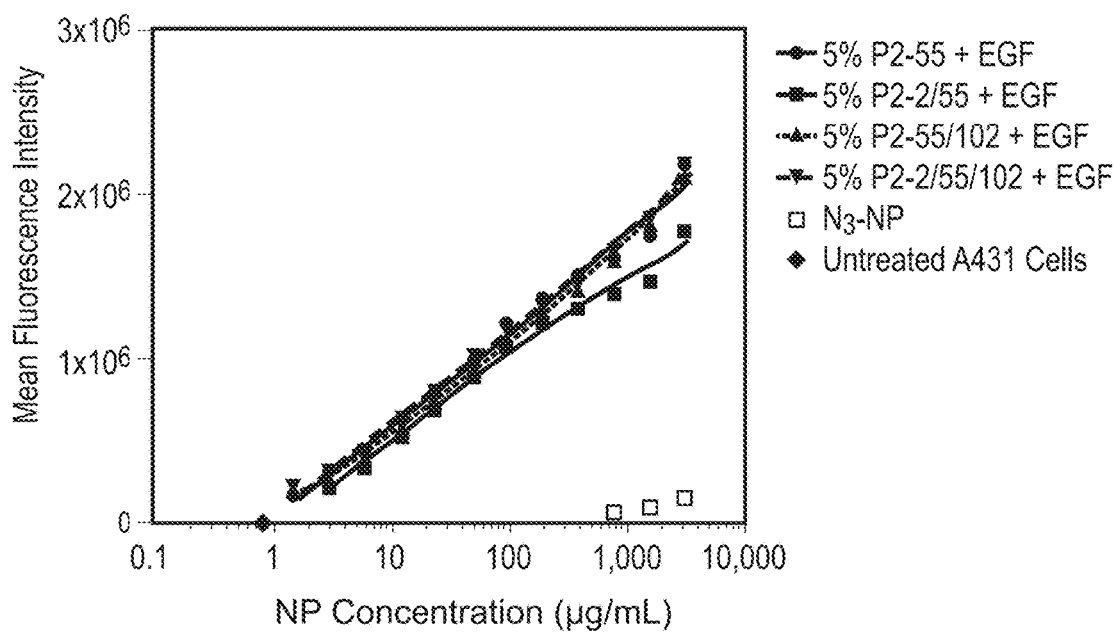
Figure 23C:
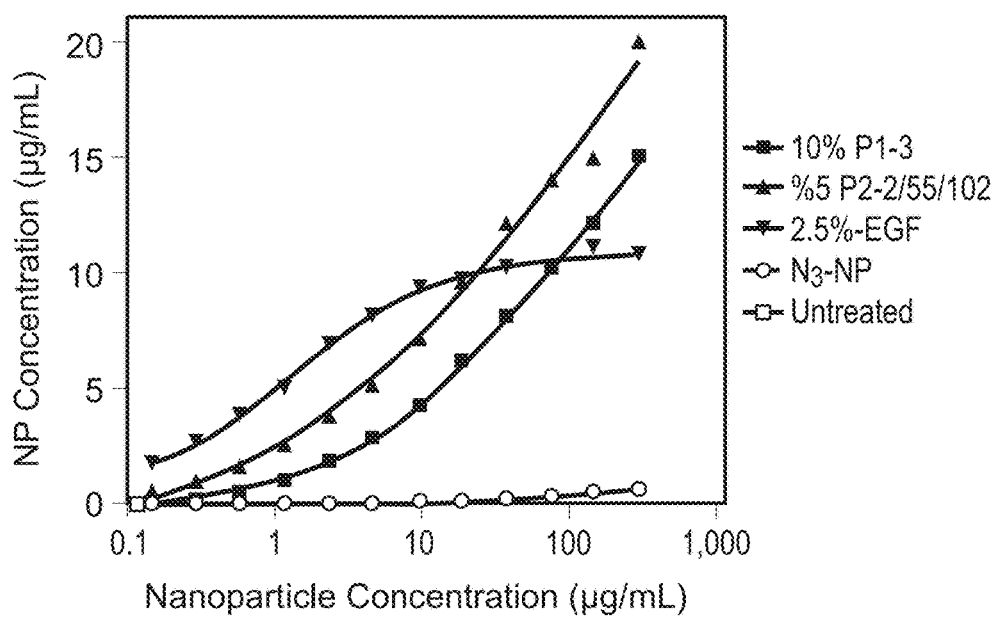
Figure 24:
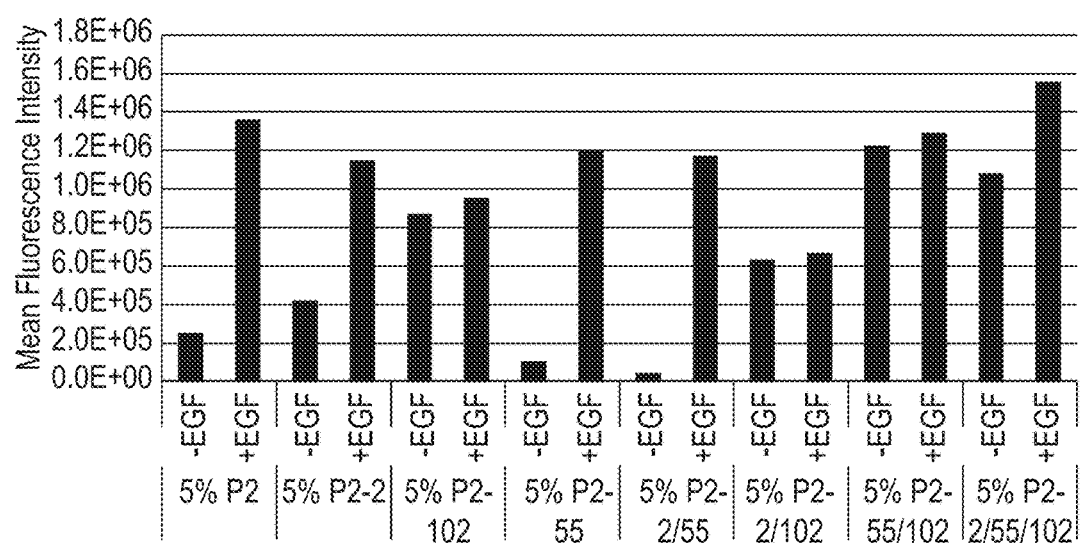
FIG. 24 shows relative binding of the indicated nanoparticles as assayed by flow cytometry.

FIGS. 23A-23C shows representative data from the flow cytometry experiments, and the complete data is depicted in FIG. 24. In FIGS. 23A and 23B, binding curves for nanoparticle-conjugates with the Pen substitution are compared. While all the conjugates bind well in the presence of EGF, only the Pen/aromatic and triple mutant bind well in the absence of EGF. There is a high degree of agreement between the summary plot of the cell binding data and the summary plot from FIG. 22 of the SPR data. The double mutant containing the penicillamines and the aromatics, as well as the triple mutant, were the strongest binding nanoparticles and in particular exhibited near equivalent binding in the presence or absence of EGF.

The EGF, P$_{1-3}$, and triple hybrid nanoparticle conjugates were compared directly (FIG. 23C). While not tested at equivalent ligand loadings, the results demonstrate that the ligand selection and optimization approach has led to the generation of two nanoparticle conjugates that are capable of binding EGFR expressing cells to a similar extent as nanoparticles conjugated to the relatively high-affinity, naturally occurring ligand for EGFR.

Figure 25A:
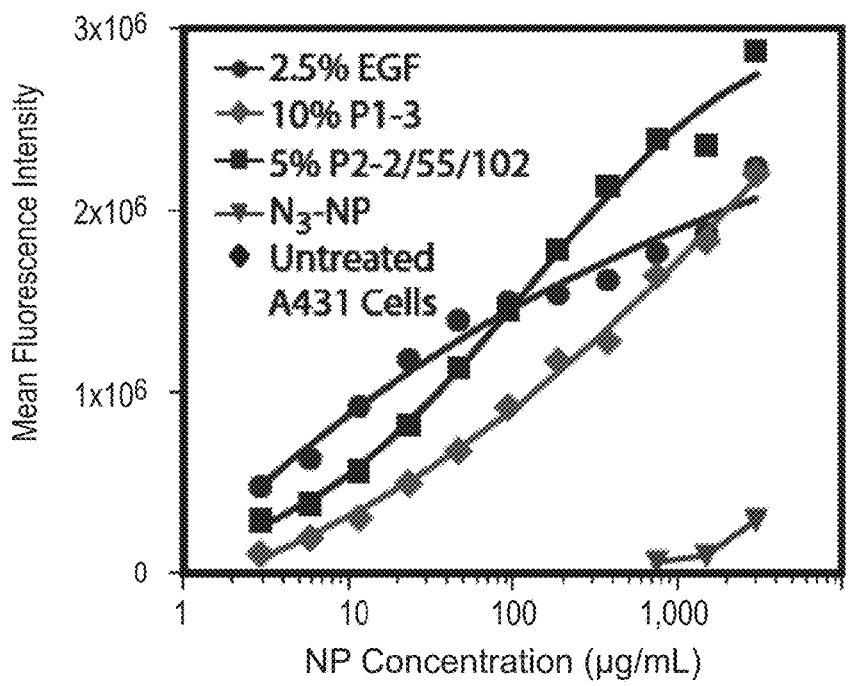
FIGS. 25A-25B depict total binding and internalization of EGF, $P_{1-3}$ and $P_{2/55/102}$ nanoparticles at 37° C. to $A_{431}$ cells (FIG. 25A), and the rate of internalization of targeted nanoparticles (FIG. 25B).
Figure 25B:
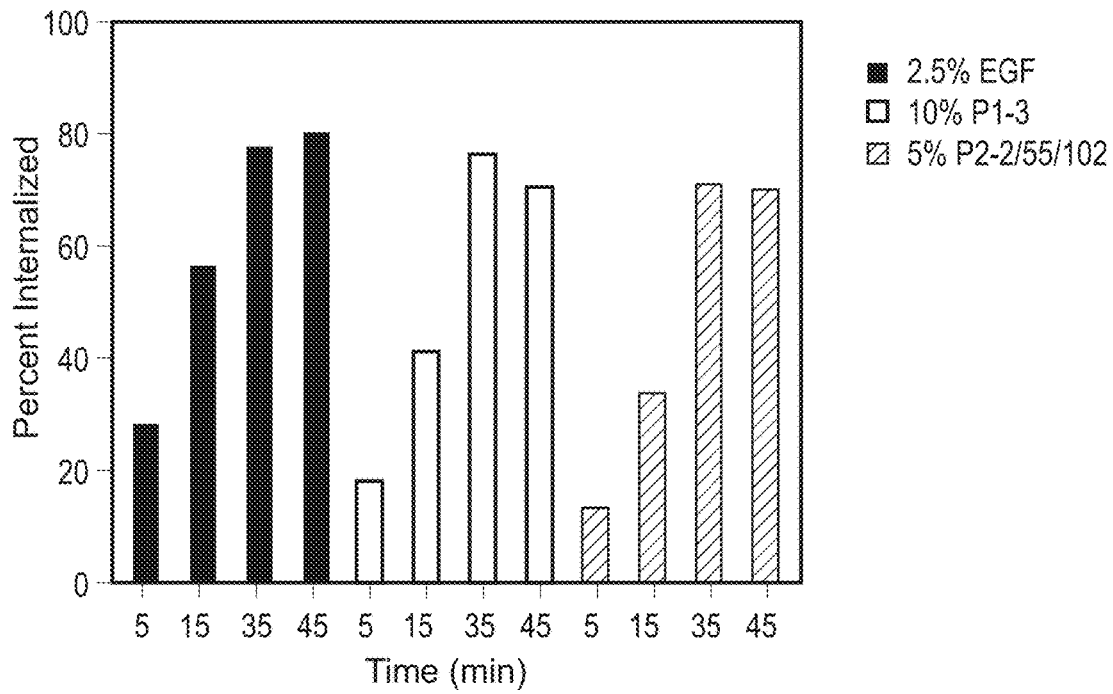

These ligands and nanoparticle conjugates were screened and optimized using SPR at room temperature and flow cytometry at 4° C. Despite the relatively strong correlation of the SPR and flow cytometry data, since we intend to evaluate these nanoparticles in vivo, we therefore assessed their binding at physiological temperature. We evaluated the binding and internalization of the nanoparticles at 37° C. to A$_{431}$ cells. Total bound nanoparticles, including surface-bound and internalized particles, were assessed after 30 minutes of incubation (FIG. 25A). A portion of each sample was then treated with acid to remove surface bound nanoparticles. The remaining fluorescent signal associated with the nanoparticles represents the internalized fraction (FIG. 25B). Interestingly, all three nanoparticles were found to bind and internalize efficiently with 30-60% internalization by 30 minutes.

Example 10

Peptide and Nanoparticle Characterization

The particle size and zeta potential of select functionalized and non-functionalized nanoparticles is depicted in Table 19, and the expected and observed molecular weight of selected peptides and peptide-DBCO conjugates depicted in Table 20.

TABLE 19

Nanoparticle size and zeta potential

| Ligand | Size of Base 30% Azide Particle | Size | Size Change | Zeta Potential |
|---|---|---|---|---|
| 2.5% EGF | 106.6 | 108.1 | +1.5 | −10.3 |
| 10% P$_1$ | 106.6 | 100.3 | −6.3 | −10.4 |
| 5% P$_1$ | 73.2 | 78.7 | +5.5 | −17.1 |
| 10% P$_{1-3}$ | 106.6 | 105.9 | −0.7 | −17.1 |
| 5% P$_{1-3}$ | 73.2 | 78.2 | +5.0 | NT |
| 10% P$_2$ | 106.6 | 101.5 | −5.1 | −22.3 |
| 5% P$_2$ | 106.6 | 96.3 | −10.3 | −11.4 |
| 5% P$_{2-55}$ | 106.6 | 104.7 | −1.9 | NT |
| 5% P$_{2-2}$ | 106.6 | 122.6 | +16.0 | NT |
| 5% P$_{2-102}$ | 106.6 | 88.7 | −17.9 | NT |
| 5% P$_{2-2/55}$ | 106.6 | 87.2 | −19.4 | NT |
| 5% P$_{2-2/102}$ | 106.6 | 89.0 | −17.6 | NT |
| 5% P$_{2-55/102}$ | 106.6 | 84.8 | −21.8 | NT |
| 5% P$_{2-2/55/102}$ | 106.6 | 104.0 | −2.6 | −8.1 |
| 30% N$_3$-NP | — | 106.6 | — | −11.7 |
| 30% N$_3$-NP | — | 73.2 | — | NT |
| 100% PEG-NP | — | 105.1 | — | −9.2 |

TABLE 20

Expected and observed molecular weight of selected peptides and conjugates

| Peptide ID | SEQ ID NO: | Sequence | Calculated MW (Da) | MW Observed Deconvoluted (Da) | Observed m/z ions |
|---|---|---|---|---|---|
| 1 | 157 | SECFPLAPDWLSCIL | 1691 | 1691.2 | 846.6 |
| 2 | 158 | DPCTWEVWGRECLQ | 1718.9 | 1718 | 860 |

TABLE 20-continued

Expected and observed molecular weight of selected peptides and conjugates

| Peptide ID | SEQ ID NO: | Sequence | Calculated MW (Da) | MW Observed Deconvoluted (Da) | Observed m/z ions |
|---|---|---|---|---|---|
| 3 | 159 | TDCVIFGLETYCLR | 1629.9 | 1629 | 815.5 |
| 4 | 160 | SGCLDALWQCVY | 1354.6 | 1354.8 | 678.4 |
| 5 | 161 | LPDDSLPELICKVR | 1653.9 | 1653.2 | 827.6 |
| 6 | 162 | GPCVLIRDYYLLCLE | 1767.1 | 1767 | 884.49 |
| 7 | 163 | VLCHRYYHPICYT | 1664.9 | 1664.2 | 833.1 |
| 8 | 164 | MFCFRWYAGWSCVS | 1740.1 | 1740 | 871 |
| 9 | 165 | HFYPTKTPGY | 1209.4 | 1208.8 | 605.4 |
| 10 | 166 | AASRALWAFNSD | 1307.5 | 1307 | 654.5 |
| 11 | 167 | SYYWGYTVDIRR | 1577.8 | 1577 | 789.5 |
| 12 | 168 | KTCVSTTFDLWFVCFA | 1867.22 | NS | NS |
| 13 | 169 | YHWYGYTPQNVI | 1539.7 | 1539.2 | 770.6 |
| 14 | 170 | LARLLT | 684.9 | 684.6 | 343.3 |
| 15 | 171 | CEHGAMEIC | 989.2 | 990.6 | 496.3 |
| 16 | 172 | AKFNDYWRW | 1284.5 | 1283.8 | 642.9 |
| 17 | 173 | CPAKFSPSVC | 1035.3 | 1036.8 | 519.4 |
| 18 | 174 | YCPIWKFPDEECY | 1688.7 | 1689 | 845.5 |
| $P_1$ | 175 | Ac-SECFPLAPDWLSCILGGK(DBCO)-CONH2 | 2554 | 2553.6 | 1277.8, 852.2 |
| $P_{1-3}$ | 176 | Ac-SECFPAAPDWLSCILGGK(DBCO)-CONH2 | 2511.9 | 2511.6 | 1256.8, 838.2 |
| $P_2$ | 177 | Ac-DPCTWEVWGRECLQGGK(DBCO)-CONH2 | 2581.9 | 2581.6 | 1291.8, 861.5 |
| $P_{2-2}$ | 178 | Ac-DACTWEVWGRECLQGGK(DBCO)-CONH2 | 2555.9 | 2555.6 | 1278.8, 852.9 |
| $P_{2-55}$ | 179 | Ac-DP-Pen-TWEVWGRE-Pen-LQGGK(DBCO)-CONH2 | 2638 | 2637.6 | 1319.8, 880.2 |
| $P_{2-102}$ | 180 | Ac-DPCT-(2Ind)G-EV-(5MeO)W-GRECLQGGK(DBCO)-CONH2 | 2598.9 | 2598.6 | 1300.3, 867.2 |
| $P_{2-2/55}$ | 181 | Ac-DA-Pen-TWEVWGRE-Pen-LQGGK(DBCO)-CONH2 | 2567.9 | 2567.2 | 1284.6, 856.7 |
| $P_{2-2/102}$ | 182 | Ac-DACT-(2Ind)G-EV-(5MeO)W-GRECLQGGK(DBCO)-CONH2 | 2528.4 | 2528.2 | 1265.1, 843.7 |
| $P_{2-55/102}$ | 183 | Ac-DP-Pen-T-(2Ind)G-EV-(5MeO)W-GRE-Pen-LQGGK(DBCO)-CONH2 | 2655 | 2654.4 | 1328.2, 885.8 |
| $P_{2-2/55/102}$ | 184 | Ac-DA-Pen-T-(2Ind)G-EV-(5MeO)W-GRE-Pen-LQGGK(DBCO)-CONH2 | 2629 | 2628.6 | 1315.3, 877.2 |

EQUIVALENTS

Those skilled in the art will recognize, or be able to ascertain using no more than routine experimentation, many equivalents to the specific embodiments of the disclosed nanoparticle described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

What is claimed is:

1. A therapeutic nanoparticle, comprising:
   about 0.2 to about 35 weight percent of a therapeutic agent; and
   about 50 to about 98 weight percent of a diblock poly(lactic)acid-poly(ethylene)glycol copolymer or a diblock poly(lactic)-co-poly(glycolic)acid-poly(ethylene)glycol copolymer; and
   about 2% to about 12% PLA-PEG-EGFR ligand density, wherein the EGFR ligand is bound or associated to an azide functionalized PEG-PLA, wherein PLA is poly(lactic)acid and PEG is poly(ethylene)glycol; and wherein the EGFR ligand is a peptidyl ligand comprising a sequence selected from the group consisting of: Ac-DPCTWEVWGRECLQGGK(PEG4-DBCO)-CONH2 (SEQ ID NO: 185), Ac-DACTWEVWGRECLQGGK(PEG4-DBCO)-CONH2 (SEQ ID NO: 186), Ac-DPCT(2Ind)GEV(5MeO)WGRECLQGGK(PEG4-DBCO)-CONH2(SEQ ID NO: 187), Ac-DPPenTWEVWGREPenLQGGK(PEG4-DBCO)-CONH2 (SEQ ID NO: 188), AcDAPenTWEVWGREPenLQGGK(DBCO)-CONH2 (SEQ ID NO: 189), Ac-DACT(2Ind)GEV(5MeO)WGRECLQGGK(DBCO)-CONH2 (SEQ ID NO: 190), Ac-DPPenT(2Ind)GEV(5MeO)WGREPenLQGGK(DBCO)-CONH2 (SEQ ID NO: 191), Ac-DAPenT(2Ind)GEV(5MeO)WGREPenLQGGK(DBCO)-CONH2 (SEQ ID NO: 192), Ac-DAPenTWEVWGREPenLQGGK(DBCO)-CONH2 (SEQ ID NO: 193), Ac-DPCTWEVWGRECLQGGK(PEG5-DBCO)-CONH2 (SEQ ID NO: 194), Ac-DACT(2Ind)GEV(5MeO)WGRECLQGGK(DBCO)-CONH2 (SEQ ID NO: 195), AcDPPenT(2Ind)GEV(5MeO)WGREPenLQGGK(DBCO)-CONH2 (SEQ ID NO: 196), and AcDAPenT(2Ind)GEV(5MeO)WGREPenLQGGK(DBCO)-CONH2 (SEQ ID NO: 197), Ac-DPCTWEVWGRECLQGGK(PEG5-DBCO)-CONH$_2$ (SEQ ID NO: 198), or modifications thereof.

2. The therapeutic nanoparticle of claim 1, wherein the therapeutic nanoparticle has a hydrodynamic diameter of about 60 to about 150 nm.

3. The therapeutic nanoparticle of claim 2, wherein the hydrodynamic diameter is about 90 to about 140 nm.

4. The therapeutic nanoparticle of claim 1, comprising about 1 to about 10 weight percent of the therapeutic agent.

5. The nanoparticle of claim 1, comprising about 200 to about 500 of the PLA-PEG conjugated to the peptidyl ligand molecules.

6. The nanoparticle of claim 1, wherein the PLA-PEG conjugated to the peptidyl ligand molecules by reacting azide functionalized PLA-PEG and using a strain-promoted alkyne-azide cycloadditions.

7. The nanoparticle of claim 1, wherein the PLA of PLA-PEG has a number average molecular weight of about 15 to about 17 kDa.

8. The nanoparticle of claim 1, wherein the PEG of the PLA-PEG has a number of about 4 to about 6kDa.

9. A pharmaceutically acceptable composition comprising a plurality of therapeutic nanoparticles of claim 1 and a pharmaceutically acceptable excipient.

* * * * *